(12) United States Patent
Moore

(10) Patent No.: US 8,200,775 B2
(45) Date of Patent: Jun. 12, 2012

(54) ENHANCED SYNDICATION

(75) Inventor: James F. Moore, Lincoln, MA (US)

(73) Assignee: Newsilike Media Group, Inc, Lincoln, MA (US)

( * ) Notice: Subject to any disclaimer, the term of this patent is extended or adjusted under 35 U.S.C. 154(b) by 1278 days.

(21) Appl. No.: 11/223,826

(22) Filed: Sep. 10, 2005

(65) Prior Publication Data

US 2006/0173985 A1 Aug. 3, 2006

Related U.S. Application Data

(60) Provisional application No. 60/594,478, filed on Apr. 12, 2005, provisional application No. 60/594,456, filed on Apr. 10, 2005, provisional application No. 60/649,311, filed on Feb. 1, 2005, provisional application No. 60/649,312, filed on Feb. 1, 2005, provisional application No. 60/649,504, filed on Feb. 2, 2005, provisional application No. 60/649,502, filed on Feb. 2, 2005, provisional application No.

(Continued)

(51) Int. Cl.
 *G06F 15/16* (2006.01)
(52) U.S. Cl. ...................................................... 709/217
(58) Field of Classification Search ........... 709/217–219
 See application file for complete search history.

(56) References Cited

U.S. PATENT DOCUMENTS 5,664,109 A 9/1997 Johnson et al.

(Continued)

FOREIGN PATENT DOCUMENTS

WO 2003077558 A2 9/2003

(Continued)

OTHER PUBLICATIONS

Wood, Charlie "Introducing Spanning Feed Builder for AppExchange", http://www.spanningpartners.com/2006/07/introducing_spa.html, (Jul. 2, 2006).

(Continued)

*Primary Examiner* — Wing Chan
*Assistant Examiner* — Alicia Baturay
(74) *Attorney, Agent, or Firm* — GTC Law Group LLP & Affiliates

(57) ABSTRACT

A variety of tools and techniques are disclosed for managing, viewing, publishing, searching, clustering, and otherwise manipulating data streams. Data streams such as RSS data feeds may be searched, aggregated, and filtered into a processed feed. The processed feed, along with rules used to process the feed may be shared in a number of ways. A data feed management system may provide an integrated user interface through which a user may manage feeds, including searching for new feeds, managing and filtering current feeds, modifying a user profile, and sharing feeds and feed configuration data with other users. A server may provide a complementary search engine to locate new feeds and to store and/or index items or posts in known feeds. Together, these technologies may provide a richly-functioned feed management system and greater ease of use for individuals in managing large numbers of feeds and large amounts of data in feeds. Additional functional layers may provide for authentication, security, and privacy, metadata creation and management, and social networking features. Using the management tools and additional functionality, a syndicated data stream system may provide a platform for a wide array of useful consumer and business applications.

47 Claims, 41 Drawing Sheets

Related U.S. Application Data

60/657,840, filed on Mar. 1, 2005, provisional application No. 60/594,298, filed on Mar. 26, 2005, provisional application No. 60/594,416, filed on Apr. 6, 2005, provisional application No. 60/669,666, filed on Apr. 8, 2005, provisional application No. 60/673,661, filed on Apr. 20, 2005, provisional application No. 60/680,879, filed on May 13, 2005, provisional application No. 60/684,092, filed on May 23, 2005, provisional application No. 60/685,904, filed on May 31, 2005, provisional application No. 60/686,630, filed on Jun. 2, 2005, provisional application No. 60/688,826, filed on Jun. 9, 2005, provisional application No. 60/694,080, filed on Jun. 24, 2005, provisional application No. 60/695,029, filed on Jun. 28, 2005, provisional application No. 60/699,631, filed on Jul. 15, 2005, provisional application No. 60/700,122, filed on Jul. 18, 2005, provisional application No. 60/702,467, filed on Jul. 26, 2005, provisional application No. 60/703,688, filed on Jul. 29, 2005, provisional application No. 60/703,535, filed on Jul. 29, 2005, provisional application No. 60/703,544, filed on Jul. 29, 2005, provisional application No. 60/709,683, filed on Aug. 19, 2005.

(56) References Cited

U.S. PATENT DOCUMENTS

| | | |
|---|---|---|
| 5,784,635 A | 7/1998 | McCallum |
| 5,845,255 A | 12/1998 | Mayaud |
| 5,930,764 A | 7/1999 | Melchione et al. |
| 5,931,946 A | 8/1999 | Terada et al. |
| 5,933,136 A | 8/1999 | Brown |
| 6,022,315 A | 2/2000 | Iliff |
| 6,070,189 A | 5/2000 | Bender |
| 6,131,085 A | 10/2000 | Rossides |
| 6,199,082 B1 | 3/2001 | Ferrel et al. |
| 6,233,618 B1 | 5/2001 | Shannon |
| 6,253,210 B1 | 6/2001 | Smith et al. |
| 6,311,194 B1 | 10/2001 | Sheth et al. |
| 6,442,333 B1 | 8/2002 | Izawa |
| 6,551,243 B2 | 4/2003 | Bocionek et al. |
| 6,598,161 B1 | 7/2003 | Kluttz et al. |
| 6,678,764 B2 | 1/2004 | Parvulescu et al. |
| 6,734,886 B1 | 5/2004 | Hagan |
| 6,904,461 B1 | 6/2005 | Randhava et al. |
| 6,931,532 B1* | 8/2005 | Davis et al. ............ 713/167 |
| 6,954,532 B1 | 10/2005 | Handley et al. |
| 6,993,522 B2 | 1/2006 | Chen et al. |
| 7,010,681 B1 | 3/2006 | Fletcher et al. |
| 7,058,710 B2 | 6/2006 | McCall |
| 7,072,934 B2 | 7/2006 | Helgeson et al. |
| 7,117,504 B2 | 10/2006 | Smith et al. |
| 7,127,328 B2* | 10/2006 | Ransom ............ 700/286 |
| 7,142,691 B2 | 11/2006 | Levy |
| 7,146,415 B1 | 12/2006 | Doi |
| 7,149,813 B2 | 12/2006 | Flanagin et al. |
| 7,188,144 B2 | 3/2007 | Fuisz |
| 7,296,077 B2 | 11/2007 | Harmon et al. |
| 7,308,477 B1 | 12/2007 | Gress et al. |
| 7,406,427 B1 | 7/2008 | Guyan et al. |
| 7,412,534 B2 | 8/2008 | Tsang et al. |
| 7,421,155 B2 | 9/2008 | King et al. |
| 7,451,147 B1 | 11/2008 | Kao et al. |
| 7,472,349 B1 | 12/2008 | Srivastava |
| 7,519,591 B2 | 4/2009 | Landi et al. |
| 7,565,410 B2 | 7/2009 | Stickler |
| 7,584,208 B2* | 9/2009 | Spivack et al. ............ 707/103 R |
| 7,904,367 B2 | 3/2011 | Chung et al. |
| 7,949,666 B2* | 5/2011 | Wolff et al. ............ 707/753 |
| 8,010,282 B2 | 8/2011 | Barry et al. |
| 2001/0016851 A1 | 8/2001 | Gramsamer |
| 2001/0051881 A1 | 12/2001 | Filler |
| 2001/0052933 A1 | 12/2001 | Nybo et al. |
| 2001/0056359 A1 | 12/2001 | Abreu |
| 2002/0010616 A1 | 1/2002 | Itzhaki |
| 2002/0010764 A1 | 1/2002 | Spicer |
| 2002/0029157 A1 | 3/2002 | Marchosky |
| 2002/0032742 A1* | 3/2002 | Anderson ............ 709/206 |
| 2002/0038316 A1 | 3/2002 | Onyon |
| 2002/0049613 A1 | 4/2002 | Rice |
| 2002/0059049 A1 | 5/2002 | Bradbury |
| 2002/0059399 A1 | 5/2002 | Learmonth |
| 2002/0138467 A1 | 9/2002 | Jacobson |
| 2002/0143742 A1 | 10/2002 | Nonomura |
| 2002/0143819 A1 | 10/2002 | Han et al. |
| 2002/0152210 A1 | 10/2002 | Johnson |
| 2002/0152318 A1 | 10/2002 | Menon |
| 2002/0154178 A1 | 10/2002 | Barnett et al. |
| 2002/0188522 A1 | 12/2002 | McCall |
| 2003/0046434 A1 | 3/2003 | Flanagin |
| 2003/0050801 A1 | 3/2003 | Ries |
| 2003/0055818 A1 | 3/2003 | Faybishenko |
| 2003/0055825 A1 | 3/2003 | Chen |
| 2003/0061404 A1 | 3/2003 | Atwal et al. |
| 2003/0069751 A1 | 4/2003 | Lichtenstein |
| 2003/0074352 A1 | 4/2003 | Raboczi |
| 2003/0088544 A1 | 5/2003 | Kan |
| 2003/0126120 A1 | 7/2003 | Faybishenko |
| 2003/0217047 A1 | 11/2003 | Marchisio |
| 2003/0225718 A1 | 12/2003 | Shmulevich |
| 2003/0229692 A1 | 12/2003 | Vo |
| 2004/0002966 A1 | 1/2004 | Perkowski |
| 2004/0034550 A1 | 2/2004 | Menschik |
| 2004/0054675 A1 | 3/2004 | Li |
| 2004/0054722 A1 | 3/2004 | DeFloor |
| 2004/0064428 A1 | 4/2004 | Larkin |
| 2004/0073661 A1 | 4/2004 | Eibach |
| 2004/0078231 A1 | 4/2004 | Wilkes |
| 2004/0078236 A1 | 4/2004 | Stoodley |
| 2004/0093412 A1 | 5/2004 | Chen et al. |
| 2004/0133580 A1 | 7/2004 | Liu |
| 2004/0139317 A1 | 7/2004 | Fornberg |
| 2004/0139327 A1 | 7/2004 | Brown |
| 2004/0143623 A1 | 7/2004 | Fukui et al. |
| 2004/0172423 A1 | 9/2004 | Kaasten |
| 2004/0181679 A1 | 9/2004 | Dettinger |
| 2004/0207659 A1 | 10/2004 | Goodman et al. |
| 2004/0221226 A1 | 11/2004 | Lin et al. |
| 2004/0224674 A1 | 11/2004 | O'Farrell et al. |
| 2004/0230674 A1 | 11/2004 | Pourheidari |
| 2004/0254816 A1 | 12/2004 | Myers |
| 2004/0260767 A1 | 12/2004 | Kedem |
| 2004/0267610 A1 | 12/2004 | Gossett |
| 2005/0027567 A1 | 2/2005 | Taha |
| 2005/0027871 A1 | 2/2005 | Bradley |
| 2005/0038717 A1 | 2/2005 | McQueen |
| 2005/0055308 A1 | 3/2005 | Meyer |
| 2005/0108057 A1 | 5/2005 | Cohen |
| 2005/0120300 A1 | 6/2005 | Schwager |
| 2005/0132048 A1 | 6/2005 | Kogan |
| 2005/0160065 A1* | 7/2005 | Seeman ............ 707/1 |
| 2005/0165615 A1 | 7/2005 | Minar |
| 2005/0198021 A1 | 9/2005 | Wilcox |
| 2005/0216315 A1 | 9/2005 | Andersson |
| 2005/0234740 A1 | 10/2005 | Krishnan et al. |
| 2005/0262340 A1 | 11/2005 | Rabb |
| 2005/0267973 A1 | 12/2005 | Carlson et al. |
| 2005/0289468 A1 | 12/2005 | Kahn et al. |
| 2006/0004691 A1 | 1/2006 | Sifry |
| 2006/0004764 A1 | 1/2006 | Kurhekar |
| 2006/0010251 A1 | 1/2006 | Mrsic-Flogel |
| 2006/0053156 A1 | 3/2006 | Kaushansky et al. |
| 2006/0059208 A1 | 3/2006 | Chen |
| 2006/0064320 A1 | 3/2006 | Postrel |
| 2006/0064326 A1 | 3/2006 | Tucker |
| 2006/0073812 A1* | 4/2006 | Punaganti et al. ............ 455/412.1 |
| 2006/0074980 A1* | 4/2006 | Sarkar ............ 707/104.1 |
| 2006/0075426 A1 | 4/2006 | Koch |
| 2006/0080166 A1 | 4/2006 | Takahashi |

| | | | |
|---|---|---|---|
| 2006/0085412 A1 | 4/2006 | Johnson | |
| 2006/0095507 A1 | 5/2006 | Watson | |
| 2006/0095628 A1 | 5/2006 | Ludwig et al. | |
| 2006/0101035 A1* | 5/2006 | Mustakallio et al. | 707/100 |
| 2006/0106655 A1 | 5/2006 | Lettovsky et al. | |
| 2006/0106748 A1 | 5/2006 | Chafle | |
| 2006/0111938 A1 | 5/2006 | Vitiello | |
| 2006/0112076 A1* | 5/2006 | Burris et al. | 707/3 |
| 2006/0136259 A1 | 6/2006 | Weiner | |
| 2006/0149591 A1 | 7/2006 | Hanf | |
| 2006/0155698 A1 | 7/2006 | Vayssiere | |
| 2006/0167860 A1 | 7/2006 | Eliashberg | |
| 2006/0173985 A1 | 8/2006 | Moore | |
| 2006/0178910 A1 | 8/2006 | Eisenberger et al. | |
| 2006/0178918 A1 | 8/2006 | Mikurak | |
| 2006/0184617 A1 | 8/2006 | Nicholas | |
| 2006/0188327 A1 | 8/2006 | Moon | |
| 2006/0200478 A1 | 9/2006 | Pasztor | |
| 2006/0221076 A1 | 10/2006 | Takahashi | |
| 2006/0229911 A1 | 10/2006 | Gropper et al. | |
| 2006/0230011 A1 | 10/2006 | Tuttle | |
| 2006/0230021 A1 | 10/2006 | Diab | |
| 2006/0230221 A1 | 10/2006 | Hsu | |
| 2006/0247961 A1 | 11/2006 | Klemow | |
| 2006/0265489 A1 | 11/2006 | Moore | |
| 2006/0265508 A1 | 11/2006 | Angel | |
| 2006/0288011 A1 | 12/2006 | Gandhi et al. | |
| 2006/0288329 A1 | 12/2006 | Gandhi et al. | |
| 2007/0011665 A1 | 1/2007 | Gandhi | |
| 2007/0011710 A1 | 1/2007 | Chiu | |
| 2007/0038712 A1 | 2/2007 | Affronti et al. | |
| 2007/0050446 A1 | 3/2007 | Moore | |
| 2007/0061266 A1 | 3/2007 | Moore et al. | |
| 2007/0061393 A1 | 3/2007 | Moore et al. | |
| 2007/0073934 A1 | 3/2007 | Rogers | |
| 2007/0079237 A1 | 4/2007 | Abrams | |
| 2007/0081550 A1 | 4/2007 | Moore | |
| 2007/0088807 A1 | 4/2007 | Moore | |
| 2007/0094156 A1 | 4/2007 | Isaacs | |
| 2007/0094350 A1 | 4/2007 | Moore | |
| 2007/0094365 A1* | 4/2007 | Nussey et al. | 709/223 |
| 2007/0094389 A1* | 4/2007 | Nussey et al. | 709/225 |
| 2007/0100959 A1 | 5/2007 | Eichstaedt et al. | |
| 2007/0106536 A1 | 5/2007 | Moore | |
| 2007/0106537 A1 | 5/2007 | Moore | |
| 2007/0106649 A1 | 5/2007 | Moore | |
| 2007/0106650 A1 | 5/2007 | Moore | |
| 2007/0106750 A1 | 5/2007 | Moore | |
| 2007/0106751 A1 | 5/2007 | Moore | |
| 2007/0106752 A1 | 5/2007 | Moore | |
| 2007/0106753 A1 | 5/2007 | Moore | |
| 2007/0106754 A1 | 5/2007 | Moore | |
| 2007/0116036 A1 | 5/2007 | Moore | |
| 2007/0116037 A1 | 5/2007 | Moore | |
| 2007/0130457 A1 | 6/2007 | Kamat | |
| 2007/0143215 A1 | 6/2007 | Willems | |
| 2007/0150482 A1 | 6/2007 | Taylor | |
| 2007/0156809 A1 | 7/2007 | Dickinson | |
| 2007/0168461 A1 | 7/2007 | Moore | |
| 2007/0207782 A1 | 9/2007 | Tran | |
| 2007/0220016 A1 | 9/2007 | Estrada | |
| 2007/0225047 A1 | 9/2007 | Bakos | |
| 2007/0245020 A1 | 10/2007 | Ott | |
| 2008/0005086 A1 | 1/2008 | Moore | |
| 2008/0040151 A1 | 2/2008 | Moore | |
| 2008/0046369 A1 | 2/2008 | Wood | |
| 2008/0046437 A1 | 2/2008 | Wood | |
| 2008/0046471 A1 | 2/2008 | Moore et al. | |
| 2008/0052162 A1 | 2/2008 | Wood | |
| 2008/0052343 A1 | 2/2008 | Wood | |
| 2008/0126178 A1 | 5/2008 | Moore | |
| 2008/0126476 A1 | 5/2008 | Nicholas | |
| 2008/0141126 A1 | 6/2008 | Johnson et al. | |

FOREIGN PATENT DOCUMENTS

| | | | |
|---|---|---|---|
| WO | 03077558 A2 | 9/2004 | |
| WO | WO-2006083958 A2 | 8/2006 | |
| WO | WO-2007130865 A2 | 11/2007 | |
| WO | WO-2007137145 A2 | 11/2007 | |
| WO | WO-2008036464 A2 | 3/2008 | |

OTHER PUBLICATIONS

Wood, Charlie "Blog of Subscribe Your Calendar to Your Salesforce.com Events", http://globelogger.com/item.php?id=660, (May 12, 2006).

Gawlick, Dieter et al., "Using the Oracle Database as a Declarative RSS Hub", *International Conference on Management of Data*, Proceedings of the 2006 ACM SIGMOD international conference on Management of data,(2006), 722.

USPTO, "U.S. Appl. No. 11/458,092, Non-Final Office Action mailed Jun. 9, 2008", OARN,23 pgs.

Appnel, T. "RSS: The Web Services We Already Have", (Jan. 22, 2003).

Maurer, L. "U.S. Appl. No. 09/584,318 (Appendix)", (May 31, 2000).

USPTO, ""U.S. Appl. No. 11/615,030 Non Final Office Action mailed Jan. 23, 2008"", (Jan. 23, 2008),all.

Wood, Charlie "Subscribe Your Calendar to Your Salesforce.com Events", http://www.spanningpartners.com/2006/05/subscribe_your_.html, (May 12, 2006).

Wood, Charlie "RSS-Enabled AppExchange Applications", http://www.spanningpartners.com/2006/05/spanning_partne_1.html, (May 30, 2006).

Wood, Charlie "Latest Spanning Salesforce Release", http://www.spanningpartners.com/2006/04/latest_spanning.html, (Apr. 5, 2006).

Wood, Charlie "New Spanning Salesforce Feeds and Features", http://globelogger.com/item.php?id=606, (Mar. 14, 2006).

Wood, Charlie "On Creating Real Business Value with RSS", http://www.spanningpartners.com/2006/02/on_creating_rea.html, (Feb. 23, 2006).

Wood, Charlie "Spanning Salesforce 2.0 is Live", http://globelogger.com/item.php?id=466, (Aug. 28, 2005).

Wood, Charlie "Introducing Spanning Salesforce 2.0", http://www.spanningpartners.com/2005/08/introducing_spa.html, (Aug. 28, 2005).

Wood, Charlie "Adoption Using RSS to Track Sales Leads", http://globelogger.com/item.php?id=285, (Jan. 28, 2005).

Wood, Charlie "Adoption Salesforce.com via RSS", http://globelogger.com/item.php?id=294, (Feb. 6, 2005).

Wood, Charlie "Spanning Salesforce Goes Public", http://globelogger.com/item.php?id=285, (Jul. 17, 2005).

Krill, Paul "Microsoft to demo CRM-RSS", http://weblog.infoworld.com/techwatch/archives/003933.html, (Sep. 7, 2005).

Lewin, James, An Introduction to RSS news feeds Using open formats for content syndication, 2000.

Drugs and Herbs, http://web.archive.org/web/20051101101459/http://www.webmd.com/drugs/index-drugs.aspx, 2005.

Ponnekanti, Sword, A Developer Toolkit for Web Service Composition, 2002, pp. 1-25.

Stahl, Web Services: Beyond Component Based Computing Seeking a Better Solution to the Application Integration Problem, Communications of the ACM, vol. 45, No. 10, pp. 71-76, 2002.

Pilgrim, How to consume RSS safely, 2003, pp. 1-27.

Nakano, A proposal of RSS WebCrawler model of product information, Active Media Technology, Proceedings of the 2005 International Conference on, vol., No., pp. 147-151, 2005.

Marshall, HTTP Made Really Easy, A Practical Guide to Writing Clients and Servers, 1997.

Urchin RSS Aggregator pp. 1-5.

Refsnes Data, W3Schools Online Web Tutorials, 2002, pp. 3-5.

Related U.S. Appl. No. 11/925,930, 2007.

International Search Report, PCT/US07/069195 (4 pages), 2008.

International Preliminary Report on Patentability, PCT/US07/069195 (6 pages), 2008.

Written Opinion of the International Searching Authority, PCT/US07/069195 (5 pages), 2008.

OPML 1.0 Specification, 2000, pp. 1-4.

Winer, OPML About Page, p. 1, 2000.
Definition Metadata, Webster's New World Computer Dictionary, 2003.
Urchin, Notes for Webmasters, 2003, pp. 1-8.
Written Opinion of the International Searching Authority, PCT/US07/74475 (3 pages), 2008.
International Preliminary Report on Patentability, PCT/US07/74475 (4 pages), 2008.
Scheier, "Applied Cryptography: Protocols, Algorithms, and Source Code in C", 1996, John Wiley & Sons, Inc., Second Edition, pp. 584-587.
UDDI Version 2.04 API Specification, p. 6, 2002.
RDF Primer, W3C Recommendation, pp. 1-118, 2004.
Kifer et al., Database Systems: An Application-Oriented Approach, 2005, Addison-Wesley, Second Edition, pp. 1151-1152.
International Search Report, PCT/US07/74475 (3 pages), 2008.
"Serve." Chambers 21st Century Dictionary. London: Chambers Harrap, 2001. Credo Reference. [online][retrieved on Jul. 10, 2011].
"Service." Chambers 21st Century Dictionary. London: Chambers Harrap, 2001. Credo Reference. [online][retrieved on Jul. 10, 2011].
"Customer." Roget's II The New Thesaurus. Boston: Houghton Mifflin, 2003. Credo Reference. [online][retrieved on Jul. 10, 2011].
FEMA, FEMA: RSS, Apr. 16, 2005, web.archive.org/web/20050416033644/http://www.fema.gov/help/rss.shtm.
FEMA, FEMA: News Releases, Apr. 3, 2005, web.archive.org/web/20050403173625/www.fema.gov/news/recentnews_rss.fema.
Hammond, The Role of Rss in Science Publishing, D-Lib Magazine, vol. 10 No. 12, Dec. 2004, pp. 1-17.
International Search Report, PCT/US06/27794 (5 pages), 2007.
International Preliminary Report on Patentability, PCT/US06/27794 (7 pages), 2007.
Written Opinion of the International Searching Authority, PCT/US06/27794 (6 pages), 2007.
International Search Report, PCT/US07/67643 (2 pages), 2008.
International Preliminary Report on Patentability, PCT/US07/67643 (6 pages), 2008.
Written Opinion of the International Searching Authority, PCT/US07/67643 (5 pages), 2008.
PS Mar. 10, 2004 Digital Imaging and Communications (DICOM) part 10, National Electronics Manufactures Association, 2004.
Definition: Dicom introduction. http://www.cabiatl.com/mricro/dicom/index.html11/458,092, 2004.
Related U.S. Appl. No. 11/925,931, 2007.
Related U.S. Appl. No. 11/925,932, 2007.
Related U.S. Appl. No. 11/925,934, 2007.
Related U.S. Appl. No. 11/925,935, 2007.
Roszkowski, etal, A Distributed Architecture for Resource Discovery Using Metadata, D-Lib Magazine, pp. 1-11, Jun. 1998.
Winer, OPML About Page, p. 1, 2008.
Related U.S. Appl. No. 11/925,936, 2007.
Related U.S. Appl. No. 11/925,939, 2007.
Related U.S. Appl. No. 11/925,940, 2007.
Related U.S. Appl. No. 11/925,941, 2007.
Related U.S. Appl. No. 11/925,943, 2007.
Related U.S. Appl. No. 11/926,161, 2007.
Related U.S. Appl. No. 11/926,164, 2007.
Related U.S. Appl. No. 11/926,165, 2007.
Related U.S. Appl. No. 11/926,166, 2007.
Related U.S. Appl. No. 11/926,171, 2007.
Related U.S. Appl. No. 11/926,173, 2007.
Related U.S. Appl. No. 11/926,175, 2007.
Related U.S. Appl. No. 11/926,178, 2007.
Related U.S. Appl. No. 11/926,182, 2007.
Related U.S. Appl. No. 11/926,185, 2007.
Related U.S. Appl. No. 11/223,826, 2007.
Related U.S. Appl. No. 11/346,586, 2007.
Related U.S. Appl. No. 11/346,587, 2007.
Related U.S. Appl. No. 11/346,588, 2007.
Related U.S. Appl. No. 11/380,923, 2007.
Related U.S. Appl. No. 11/458,092, 2007.
Related U.S. Appl. No. 11/608,261, 2007.
Related U.S. Appl. No. 11/608,277, 2007.
Related U.S. Appl. No. 11/608,327, 2007.
Related U.S. Appl. No. 11/608,398, 2007.
Related U.S. Appl. No. 11/608,492, 2007.
Related U.S. Appl. No. 11/615,030, 2007.
Related U.S. Appl. No. 11/615,039, 2007.
Related U.S. Appl. No. 11/615,087, 2007.
Related U.S. Appl. No. 11/615,161, 2007.
Related U.S. Appl. No. 11/615,165, 2007.
Related U.S. Appl. No. 11/615,172, 2007.
Related U.S. Appl. No. 11/615,224, 2007.
Related U.S. Appl. No. 11/615,340, 2007.
Related U.S. Appl. No. 11/615,392, 2007.
Related U.S. Appl. No. 11/615,451, 2007.
Related U.S. Appl. No. 11/828,910, 2007.
Related U.S. Appl. No. 11/828,919, 2007.
Related U.S. Appl. No. 11/828,928, 2007.
Related U.S. Appl. No. 11/828,939, 2007.
Related U.S. Appl. No. 11/828,945, 2007.
Related U.S. Appl. No. 11/828,949, 2007.
Related U.S. Appl. No. 12/393,170, 2007.
Related U.S. Appl. No. 11/557,271, 2007.
Related U.S. Appl. No. 11/828,903, 2007.
Related U.S. Appl. No. 11/951,307, 2007.
Related U.S. Appl. No. 12/233,266, 2007.

* cited by examiner

FIG. 8

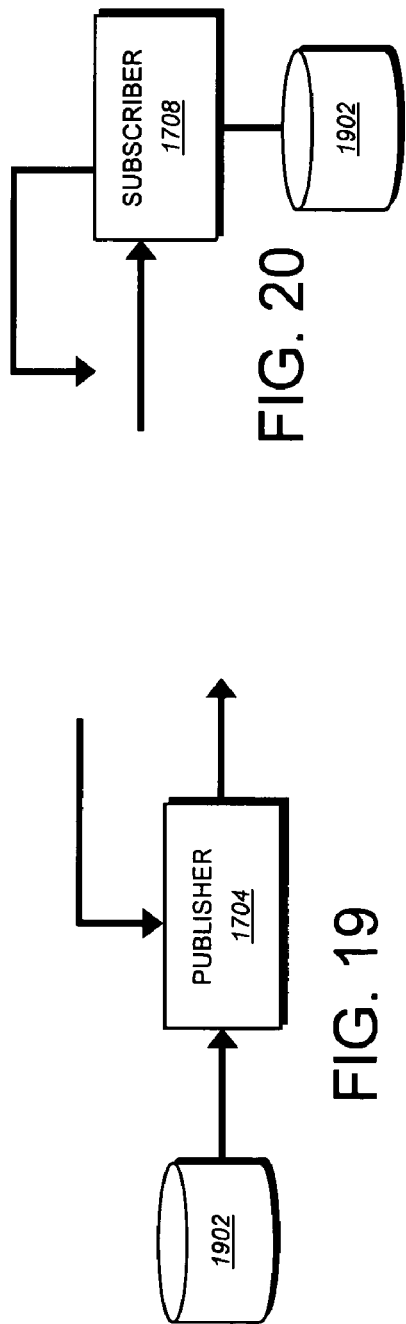
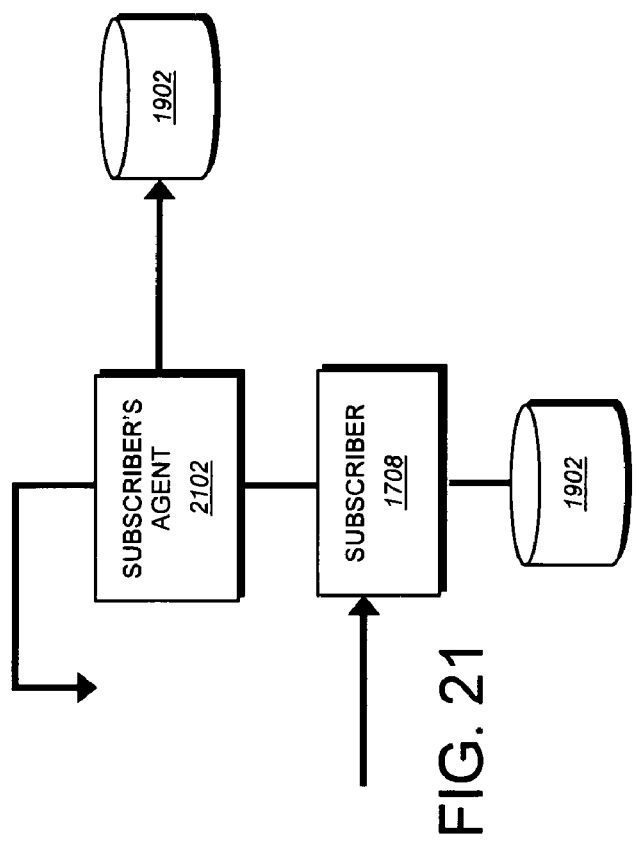
FIG. 20
FIG. 21
FIG. 19

```
</S-DEFINITION version="1" text="This is an example S-message">
    <BODY type="OPML" version="1.1">
        <OUTLINE text="News I Like"url=http://www.newsilike.com/>
        <OUTLINE text="Google"url=http://www.google.com/>
    </BODY >
    <CHANNEL>
        <TITLE>This is a channel title</TITLE>
        <TTL>60</TITLE>
        <ITEM>
            <TITLE>This is an item title</TITLE>
        </ITEM>
    <CHANNEL>
    <CHANNEL>
        <TITLE>This is another channel title</TITLE>
        <TTL>60</TTL>
        <ITEM>
            <TITLE>This is another item title</TITLE>
        </ITEM>
    <CHANNEL>
    <BODY type="S-DEFINITION"version="1">
        <OUTLINE>
            <TEXT>an item in an S-DEFINITION OUTLINE</TEXT>
            <URL>http://www.s-definition.com</URL>
        </OUTLINE>
        <OUTLINE>
            <CHANNEL>
                <TITLE>Yet another channel title</TITLE>
                <ITEM>
                    <TITLE>This is an item title</TITLE>
                </ITEM>
            </CHANNEL>
        </OUTLINE>
    </BODY>
</S-DEFINITION>
```

FIG. 25

```
</S-DEFINITION version="1" text="This is an example of an S-message representative of a revision history">
    <FILESET >
            <FILE>patent.doc</FILE>
            <FILE>patent.xls</FILE>
    </FILESET >
    <SYMBOLIC REVISION name="The version we sent to the customer">
            <FILE id="1.1">patent.doc</FILE>
            <FILE id="1.1">patent.xls</FILE>
    </SYMBOLIC REVISION>
    <REVISIONHISTORY>
            <FILE>patent.doc</FILE>
            </REVISION id="1.2"type="automatic" reason="software crash"/>
                    <DATE>24-JUN-05</DATE>
                    <TIME>05:00:00 GMT</TIME>
                    <FILE>patent.doc.1.2</FILE>
                    <AUTOMATIC REVISION>

</REVISION>
            <REVISION id="1.1" />
                    <DATE>23-JUN-05</DATE>
                    <TIME>12:34:56 GMT</TIME>
                    <FILE>http://www.bigarchive.com/patent.doc.1.1</FILE>
            </REVISION>
    </REVISIONHISTORY>
    <REVISIONHISTORY>
            <FILE>patent.xls</FILE>
            <MERGE>
                    <FILE id="1.1.1">patent.xls</FILE>
                    <FILE id="1.1">patent.xls</FILE>
                    <REVISION id="1.2">
                            <DATE>24-JUN-05</DATE>
                            <TIME>5:34:23 GMT</TIME>
                            <FILE>patent.xls.1.2</FILE>
                    </REVISION>
            </MERGE>
            <BRANCH>
                    <TRUNK>
                            <REVISION id="1.1"/>
                    </TRUNK>
                    <REVISION id=1.1.1>
                            <DATE>24-JUN-05</DATE>
                            <TIME>1:23:45 GMT</TIME>
                            <FILE>patent.xls.1.2</FILE>
                    </REVISION>
            </BRANCH>
            <REVISION id="1.1">
                    <DATE>23-JUN-05</DATE>
                    <TIME>15:00:01 GMT</TIME>
                    <FILE>patent.xls.1.1</FILE>
            </REVISION>
    </REVISIONHISTORY>
</S-DEFINITION>
```

FIG. 26

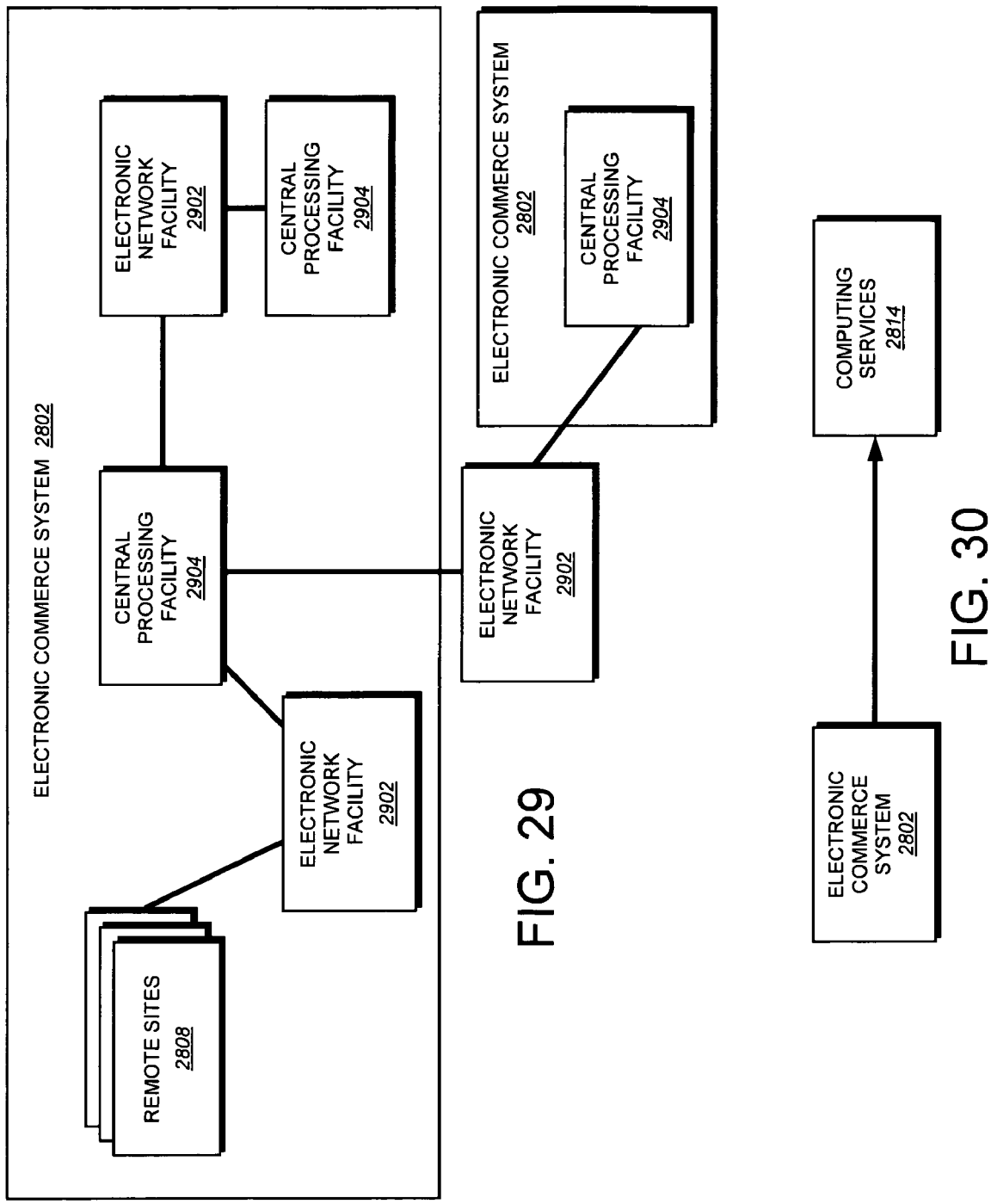

ENHANCED SYNDICATION

RELATED APPLICATIONS

This application claims the benefit of the following commonly owned U.S. Provisional Applications, each of which is hereby incorporated by reference in its entirety:

Ser. No. 60/649,311, filed on Feb. 1, 2005, and entitled DATA STREAM MANAGEMENT.

Ser. No. 60/649,312, filed on Feb. 1, 2005, and entitled DATA STREAM MANAGEMENT SOFTWARE.

Ser. No. 60/649,504, filed on Feb. 2, 2005, and entitled RSS MEDIA PROCESSING SYSTEMS.

Ser. No. 60/649,502, filed on Feb. 2, 2005, and entitled SEMANTIC PROCESSING.

Ser. No. 60/657,840, filed on Mar. 1, 2005, and entitled USER INTERFACES AND WORKFLOWS FOR USE WITH DATA STREAM MANAGEMENT SYSTEMS.

Ser. No. 60/594,298, filed on Mar. 26, 2005, and entitled USES OF METADATA IN A STRUCTURED DATA FEED ENVIRONMENT.

Ser. No. 60/594,416, filed on Apr. 6, 2005, and entitled DATA STREAM MANAGEMENT.

Ser. No. 60/669,666, filed on Apr. 8, 2005, and entitled DATA STREAM MANAGEMENT.

Ser. No. 60/594,456, filed on Apr. 10, 2005, and entitled FUNCTIONAL SEARCH OUTLINES.

Ser. No. 60/594,478, filed on Apr. 12, 2005, and entitled DATA STREAM MANAGEMENT.

Ser. No. 60/673,661, filed on Apr. 20, 2005, and entitled DATA STREAM MANAGEMENT.

Ser. No. 60/680,879, filed on May 13, 2005, and entitled DATA STREAM SECURITY SYSTEMS.

Ser. No. 60/684,092, filed on May 23, 2005, and entitled FUNCTIONAL SEARCH OUTLINES.

Ser. No. 60/685,904, filed on May 31, 2005, and entitled WIRELESS DELIVERY OF RSS CONTENT.

Ser. No. 60/686,630, filed on Jun. 2, 2005, and entitled DATA STREAM ADVERTISING.

Ser. No. 60/688,826, filed on Jun. 9, 2005, and entitled USES OF OUTLINES AND STRUCTURED DATA.

Ser. No. 60/694,080, filed on Jun. 24, 2005, and entitled USES OF LISTS, OUTLINES AND STRUCTURED DATA.

Ser. No. 60/695,029, filed on Jun. 28, 2005, and entitled EVALUATION OF DATA FEED CONTENT.

Ser. No. 60/699,631, filed on Jul. 15, 2005, and entitled OPML SEARCH ENGINES AND SUPERSERVICES.

Ser. No. 60/700,122, filed on Jul. 18, 2005, and entitled WEB SUPERSERVICES.

Ser. No. 60/702,467, filed on Jul. 26, 2005, and entitled VERTICAL MARKETS AND FEATURES FOR ENHANCED WEB SYSTEMS.

Ser. No. 60/703,688, filed on Jul. 29, 2005, and entitled OPML SYSTEMS.

Ser. No. 60/703,535, filed on Jul. 29, 2005, and entitled OPML CONVERTER.

Ser. No. 60/703,544, filed on Jul. 29, 2005, and entitled OPML SEARCH ENGINE.

Ser. No. 60/709,683, filed on Aug. 19, 2005, and entitled USER INTERFACES FOR OPML SEARCH ENGINES.

BACKGROUND

1. Field of Invention

The invention relates to syndication, and more specifically to systems for expanding the functionality a flexibility of RSS and other syndicated media.

2. Description of Related Art

Really Simple Syndication ("RSS") media presents an emerging trend in networked communications involving the direct production and manipulation of text and multimedia by end users.

The public sees this layer primarily in terms of blogging—that is, the act of individuals creating Web sites and adding to them more or less daily. By dramatically increasing production and sharing of Web-based content, the blogging movement now produces a virtual river of content—available continuously and with global circulation. Just as word processing empowered millions to create their own documents, blogging software has made it relatively easy for millions to produce their own Web sites and keep them continually updated. By the promotion of a simple underlying standard for sharing text and other media, blogging has popularized the "syndication" or passing on of content borrowed from others—extending the reach of any given blogger and further increasing the total quantity of information in circulation.

A number of companies have emerged as niche players targeting various aspects of syndicated data streams. For example, some companies such as FeedDemon, NewsGator, myYahoo (Yahoo), and Bloglines have focused on client-side aggregation and presentation. Companies such as Technorati, Google, and Feedster have focused on the complementary services of searching for data feeds of interest. Other companies have focused on technologies for providing syndicated data streams such as SixApart, Drupal, TypePad, Flickr, Picasa (Google), and Blogger (Google). Other companies have positioned themselves as content providers, including new companies such as Engadget, Weblogs Inc., Topix.net, and MySpace, as well as established media companies such as the New York Times and BBC. Of course, various generic Internet technologies are also relevant to the rapidly growing weblog data flow, such as BitTorrent or Akamai's EdgePlatform.

While offering significant advancement in terms of sharing and communication of news and other items, the RSS value chain remains weak in many areas, and could benefit from better integration and additional layers of functionality. For example, RSS is relatively weak in terms of presentation, search, signal, and network routing. Aggregators that centralize content use display formats that are widely criticized, despite a general agreement among users that they improve over conventional search engine displays. In its current form, RSS also fails to provide enterprise-class features such as security, privacy, data integrity, and quality of service.

Remarkably, the rapidly growing content pool and the wide array of associated services and software technologies have arisen without the benefit of industry standards or formal commercial agreement on protocols. Thus, the underlying RSS technology remains very rudimentary. There remains a need for enhanced data stream services, and for an improved user interface and client tools for managing, receiving, and creating syndicated data streams.

SUMMARY OF THE INVENTION

A variety of tools and techniques are disclosed for managing, viewing, publishing, searching, clustering, and otherwise manipulating data streams. Data streams such as RSS data feeds may be searched, aggregated, and filtered into a processed feed. The processed feed, along with rules used to process the feed may be shared in a number of ways. A data feed management system may provide an integrated user interface through which a user may manage feeds, including searching for new feeds, managing and filtering current feeds, modifying a user profile, and sharing feeds and feed configuration data with other users. A server may provide a complementary search engine to locate new feeds and to store and/or index items or posts in known feeds. Together, these technologies may provide a richly-functioned feed management system and greater ease of use for individuals in managing large numbers of feeds and large amounts of data in feeds. Additional functional layers may provide for authentication, security, and privacy, metadata creation and management, and social networking features. Using the management tools and additional functionality, a syndicated data stream system may provide a platform for a wide array of useful consumer and business applications.

An enhanced syndication system as described herein includes a syndication platform. The syndication platform may support publication of content. Publication of content may include publication of an item in one or more of a defined channel, a data feed, or a data stream. Publication of content may include publication of an outline. The outline may be expressed in an XML schema. The XML schema may include Outline Processing Markup Language content. The syndication platform may support subscription to content. Subscription to content may include subscription to a defined channel. The syndication platform may support aggregation of content. The syndication platform may support republication of aggregated content. The syndication platform may include a syndication markup language. The syndication markup language may include one or more of RSS, RDF, or Atom. The content may include one or more data feeds. The content may include an XML schema. The content may include structured data. The content may be structured using an outlining markup language.

In one aspect, the system may employ an application layer. The application layer may include a user interface. The application layer may provide one or more social networking functions. The application layer may include a client-side application. The application layer may include a server-side application. The application layer may include a Java applet. The application layer may include a Java application. The application layer may include a Web services application. The application layer may include a SOA application. The application layer may include a word processing application. The application layer may include a spreadsheet application. The application layer may include a presentation application. The application layer may include a database application. The application layer may be adapted for a vertical market. The application layer may include one or more viewers. The application layer may include financial transaction processing. The application layer may include an alert. The application layer may act upon data. The application layer may analyze data. The application layer may include one or more event-action pairs. The application layer may include a financial services application. The application layer may include a health care application. The application layer may include an e-commerce application. The application layer may include a communications application. The application layer may include an advertising application. The application layer may include a sales application. The application layer may include a marketing application. The application layer may include a supply chain management application. The application layer may include a reporting application. The application layer may include an analytical application.

In one example of a vertical market supported by the application layer, a method for tracking a health condition of a population may include: aggregating syndicated content from a plurality of health care providers who are responsible for treating the health condition; analyzing the aggregated content to determine a trend in the health condition; and taking an action based on the trend. The action may include providing an alert as the presence of the condition in the population. The action may include determining an origin of the condition in the population. The action may include providing a quarantine of patients diagnosed with the condition.

In one aspect, the system may include processing services. The processing services may include a filter service. The filter service may filter one or more data feeds for relevance. The filter may determine relevance using one or more of Boolean search expressions, keyword searches, author searches, content searches, semantic analysis, recommendations, popularity, and the like. The filter service may include a spam filter. The filter service may include a spyware filter. The filter service may include a junk mail filter. The filter service may include an adult content filter. The filter service may include a preferred content filter. The filter service may include an authenticated content filter. The filter service may include a time-based filter. The filter service may include an event-based filter. The filter service may include a content-based filter. The filter service may include a semantic processing filter. The filter service may include a content type filter. The content type may include a file format type. The content type may include a metadata-specified type. The filter service may include a category filter. The processing service may include a search service. The search service may support a search for data feeds. The search service may support a search for items within a data feed. The search service may use an indexed database of content published within the syndication platform. The processing service may include a cluster service. The cluster service may support aggregation of one or more data feeds and/or one or more filters into a new data feed. The processing service may include a format service. The format service may specify one or more display parameters for published content. The processing service may include a service supported by an XML schema registered in the xml.org registry of schemas.

In one aspect, the system may include a data service. The data service may include a database service. The data service may include a search service. The search service may index content in a publicly available database. The index may facilitate data retrieval by one or more of time, author, title, source, keywords, metadata, and content. The search service may include a spider that searches a network for data. The spider may include logic for traversing an outline tree. The data service may include a search engine. The data service may search a network and generate a searchable repository of data feeds and items within data feeds. The data service may include a searchable database of data feeds and items within data feeds. The data service may include a cluster service. The data service may include a quality service. The data service may include a transformation service. The data service may include a store service. The data service may include a manipulate service. The data service may include a retrieve service. The data service may include a transform service. The data service may include a pipeline service. The data service may include a deduplicate service. The data service may include a cleanse service. The data service may include a verify service. The data service may include an authenticate service. The data service may include a format service. The data service may include a reformat service. The data service may include a tag service. The data service may include a link service. The data service may include a hyperlink service. The data service may include a report service. The data service may include a view service. The data service may stored syndicated content in a relational database. The relational database may be optimized for rapid retrieval of the syndicated content. The relational database may be optimized for rapid writing of syndicated content to the database. The data service may store metadata associated with syndicated content.

In one aspect, the system may include a semantic service. The semantic service may include an outlining service. The outlining service may use the Outline Processing Markup Language. The semantic service may provide an outline structure for syndicated content. The outline structure may include semantic links of the syndicated content to other content. The other content may include structured data from a relational database. The other content may include web content. The syndicated content may include aggregated news content relating to an entity, and the other content may include stored data relating to the entity. The entity may include a company and the data may relate to financial instruments of the company. The financial instruments may include one or more of publicly traded securities, bonds, privately held securities, options, and futures contracts. The semantic service may structure content. The semantic service may format content. The semantic service may enrich content. The semantic service may add metadata. The semantic service may modify metadata. The semantic service may remove metadata. The semantic service may include a language interpreter. The semantic service may analyze content of an item managed by the syndication platform. The semantic service may categorize an item managed by the syndication platform. The semantic service may categorize the item using one or more of reader feedback, a dictionary, a thesaurus, and semantic content analysis. The semantic service may include a parser.

In one aspect, a system disclosed herein may include a syndication platform, the syndication platform managing publication of a plurality of data feeds including a plurality of items; a semantic service associated with the syndication platform, the semantic service providing automated semantic analysis of one or more of the plurality of items.

The semantic service may associate one of the items with one or more other ones of the plurality of items. The semantic service may include an outlining service. The outlining service may use the Outline Processing Markup Language. The outlining service may interrelate the plurality of items in a hierarchical tree structure. The system may further include a plurality of outlines, each outline describing relationships between a plurality of items. At least one of the plurality of items may be an outline. At least one of the items may include data from a relational database. At least one of the items may include a file. The file may include one or more of an audio file, an image file, a movie file, a word processing file, a spreadsheet file, a presentation file, a document, an HTML file, a text file, an executable file, and a script. The semantic service may categorize one or more of the plurality of items. The semantic service may categorize items according to file type. The semantic service may categorize items according to popularity. The semantic service may categorize items according to relationships with other items. The semantic service may categorize items according to user annotations. The semantic service may enrich metadata associated with one or more of the items. The semantic service may enrich metadata using a dictionary. The semantic service may enrich metadata using a thesaurus. The semantic service may enrich metadata by analyzing a relationship of one of the items to one or more other ones of the items. The semantic service may enrich metadata by analyzing one or more of a time of publication of an item, an author of an item, a source of an item, or metadata of an item. The semantic service may enrich metadata by analyzing a body of an item. The semantic service may perform a language analysis of content of the body. The semantic service may enrich content of one of the plurality of items. At least one of the plurality of data feeds may include an aggregated data feed from a plurality of sources. The aggregated data feed may be filtered before publication. The aggregated data feed may include aggregated news content relating to an entity. The plurality of items may include stored data relating to the entity. The entity may include a corporate entity and the stored data may include stored data relating to one or more financial instruments of the corporate entity. The financial instrument may include one or more of a publicly traded security, a bond, a privately held security, an option, and a futures contract. The semantic service may structure content of the plurality of items by associating items according to a semantic relationship of the items. The semantic service may format one of the plurality of items for display according to a semantic evaluation. The semantic service may modify metadata for one of the plurality of items. The semantic service may include a language interpreter. The semantic service may store semantic data in a searchable archive.

The system may further include a user interface adapted to display one of the items according to semantic content of the item.

In one aspect, the system may include an infrastructure service. The infrastructure service may include security. The infrastructure service may include authentication. The infrastructure service may include traffic management. The infrastructure service may include pinging. The infrastructure service may support non-repudiation of published content. The infrastructure may support financial transactions. The infrastructure may support electronic currency transfers. The infrastructure may support micro-payments. The infrastructure service may provide quality of service. The infrastructure service may include logging. The infrastructure service may include communications. The infrastructure service may include reporting. The infrastructure service may include a time service. The time service may provide a time. The time service may provide a date.

A secure syndication system may be provided using the security infrastructure service. The secure syndication system may include device-level security. The secure syndication system may include feed-level security. The secure syndication system may include item-level security. The secure syndication system may include field-level security. Field-level security may control access to content within tags of syndicated content. The secure syndication system may include tag-level security. Tag-level security may control access to tags that identify portions of a syndicated item. The secure syndication system may include service-level security. The service-level security may include a secure search facility. The service-level security may include a secure filter facility. The service-level security may include a secure database. The service-level security may include a secure pinger. The service-level security may manage conditional access to content. The service-level security may provide a secure enterprise-wide syndication system. The secure enterprise-wide syndication system may filter syndicated content from outside the enterprise for republication within the enterprise. The secure enterprise-wide syndication system may include a secure publication feed and an unsecured publication feed. The secure publication feed may be provided exclusively to authorized users. The unsecured publication feed may offer subscription to the public. The secure syndication system may include a password facility controlling access to data within an item of syndicated content. The secure syndication system may include an encryption facility for one or more of a field within an item of syndicated content and a feed of syndicated content items.

In one aspect, the system may include an electronic commerce service. The electronic commerce service may include a purchasing service. The electronic commerce service may include an advertising service. The electronic service may include an auction service. The electronic commerce service may include a product review service. The electronic commerce service may support the sale of goods or the sale of services. The electronic commerce service may include a discussion group service. The electronic commerce service may include a discussion group service. The electronic commerce service may include an auction service.

The system disclosed herein may include combinations of the foregoing services and/or layers, including the alternative embodiments thereof identified above. The system may include a syndication service, a semantic service, and a data service. The system may include a syndication service, a semantic service and a processing service. The system may include a syndication service, a semantic service and an application layer. The system may include a syndication service, a semantic service, and an infrastructure service. The system may include a syndication service, a data service and a processing service. The system may include a syndication service, a data service and an application layer. The system may include a syndication service, a data service and an infrastructure service. The system may include a syndication service, a processing service, and an application layer. The system may include a syndication service a processing service, and an infrastructure service. The system may include a syndication service, an application service and an infrastructure service. The system may include a semantic service, a data service, and a processing service. The system may include a semantic service, a data service and an application layer. The system may include a semantic service, a data service, and an infrastructure service. The system may include a semantic service, a processing service, and an application layer. The system may include a semantic service, a processing service, and an infrastructure service. The system may include a semantic service, an application layer, and an infrastructure service. The system may include a data service, a processing service, and an application layer. The system may include a data service, a processing service and an infrastructure service. The system may include a data service, an application service, and an infrastructure service. The system may include a processing service, an application service, and an infrastructure service.

The processing service may include any of the processing services identified above. The data service may include any of the data services described above. The infrastructure service may include any of the infrastructure services described above. The syndication service may include any of the syndication services described above. The application layer may include any of the application layers described above.

Each aspect of the foregoing may be embodied in one or more of a client-side application, a server-side application, one or more semiconductor devices, a computer program product embodied in a computer readable medium, a web service, a services-oriented architecture service, an applet, or an application, either alone or in combination. Further, each of the foregoing systems may also, or instead, be embodied in a method, or in a computer program product embodied in a computer readable medium the, when executing on one or more computers, performs the steps of such a method.

The terms "feed", "data feed", "data stream" and the like, as well as the S-definition described further below, as used herein, are intended to refer interchangeably to syndicated data feeds and/or descriptions of such feeds. While RSS is one popular example of a syndicated data feed, any other source of news or other items may be used with the systems described herein, such as the outlining markup language, OPML, and these terms should be given the broadest possible meaning unless a narrow sense is explicitly provided or clear from the context. Similarly, terms such as "item", "news item", and "post", as well as the S-messages described further below, are intended to refer to items within a data feed, and may contain text and/or binary data encoding any digital media including still or moving images, audio, application-specific file formats, and so on.

The term "syndication" is intended to refer to publication, republication, or other distribution of content using any suitable technology, including RSS and any extensions or modifications thereto, as well as any other publish-subscribe or similar technology that may be suitably adapted to the methods and systems described herein. "Syndicated" is intended to describe content in syndication.

BRIEF DESCRIPTION OF THE FIGURES

The foregoing and other objects and advantages of the invention will be appreciated more fully from the following further description thereof, with reference to the accompanying drawings, wherein:

FIG. 8 shows a user interface for a syndication system.

FIGS. 16-24 show entities and atomic operations in a syndication system.

FIG. 25 shows an example of a syndication message.

FIG. 26 shows an example of a syndication message.

FIG. 29 shows communication of remote sites with a central processing facility.

FIG. 30 shows use of computing services in electronic commerce.

DETAILED DESCRIPTION

Various embodiments of the present invention are described below, including certain embodiments relating particularly to RSS feeds and other syndicated data streams. It should be appreciated, however, that the present invention is not limited to any particular protocol for data feeds, and that the various embodiments discussed explicitly herein are primarily for purposes of illustration. Thus, the term syndication generally, and references to RSS specifically, should be understood to include, for example, RDF, RSS v 0.90, 0.91, 0.9x, 1.0, and 2.0, variously attributable to Netscape, UserLand Software, and other individuals and organizations, as well as Atom from the AtomEnabled Alliance, and any other similar formats, as well as non-conventional syndication formats that can be adapted for syndication, such as OPML. Still more generally, while RSS technology is described, and RSS terminology is used extensively throughout, it will be appreciated that the various concepts discussed herein may be usefully employed in a variety other contexts. For example, various privacy and identity techniques described herein could be usefully combined with HTML Web content, rather than RSS-based XML data. Similarly, some of the branding and advertising techniques described herein may be usefully combined with list servers, bulletin boards, or other Internet news sources. Thus, it will be understood that the embodiments described herein are provided by way of example only, and are not intended to limit the scope of the inventive concepts disclosed herein.

Figure 1:
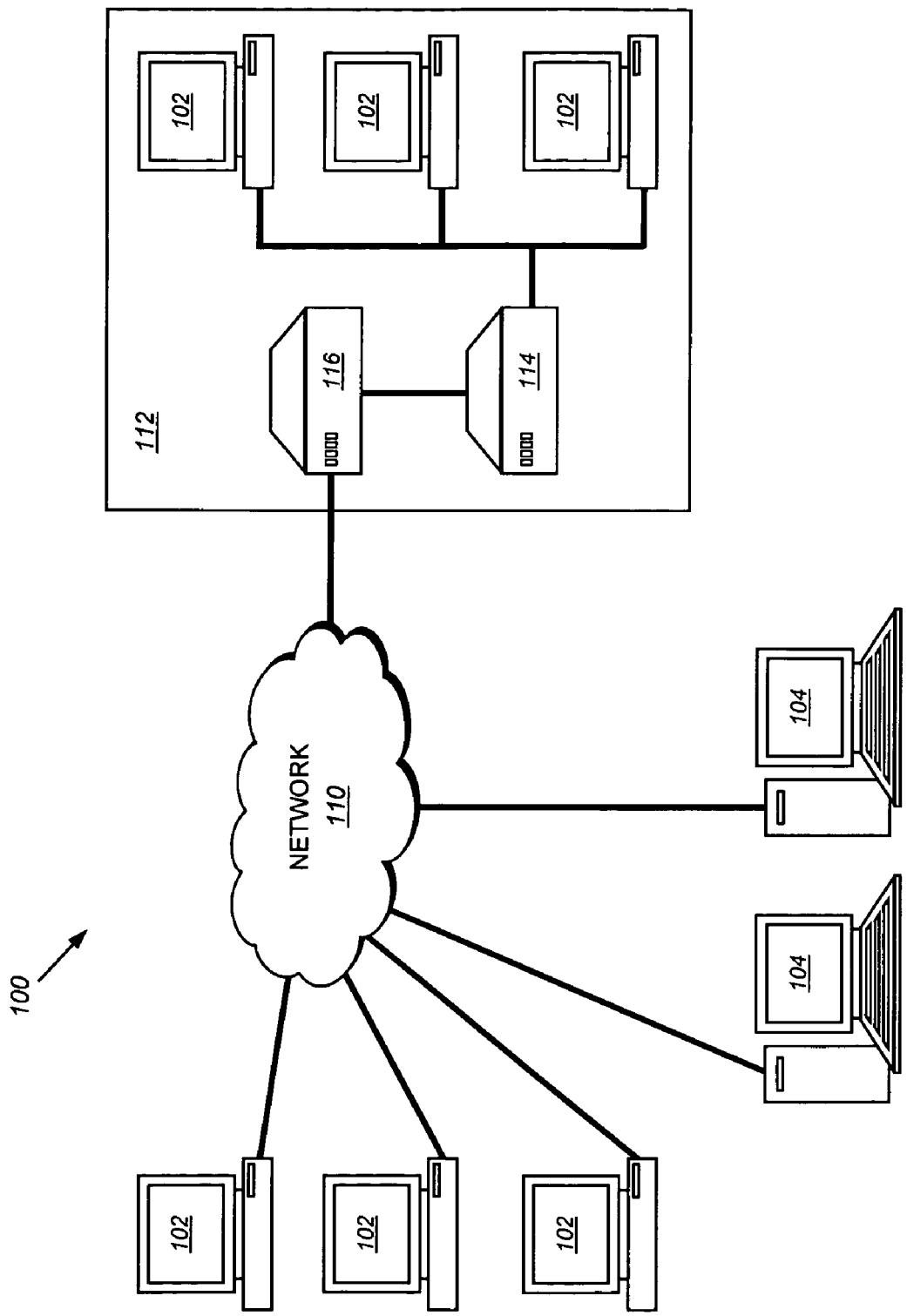
FIG. 1 shows a network that may be used with the systems described herein.

FIG. 1 shows a network for providing a syndicated data stream such as an RSS stream. Short for Really Simple Syndication, RDF (Resource Description Framework) Site Summary or Rich Site Summary, RSS is an XML format for syndicating Web content. A Web site operator that wants to allow other sites to publish some of the Web site's content may create an RSS document and register the document with an RSS publisher. The published or "syndicated" content can then be presented on a different site, or through an aggregator or other system, directly at a client device. Syndicated content may include such data as news feeds, events listings, news stories, headlines, project updates, and excerpts from discussion forums or even corporate information. While RSS content often includes text, other data may also be syndicated, typically in binary form, such as images, audio, and so forth. The systems described herein may use all such forms of data feed. In one embodiment, the XML/RSS feed itself may be converted to binary in order to conserve communications bandwidth. This may employ, for example, Microsoft's DINE specification for binary information, or any other suitable binary format.

As shown in FIG. 1, a network 100 may include a plurality of clients 102 and servers 104 connected via an internetwork 110. Any number of clients 102 and servers 104 may participate in such a system 100. The system may further include one or more local area networks ("LAN") 112 interconnecting clients 102 through a hub 114 (in, for example, a peer network such as a wired or wireless Ethernet network) or a local area network server 114 (in, for example, a client-server network). The LAN 112 may be connected to the internetwork 110 through a gateway 116, which provides security to the LAN 112 and ensures operating compatibility between the LAN 112 and the internetwork 110. Any data network may be used as the internetwork 110 and the LAN 112.

In one aspect of the systems described herein, a device within the internetwork 110 such as a router or, on an enterprise level, a gateway or other network edge or switching device, may cache popular data feeds to reduce redundant traffic through the internetwork 110. In other network enhancements, clients 102 may be enlisted to coordinate sharing of data feeds using techniques such as those employed in a BitTorrent peer-to-peer network. In the systems described herein, these and other techniques may be generally employed to improve performance of an RSS or other data feed network.

In one embodiment, the internetwork 110 is the Internet, and the World Wide Web provides a system for interconnecting clients 102 and servers 104 in a communicating relationship through the Internet 110. The internetwork 110 may also, or instead, includes a cable network, and at least one of the clients 102 may be a set-top box, cable-ready game console, or the like. The internetwork 110 may include other networks, such as satellite networks, the Public Switched-Telephone Network, WiFi networks, WiMax networks, cellular networks, and any other public, private, or dedicated networks that might be used to interconnect devices for transfer of data.

An exemplary client 102 may include a processor, a memory (e.g. RAM), a bus which couples the processor and the memory, a mass storage device (e.g. a magnetic hard disk or an optical storage disk) coupled to the processor and the memory through an I/O controller, and a network interface coupled to the processor and the memory, such as modem, digital subscriber line ("DSL") card, cable modem, network interface card, wireless network card, or other interface device capable of wired, fiber optic, or wireless data communications. One example of such a client 102 is a personal computer equipped with an operating system such as Microsoft Windows XP, UNIX, or Linux, along with software support for Internet communication protocols. The personal computer may also include a browser program, such as Microsoft Internet Explorer, Netscape Navigator, or FireFox to provide a user interface for access to the internetwork 110. Although the personal computer is a typical client 102, the client 102 may also be a workstation, mobile computer, Web phone, VOIP device, television set-top box, interactive kiosk, personal digital assistant, wireless electronic mail device, or other device capable of communicating over the Internet. As used herein, the term "client" is intended to refer to any of the above-described clients 102 or other client devices, and the term "browser" is intended to refer to any of the above browser programs or other software or firmware providing a user interface for navigating an internetwork 110 such as the Internet.

An exemplary server 104 includes a processor, a memory (e.g. RAM), a bus which couples the processor and the memory, a mass storage device (e.g. a magnetic or optical disk) coupled to the processor and the memory through an I/O controller, and a network interface coupled to the processor and the memory. Servers may be clustered together to handle more client traffic, and may include separate servers for different functions such as a database server, an application server, and a Web presentation server. Such servers may further include one or more mass storage devices such as a disk farm or a redundant array of independent disk ("RAID") system for additional storage and data integrity. Read-only devices, such as compact disk drives and digital versatile disk drives, may also be connected to the servers. Suitable servers and mass storage devices are manufactured by, for example, Compaq, IBM, and Sun Microsystems. Generally, a server 104 may operate as a source of content and provide any associated back-end processing, while a client 102 is a consumer of content provided by the server 104. However, it should be appreciated that many of the devices described above may be configured to respond to remote requests, thus operating as a server, and the devices described as servers 104 may operate as clients of remote data sources. In contemporary peer-to-peer networks and environments such as RSS environments, the distinction between clients and servers blurs. Accordingly, as used herein, the term "server" as used herein is generally intended to refer to any of the above-described servers 104, or any other device that may be used to provide content such as RSS feeds in a networked environment.

Focusing now on the internetwork 110, one embodiment is the Internet. The structure of the Internet 10 is well known to those of ordinary skill in the art and includes a network backbone with networks branching from the backbone. These branches, in turn, have networks branching from them, and so on. The backbone and branches are connected by routers, bridges, switches, and other switching elements that operate to direct data through the internetwork 110. For a more detailed description of the structure and operation of the Internet 110, one may refer to "The Internet Complete Reference," by Harley Hahn and Rick Stout, published by McGraw-Hill, 1994. However, one may practice the present invention on a wide variety of communication networks. For example, the internetwork 110 can include interactive television networks, telephone networks, wireless voice or data transmission systems, two-way cable systems, customized computer networks, Asynchronous Transfer Mode networks, and so on. Clients 102 may access the internetwork 10 through an Internet Service Provider ("ISP", not shown) or through a dedicated DSL service, ISDN leased lines, T1 lines, OC3 lines, digital satellite service, cable modem service, or any other connection, or through an ISP providing same.

In its present deployment as the Internet, the internetwork 110 includes a worldwide computer network that communicates using the well-defined Transmission Control Protocol ("TCP") and Internet Protocol ("IP") to provide transport and network services. Computer systems that are directly connected to the Internet 110 each have a unique IP address. The IP address consists of four one-byte numbers (although a planned expansion to sixteen bytes is underway with IPv6). To simplify Internet addressing, the Domain Name System ("DNS") was created. The DNS allows users to access Internet resources with a simpler alphanumeric naming system. A DNS name consists of a series of alphanumeric names separated by periods. When a domain name is used, the computer accesses a DNS server to obtain the explicit four-byte IP address. It will be appreciated that other internetworks 10 may be used with the invention. For example, the internetwork 110 may be a wide-area network, a local area network, a campus area network, or corporate area network. The internetwork 110 may be any other network used to communicate data, such as a cable broadcast network. To further define the resources on the Internet 110, the Uniform Resource Locator system was created. A Uniform Resource Locator ("URL") is a descriptor that specifically defines a protocol for an Internet resource along with its location.

URLs have the following format:

protocol://domain.address/path-name where protocol defines the type of protocol used to access the Internet resource. It will be appreciated that, in the context of this paragraph, the term "resource" is used in the conventional sense of the Internet Engineering Task Force's RFC 1738 (December 1994) (updated by RFC 1808, RFC 2368, RFC 2396, and RFC 3986, and obsoleted by RFC 4248 and RFC 4266) to refer to a document, image, or the like available on the Web. Web documents are identified by the protocol "http" which indicates that the hypertext transfer protocol should be used to access the document. Other common protocols include "ftp" (file transmission protocol), "mailto" (send electronic mail), "file" (local file), and "telnet." The domain.address defines the domain name address of the computer that the resource is located on. Finally, the path-name defines a directory path within the file system of the server that identifies the resource. As used herein, the term "IP address" is intended to refer to the four-byte Internet Protocol address (or the expanded address provided by IPv6), and the term "Web address" is intended to refer to a domain name address, along with any resource identifier and path name appropriate to identify a particular Web resource. The term "address," when used alone, may refer to either a Web address or an IP address.

In an exemplary embodiment, a browser, executing on one of the clients 102, retrieves a Web document at an address from one of the servers 104 via the internetwork 110, and displays the Web document on a viewing device, e.g., a screen. A user can retrieve and view the Web document by entering, or selecting a link to, a URL in the browser. The browser then sends an http request to the server 104 that has the Web document associated with the URL. The server 104 responds to the http request by sending the requested Web document to the client 102. The Web document is an HTTP object that includes plain text (ASCII) conforming to the HyperText Markup Language ("HTML"). Other markup languages are known and may be used on appropriately enabled browsers and servers, including the Dynamic HyperText Markup Language ("DHTML"), the Extensible Markup Language ("XML"), the Extensible Hypertext Markup Language ("XHTML"), and the Standard Generalized Markup Language ("SGML").

Each Web document usually contains hyperlinks to other Web documents. The browser displays the Web document on the screen for the user and the hyperlinks to other Web documents are emphasized in some fashion such that the user can identify and select each hyperlink. To enhance functionality, a server 104 may execute programs associated with Web documents using programming or scripting languages, such as Perl, C, C++, C#, or Java, or a Common Gateway Interface ("CGI") script to access applications on the server. A server 104 may also use server-side scripting languages such as ColdFusion from MacroMedia or PHP. These programs and languages may perform "back-end" functions such as order processing, database management, and content searching. A Web document may also contain, or include references to, small client-side applications, or applets, that are transferred from the server 104 to the client 102 along with a Web document and executed locally by the client 102. Java is one popular example of a programming language used for applets. The text within a Web document may further include (non-displayed) scripts that are executable by an appropriately enabled browser, using a scripting language such as JavaScript or Visual Basic Script. Browsers may further be enhanced with a variety of helper applications to interpret various media including still image formats such as JPEG and GIF, document formats such as PS and PDF, motion picture formats such as AVI and MPEG, animated media such as Flash media, and sound formats such as MP3 and MIDI. These media formats, along with a growing variety of proprietary media formats, may be used to enrich a user's interactive and audio-visual experience as each Web document is presented through the browser. The term "page" as used herein is intended to refer to the Web document described above, as well as any of the above-described functional or multimedia content associated with the Web document.

In general operation, a server 104 may provide a data stream to a client 102. In an exemplary embodiment, the data stream may be a syndicated data stream such as RSS, an XML grammar for sharing data through the Web. An RSS-enabled server may include an RSS file with a title and description of items to be syndicated. As with simple HTML documents, the RSS file may be hand-coded or computer-generated. The first line of an RSS file may contain an XML declaration of the form:

<?xml version="1.0"?>

While not strictly required, this declaration may improve version compatibility. The next item in an RSS file may be a Document Type Declaration ("DTD") that identifies the file as an RSS document:

<!DOCTYPE rss PUBLIC "-//Netscape Communications//DTD RSS 0.91//EN"
"http://my.netscape.com/publish/formats/rss-0.91.dtd">

The RSS element is the root or top-level element of an RSS file. The RSS element must specify the version attribute (in this example, version 0.91). It may also contain an encoding attribute (the default is UTF-8):

<rss version="0.91" encoding="ISO-8859-1">

The root element is the top-level element that contains the rest of an XML document. An RSS element may contain a channel with a title (the name of the channel), description (short description of the channel), link (HTML link to the channel Web site), language (language encoding of the channel, such as en-us for U.S. English), and one or more item elements. A channel may also contain the following optional elements:

rating—an independent content rating, such as a PICS rating
copyright—copyright notice information
pubDate—date the channel was published
lastBuildDate—date the RSS was last updated
docs—additional information about the channel
managingEditor—channel's managing editor
webMaster—channel Webmaster
image—channel image
textinput—allows a user to send an HTML form text input string to a URL
skiphours—the hours that an aggregator should not collect the RSS file
skipDays—the weekdays that an aggregator should not collect the RSS file A channel may contain an image or logo. In RSS, the image element contains the image title and the URL of the image itself. The image element may also include the following optional elements: a link (a URL that the image links to), a width, a height, and a description (additional text displayed with the image). There may also be a text input element for an HTML text field. The text input element may include a title (label for a submit button), description, name, and link (to send input). The link may enable richer functionality, such as allowing a user to submit search terms, send electronic mail, or perform any other text-based function.

Once defined in this manner, a channel may contain a number of items, although some services (e.g., Netscape Netcenter) may limit the number. In general, the "item" elements provide headlines and summaries of the content to be shared. New items may be added, either manually or automatically (such as through a script) by appending them to the RSS file.

Figure 2:
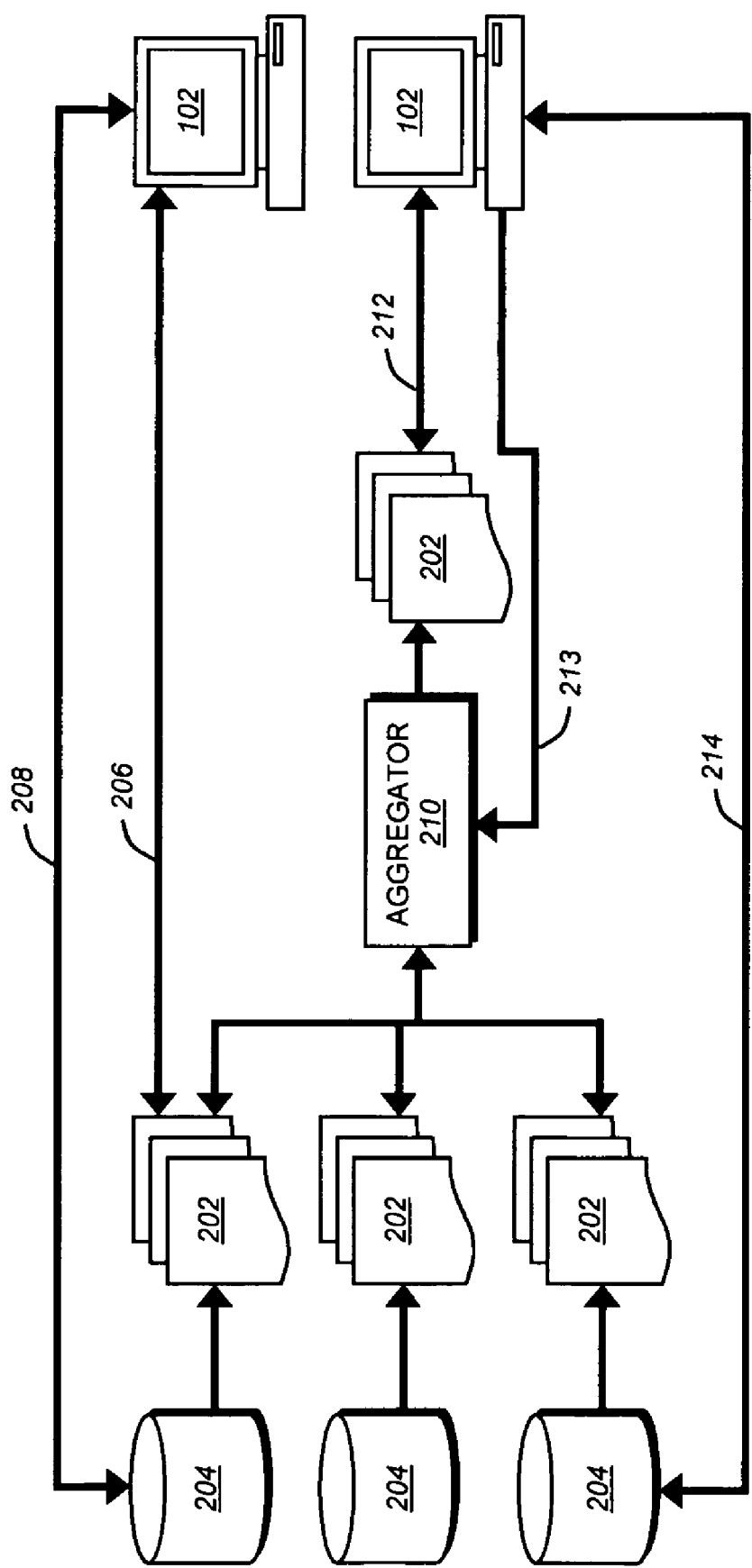
FIG. 2 shows a system for using and aggregating data feeds.

FIG. 2 depicts a system for using and aggregating data feeds or other syndicated content. In general, data feeds 202, such as RSS source files, are generated from a content source 204 and made available for use or review by clients 102 through a network.

The content source 204 may provide any electronic content including newspaper articles, Web magazine articles, academic papers, government documents such as court opinions, administrative rulings, regulation updates, or the like, opinions, editorials, product reviews, movie reviews, financial or market analysis, current events, bulletins, and the like. The content may include text, formatting, layout, graphics, audio files, image files, movie files, word processing files, spreadsheet files, presentation files, electronic documents, HTML files, executable files, scripts, multi-media, relational databases, data from relational databases and/or any other content type or combination of types suitable for syndication through a network. The content source 204 may be any commercial media provider(s) such as a newspapers, news services (e.g., Reuters or Bloomberg), or individual journalists such as syndicated columnists. The content source 204 may also be from commercial entities such as corporations, non-profit corporations, charities, religious organizations, social organizations, or the like, as well as from individuals with no affiliation to any of the foregoing. The content source 204 may be edited, as with news items, or automated, as with data feeds 202 such as stock tickers, sports scores, weather conditions, and so on. While written text is commonly used in data feeds 202, it will be appreciated that any digital media may be binary encoded and included in an item of a data feed 202 such as RSS. For example, data feeds 202 may include audio, moving pictures, still pictures, executable files, application-specific files (e.g., word processing documents or spreadsheets), and the like. It should also be understood that, while a content source 204 may generally be understood as a well defined source of items for a data feed, the content source 204 may be more widely distributed, or subjectively gathered by a user preparing a data feed 202. For example, an individual user interested in automotive mechanics may regularly read a number of related magazines and regularly attend trade shows. This information may be processed on an ad hoc basis by the individual and placed into a data feed 202 for review and use by others. Thus it will be understood that the data stream systems described herein may have broad commercial use, as well as non-commercial, educational, and mixed uses.

As described generally above, the data feed 202 may include, for each item of content, summary information such as a title, synopsis or abstract (or a teaser, for more marketing oriented materials), and a link to the underlying content. Thus as depicted in FIG. 2, when a client 102 accesses a data feed 202, as depicted by an arrow 206, the client 102 may then display the summary information for each item in a user interface. A client 102 may, in response to user input such as clicking on a title of an item in the user interface, retrieve the underlying item from the content source 204 as indicated by an arrow 208. In the bi-directional communication depicted by the arrow 208, the client 102 may also identify the specific data feed 202 through which the item was identified, which may be useful for tracking distribution channels, customer behavior, affiliate referral fees, and so forth. It should be appreciated that an RSS data feed 202 may be presented to a client 102 as an RSS file (in XML format) that the client 102 locally converts to HTML for viewing through a Web browser, or the data feed 202 may be converted to HTML at a Web site that responds to HTTP requests from a client 102 and responds with an HTML-formatted data feed.

A related concept is the so-called "permalink" that provides a permanent URL reference to a source document that may be provided from, for example, a dynamically generated Web site, or a document repository served from a relational database behind a Web server. While there is no official standard for permalink syntax or usage, they are widely used in conjunction with data feeds. Permalinks typically consist of a string of characters which represent the date and time of posting, and some (system dependent) identifier (which includes a base URL, and often identifies the author, subscriber, or department which initially authored the item). If an item is changed, renamed, or moved, its permalink remains unaltered. If an item is deleted altogether, its permalink cannot be reused. Permalinks are exploited in a number of applications including link tracing and link track back in Weblogs, and references to specific Weblog entries in RSS or Atom syndication streams. Permalinks are supported in most modern weblogging and content syndication software systems, including Movable Type, LiveJournal, and Blogger.

RSS provides a standard format for the delivery of content through data feeds. This makes it relatively straightforward for a content provider to distribute content broadly, and for an affiliate to receive and process content from multiple sources. It will be appreciated that other RSS-compliant and/or non-RSS-compliant feeds may be syndicated as that term is used herein, and as described in greater detail below. As noted above, the actual content may not be distributed directly, only the headlines, which means that users will ultimately access the content source 204 if they're interested in a story. It is also possible to distribute the item of content directly through RSS, though this approach may compromise some of the advantages of network efficiency (items are not copied and distributed in their entirety) and referral tracking. Traffic to a Web site that hosts a content source 204 can increase in response to distribution of data feeds 202.

Although not depicted, a single content source 204 may also have multiple data feeds 202. These may be organized topically, or according to target clients 102. Thus, the same content may have data feeds 202 for electronic mailing lists, PDAs, cell phones, and set-top boxes. For example, a content provider may decide to offer headlines in a PDA-friendly format, or create a weekly email newsletter describing what's new on a Web site.

Data feeds 202 in a standard format provide for significant flexibility in how content is organized and distributed. An aggregator 210, for example, may be provided that periodically updates data from a plurality of data feeds 202. In general, an aggregator 210 may make many data feeds 202 available as a single source. As a significant advantage, this intermediate point in the content distribution chain may also be used to customize feeds and presentation thereof, as well as to filter items within feeds and provide any other administrative services to assist with syndication, distribution, and review of content.

As will be described in greater detail below, the aggregator 210 may filter, prioritize or otherwise process the aggregated data feeds. A single processed data feed 202 may then be provided to a client 102 as depicted by an arrow 212. The client 102 may request periodic updates from the data feed 202 created by the aggregator 210, as also indicated by an arrow 212. As indicated by an arrow 213, the client 102 may also configure the aggregator 210 such as by adding data streams 202, removing data streams 202, searching for new data streams 202, explicitly filtering or prioritizing items from the data streams 202, or designating personal preferences or profile data that the aggregator 210 may apply to generate the aggregated data feed 202. When an item of interest is presented in the user interface of the client 102, a user may select a link to the item causing the client 102 to retrieve the item from the associated content source 204, as indicated by an arrow 214. The aggregator 210 may present the data feed 202 as a static web page that is updated only upon an explicit request from the client 102, or the aggregator 210 may push updates to a client 102 using either HTTP or related Web browser technologies, or by updates through some other channel, such as e-mail updates. It will also be appreciated that, while the aggregator 210 is illustrated as separate from the client 102, the aggregator 210 may be realized as a primarily client-side technology, where software executing on the client 102 assumes responsibility for directly accessing a number of data feeds 202 and aggregating/filtering results from those feeds 202.

It will be appreciated that a user search for feeds will be improved by the availability of well organized databases. While a number of Weblogs provide local search functionality, and a number of aggregator services provide lists of available data feeds, there remains a need for a consumer-level searchable database of feed content. As such, one aspect of the system described herein is a database of data feeds that is searchable by contents as well as metadata such as title and description. In a server used with the systems described herein, the entire universe of known data feeds may be hashed or otherwise organized into searchable form in real time or near real time. The hash index may include each word or other symbol and any data necessary to locate it in a stream and in a post.

The advent of commonly available data feeds 202, such as RSS feeds, along with tools such as aggregators 210, enables new modes of communication. In one common use, a user may, through a client 102, post aggregated feeds 202 to a Weblog. The information posted on a Weblog may include an aggregated feed 202, one or more data feeds 202 that are sources for the aggregated feed 202, and any personal, political, technical, or editorial comments that are significant to the author. As such, all participants in an RSS network may become authors or sources of content, as well as consumers.

Figure 3:
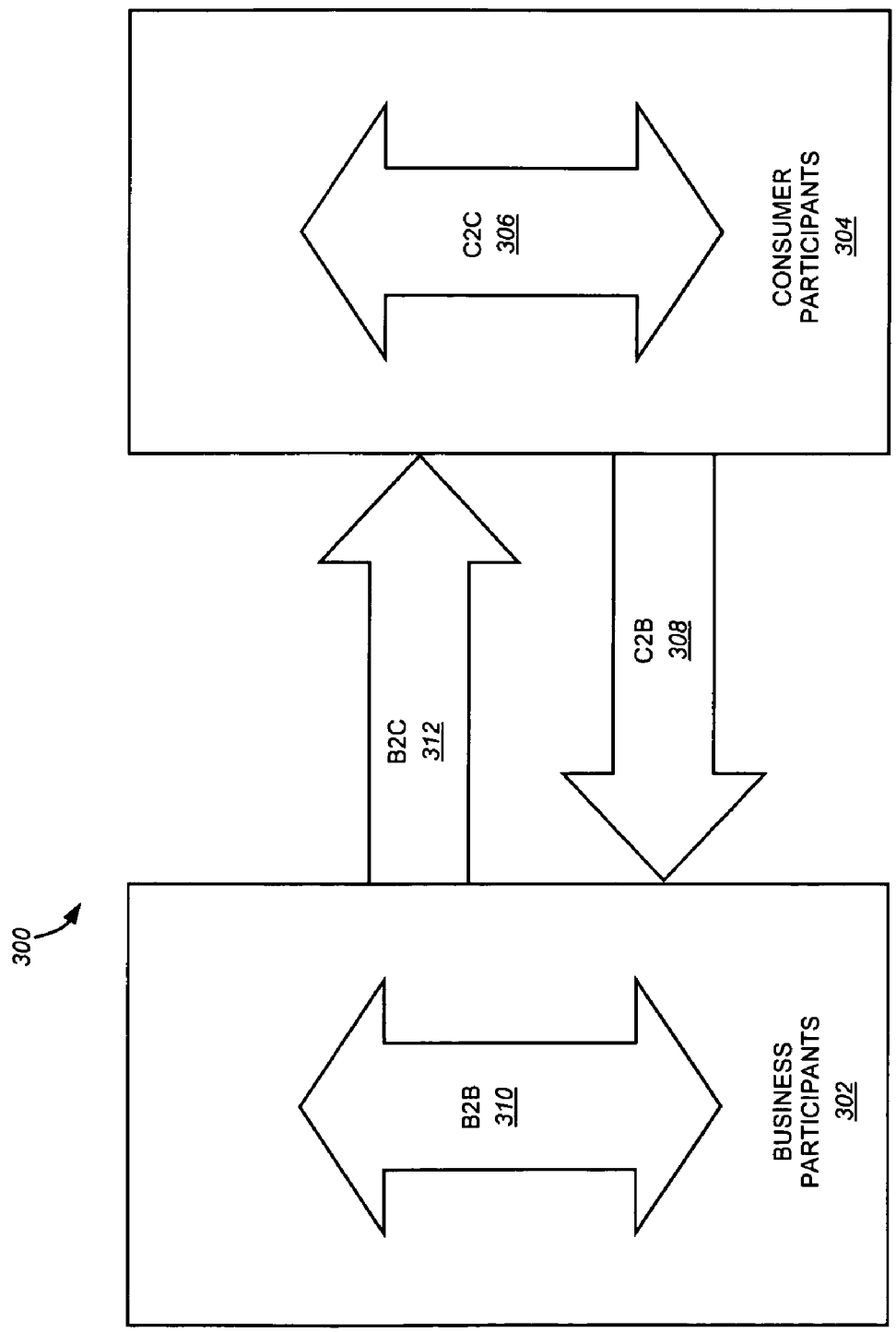
FIG. 3 depicts markets for syndicated content.

FIG. 3 depicts certain aspects of the markets for data feeds. This generally depicts characteristics that can be present in a number of different markets in which the systems described herein may be usefully deployed. Market 300 for data feeds 302 such as RSS may be understood as including four main models for information exchange among business participants in the commercial space 302 and individuals in the consumer space 304. As large, established companies such as Yahoo, Google, and Microsoft adopt and integrate RSS technologies, these markets should grow significantly.

At present, the consumer-to-consumer market model 306 consists primarily of millions of individual bloggers, mostly communicating with each other. This includes non-commercial Weblogs where individuals aggregate data feeds 302 from a variety of sources, and include editorial commentary or other information. In general, a source in this space is an individual presenting aggregated feeds 302 in a Web site with some common theme or themes of interest to the author, such as history, sports, science, technology, politics, literature, art, music, and so forth. However, there are no strict requirements that any one or more themes be followed, and the Weblog may simply reflect an ad hoc selection of topics that the author finds interesting. Weblogs in this space gain popularity according to the content provided, with readership (and associated RSS subscriptions or registrations) rising or falling according to general interest.

The consumer-to-business model or segment 308 brings together consumers who are interested in a particular topic, typically a topic with a corresponding commercial market, such as automobiles, mortgages, financial services, home repair, hobbies, and the like. A topic may be still more refined, such as antique automobiles, or antique American automobiles; however, the corresponding participation of commercial participants may depend on the scope of the market. Thus, a large number of financial service providers could be expected to subscribe to an RSS data feed for general consumers of financial services, however, a smaller number of commercial subscribers might be expected for derivative currency hedge instruments among Pacific Rim country currencies. In general, consumer-to-business uses may provide consumers with concerns, interests, and preferences in a particular market with a forum that will be followed by corresponding commercial interests. In addition, by participating in this RSS network, businesses may also address consumer interests in a more direct and personal way, as distinguished from the business-to-consumer segment 312 discussed below. At the same time, it will be appreciated that the distinction between these segments 308, 312 need not be an absolute one, and a synthesis of these two communication channels may result in a greater dialogue between commercial and individual actors, to their collective and mutual benefit. Thus, for example, with a suitable configured aggregated feed 302 and associated Web presentation, an automobile manufacture could design a new minivan or SUV in cooperation with the automobile-buying public in a manner that addresses previously unknown purchasing preferences of consumers. Additionally, since the community of participants is likely to be highly focused, this segment 308 may offer significant opportunities for revenue from targeted advertising.

The business-to-business segment 310 does not appear to be commonly used, although in the methods and systems described herein blogs and other RSS media, along with suitable security and identity features discussed below, may substitute for much of email and other forms of corporate and business-to-business communication, such as time management, inventory, supply chain, manufacturing, and customer relations information flow.

The business-to-consumer segment 312 includes an extension of traditional media companies that can add data feed capabilities to their online presence. This includes news companies in print media, radio, television media, and Internet media, including, by way of example and not limitation, the New York Times, the Washington Post, the Wall Street Journal, Forbes, Time, Business Week, CSPAN, ESPN, The Weather Channel, CNBC, CNET, Bloomberg, Reuters, and so on. This may also include non-news related media that nonetheless periodically updates content, such as movie studios, network television, cable television, and so on. In addition, other companies that serve consumers are may also usefully employ data feed systems, including companies ranging from catalogue companies such as Land's End to consumer electronics retailer Best Buy. In this context, the RSS platform offers a reliable distribution channel for advertising new products and special offers to presumably interested consumers. These and other applications may be realized using the data feed technology described herein.

All such entity-to-entity communications described above may be improved through enhanced syndication systems as generally described herein. It will be appreciated that one obstacle to expanded use across all of these markets is the absence in the primary technology, RSS, of enterprise-class features such as security, authentication, conditional access data repositories, and rich metadata, to name a few. In one aspect, the systems described herein bring many of these features to RSS-like systems to provide secure, scalable syndication systems.

It should be clear that, while the term "aggregator" is used to label aspects of the systems disclosed herein, those systems include significant useful and advantageous functionality that is not present in any aggregator in the prior art, and as such the term should be interpreted broadly to optionally include all of the functions and techniques described below, rather than narrowly in the sense that it is currently used in the art. Although broader in meaning, the aggregator and interface described below may operate, for example, from one of the servers 104 described above with reference to FIG. 1, and may cooperate with other participants and content sources in the manner depicted for the aggregator 210 described in FIG. 2.

It will be appreciated that the components described herein correspond generally to various areas of functionality for a data feed system. However, in various embodiments, other components may be added, or certain components may be removed or combined with other components. For example, the aggregator described herein may cooperate with an n-tier architecture for a more general purpose Web server, or with a relational database or other back end systems not specifically depicted herein to store and access data. Similarly, the systems described herein may include FTP servers, e-mail servers, PSTN interfaces, and other physical connections and protocols for various other functions that may be usefully combined with the aggregator to enhance functionality. Any number of such combinations and variations may be employed consistent with the systems described herein, and are intended to fall with the scope of the present disclosure.

It will also be appreciated that a wide range of software and hardware platforms may be used to deploy the systems described herein. Generally, the system components may be realized in hardware, software, or some combination of these. The components may be realized in one or more microprocessors, microcontrollers, embedded microcontrollers, programmable digital signal processors or other programmable device, along with internal and/or external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. The components may also, or instead, include one or more application specific integrated circuits (ASICs), dedicated semiconductor devices, programmable gate arrays, programmable array logic devices, or any other device that may be configured to process electronic signals.

Any combination of the above circuits and components, whether packaged discretely, as a chip, as a chip set, or as a die, may be suitably adapted to use with the systems described herein. It will further be appreciated that the above components may be realized as computer executable code created using a structured programming language such as C, an object oriented programming language such as C++, or any other high-level or low-level programming language that may be compiled or interpreted to run on one of the above devices, as well as heterogeneous combinations of processors, processor architectures, or combinations of different hardware and software.

Figure 4:
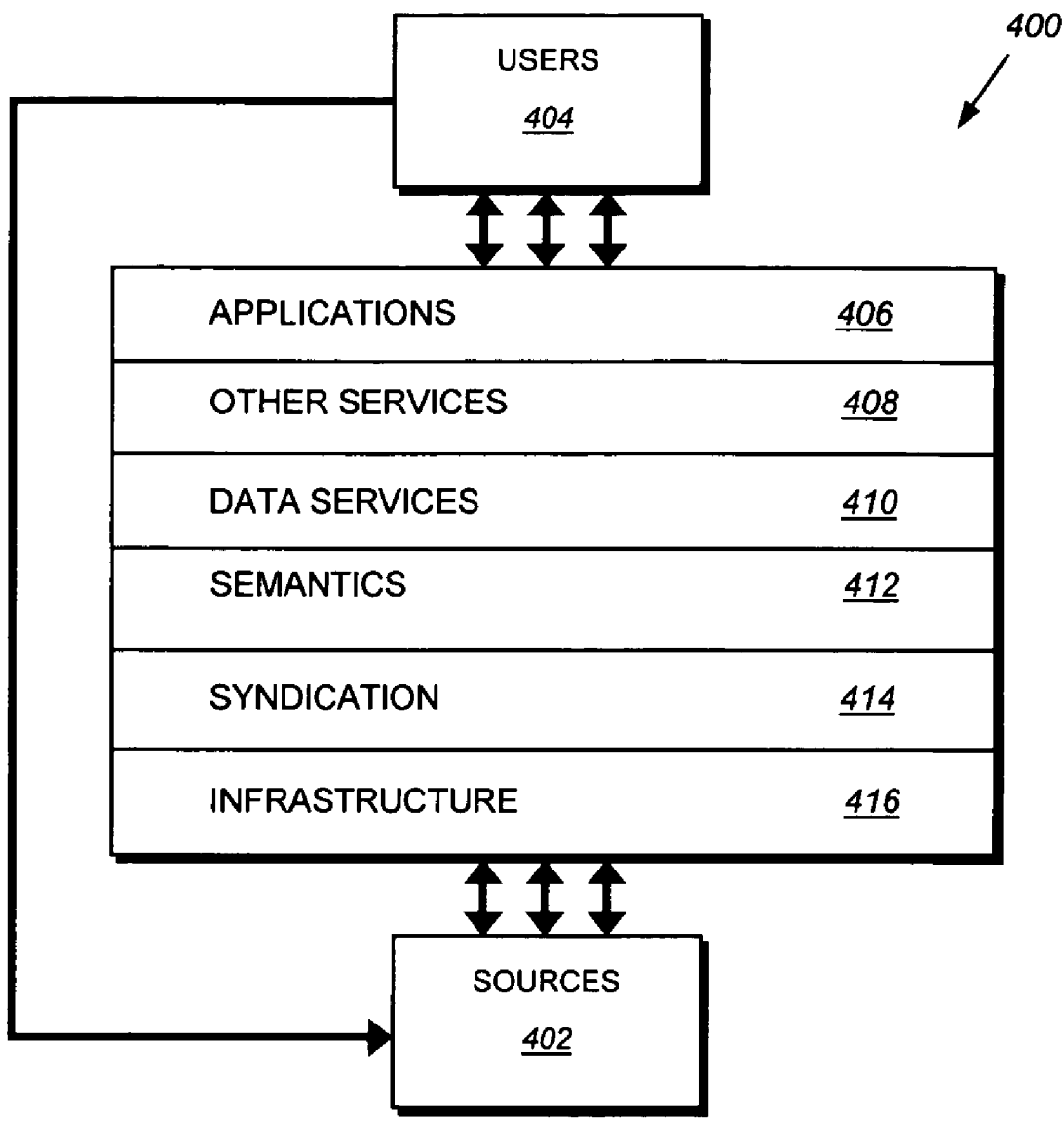
FIG. 4 depicts a conceptual framework for syndicated communications.

FIG. 4 depicts a conceptual framework for syndicated communications. In a syndication system 400, a plurality of sources 402, which may be for example any of the content sources 204 described above, are published to a plurality of users 404, which may be users of any of the clients 102 described above. Users 404 may include individuals, consumers, business entities, government entities, workgroups, and other categories of users 404. Access to the sources 402 by the users 404 may be through layers of devices, services and systems (which may be analogous to or actually embodied in a protocol stack) in which various layers are responsible for discrete functions or services, as depicted generally in FIG. 4. However, it will be appreciated that each layer of FIG. 4 may instead be provided as one or more non-layered services. At the same time, it should be understood that the number, arrangement, and functions of the layers may be varied in a number of ways within a syndication system 400; in particular, depending on the characteristics of the sources, the needs of the users 404 and the features desired for particular applications, a number of improved configurations for syndication systems 404 may be established, representing favorable combinations and sub-combinations of layers depicted in FIG. 4. The layers may provide services such as, for example, services related to applications 406, other services 408 (including relating to processing), services related to data 410, services related to semantics of content 412, syndication services 414, and services related to infrastructure 416. More generally, all of the services and functions described below, either individual or in combinations, as well as other services not specifically mentioned, may be incorporated into an enhanced syndication system as described herein. It should be understood that any of the services depicted in the layers of FIG. 4 may be embodied in hardware, software, firmware, or a combination thereof; for example, a service may be embodied in software as a web service, according to a services oriented architecture. Alternatively, without limitation, a: service may be a client-side or server-side application, or take any of the forms described herein and in the documents incorporated by reference herein. In one embodiment, one or more layers may be embodied in a dedicated semiconductor device, such as an ASIC, that is configured to enable syndication.

Services related to applications 406 may be embodied, for example, in a client-side application (including commercially available applications such as a word processor, spreadsheet, presentation software, database system, task management system, supply chain management system, inventory management system, human resources management system, user interface system, operating system, graphics system, computer game, electronic mail system, calendar system, media player, and the like), a remote application or service, an application layer of an enhanced syndication services protocol stack, a web service, a service oriented architecture service, a Java applet, or a combination of these. Applications 406 may include, for example, a user interface, social networking, vertical market applications, media viewers, transaction processing, alerts, event-action pairs, analysis, and so forth. Applications 406 may also accommodate vertical market uses of other aspects of the system 400 by integrating various aspects of, for example, security, interfaces, databases, syndication, and the like. Example of vertical markets include financial services, health care, electronic commerce, communications, advertising, sales, marketing, supply chain management, retail, accounting, professional services, and so forth. In one aspect, the applications 406 may include social networking tools to support functions such as sharing and pooling of syndicated content, content filters, content sources, content commentary, and the like, as well as formation of groups, affiliations, and the like. Social networking tools may support dynamic creation of communities, and moderation of dialogues within communities, while providing individual participants with any desired level of anonymity. Social networking tools may also, or instead, evaluate popularity of feeds or items in a syndication network, or permit user annotation, evaluation, or categorization. A user interface from the application may also complement other services layers. For example, an application may provide a user interface that interprets semantic content to determine one or more display characteristics for associated items of syndicated content.

Other services 408 may include any other services not specifically identified herein that may be usefully employed within an enhanced syndication system. For example, content from the sources 402 may be formatted for display through a formatting service that interprets various types of data and determines an arrangement and format suitable for display. This may also include services that are specifically identified, which may be modified, enhanced, or adapted to different uses through the other services 408. Other services 408 may support one or more value added services. For example, a security service may provide for secure communications among users, or from users to sources. An identity service may provide verification of user or source identities, such as by reference to a trusted third party. An authentication service may receive user credentials and control access to various sources 402, or other services 408 within the system. A financial transaction service may execute financial transactions among users 404, or between users 404 and sources 402. Any service amenable to computer implementation may be deployed as one or more other services 408, either alone or in combination with services from other elements of the system 400.

Data services 410 may be embodied, for example, in a client-side application, a remote application or service, an application layer of an enhanced syndication services protocol stack, as application services deployed, for example, in the services oriented architecture described below, or a combination of these. Data services 410 may include, for example, include search, query, view, extract, or any other database function. Data services 410 may also, or instead, include data quality functions such as data cleansing, deduplication, and the like. Data services 410 may also, or instead, include transformation functions for transforming data between data repositories, or among presentation formats. Thus for example, data may be transformed from entries in a relational database, or items within an OPML outline, into a presentation format such as MS Word, MS Excel, or MS PowerPoint. Similarly, data may be transformed from a source such as an OPML outline into a structured database. Data services 410 may also, or instead, include syndication-specific functions such as searching of data feeds, or items within data feeds, or filtering items for relevance from within selected feeds, or clustering groups of searches and/or filters for republication as an aggregated and/or filtered content source 402. In one aspect, a data service 410 as described herein provides a repository of historical data feeds, which may be combined with other services for user-configurable publication of aggregated, filtered, and/or annotated feeds. More generally, data services 410 may include any functions associated with data including storing, manipulating retrieving, transforming, verifying, authenticating, formatting, reformatting, tagging, linking, hyperlinking, reporting, viewing, and so forth. A search engine deployed within the data services 410 may permit searching of data feeds or, with a content database as described herein, searching or filtering of content within data feeds from sources 402. Data services 410 may be adapted for use with databases such as commercially available databases from Oracle, Microsoft, IBM, and/or open source databases such as MySQL AB or PostgreSQL.

Semantics 412, or semantic processing, may include any functions or services associated with the meaning of content from the sources 402, and may be embodied, for example, in a client-side application, a remote application or service, an application layer of an enhanced syndication services protocol stack, as application services deployed, for example, in the services oriented architecture described below, or a combination of these. Semantics 412 may include, for example, interrelating content into a knowledge structure using, for example, OPML, adding metadata or enriching current metadata, interpreting or translating content, and so forth. Semantics 412 may also include parsing content, either linguistically for substantive or grammatical analysis, or programmatically for generation of executable events. Semantics 412 may include labeling data feeds and items within feeds, either automatically or manually. This may also include interpretation of labels or other metadata, and automated metadata enrichment. Semantics 412 may also provide a semantic hierarchy for categorizing content according to user-specified constraints, or against a fixed dictionary or knowledge structure. Generally, any function relating to the categorization, interpretation, or labeling of content may be performed within a semantic layer, which may be used for example, by users 404 to interpret content, or by sources 402 to self-identify content. Categorization may be based on one or more factors, such as popularity, explicit user categorization, interpretation or analysis of textual, graphical, or other content, relationship to other items (such as through an outline or other hierarchical description), content type (e.g., file type), content metadata (e.g., author, source, distribution channel, time of publication, etc.) and so forth. Currently available tools for semantic processing include OPML, dictionaries, thesauruses, and metadata tagging. Current tools also include an array of linguistic analysis tools which may be deployed as a semantic service, or used by a semantic service. These and other tools may be employed to evaluate semantic content of an item, including the body and metadata thereof, and to add or modify semantic information accordingly.

It will be understood that, while OPML is one specific outlining grammar, any similar grammar, whether XML-based, ASCII-based, or the like, may be employed, provided it offers a manner for explicitly identifying hierarchies and/or relationships among items within a document and/or among documents. Where the grammar is XML-based, it is referred to herein as an outlining markup language.

Semantics 412 may be deployed, for example, as a semantic service associated with a syndication platform or service. The semantic service may be, for example, a web service, a service in a services oriented architecture, a layer of a protocol stack, a client-side or server-side application, or any of the other technologies described herein, as well as various combinations of these. The semantic service may offer a variety of forms of automated, semi-automated, or manual semantic analysis of items of syndicated content, including feeds or channels that provide such items. The semantic service may operate in one or more ways with syndicated content. In one aspect, the semantic service may operate on metadata within the syndicated content, as generally noted above. The semantic service may also, or instead, store metadata independent from the syndicated content, such as in a database, which may be publicly accessible, or privately used by a value-added semantic service provider or the like. The semantic service may also, or instead specify relationships among items of syndicated content using an outlining service such as OPML. In general, an outlining service, outlining markup language, outlining syntax, or the like, provides a structured grammar for specifying relationships such as hierarchical relationships among items of content. The relationship may, for example, be a tree or other hierarchical structure that may be self-defined by a number of discrete relationships among individual items within the tree. Any number of such outlines may be provided in an outline-based semantic service.

By way of an example of use of a semantic service, a plurality of items of syndicated content, such as news items relating to a corporate entity, may be aggregated for presentation as a data feed. Other content, such as stored data items, may be associated with the data feed using an outline markup language so that an outline provided by the semantic service includes current events relating to a corporate entity, along with timely data from a suitable data source such as stoke quotes, bond prices, or any other financial instrument data (e.g., privately held securities, stock options, futures contracts), along with publicly available data such as SEC filings including quarterly reports, annual reports, or other event reports. All of these data sources may be collected for a company using an outline that structures the aggregated data and provides pointers to a current source of data where the data might change (such as stock quotes or SEC filings). Thus an outline may provide a fixed, structured, and current view of the corporate entity where data from different sources changes with widely varying frequencies. Of course other content, such as message boards, discussion groups and the like may be incorporated into the outline, along with relatively stable content such as a web site URL for the entity.

Syndication 414 may include any functions or services associated with a publish-subscribe environment, and may be embodied, for example, in a client-side application, a remote application or service, an application layer of an enhanced syndication services protocol stack, as application services deployed, for example, in the services oriented architecture described below, or a combination of these. Syndication 412 may include syndication specific functions such publication, subscription, aggregation, republication, and more generally, management of syndication information (e.g., source, date, author, and the like). One commonly employed syndication system is RSS, although it will be appreciated from the remaining disclosure that a wide array of enhanced syndication services may provided in cooperation with, or separate from, an RSS infrastructure.

Infrastructure 416 may include any low level functions associated with enhanced syndication services, and may be embodied, for example, in a client-side application, a remote application or service, an application layer of an enhanced syndication services protocol stack, as application services deployed, for example, in the services oriented architecture described below, or a combination of these. Infrastructure 416 may support, for example, security, authentication, traffic management, logging, pinging, communications, reporting, time and date services and the like.

In one embodiment, the infrastructure 416 may include a communications interface adapted for wireless delivery of RSS content. RSS content is typically developed for viewing by a conventional, full-sized computer screen; however, users increasingly view web content, including RSS feeds, using wireless devices, such as cellular phones, Personal Digital Assistants ("PDAs"), wireless electronic mail devices such as Blackberrys, and the like. In many cases content that is suitable for a normal computer screen is not appropriate for a small screen; for example, the amount of text that can be read on the screen is reduced. Accordingly, embodiments of the invention include formatting RSS feeds for wireless devices. In particular, embodiments of the invention include methods and systems for providing content to a user, including taking a feed of RSS content, determining a user interface format for a wireless device, and reformatting the RSS content for the user interface for the wireless device. In embodiments the content may be dynamically reformatted based on the type of wireless device.

In embodiments, tags from an RSS feed can be used to feed a template, such as an XML-enabled template, that further modifies the RSS feed based on the nature of a wireless device. For example, the abstract of an RSS feed can be delivered in a shortened format, such as identifying and delivering the first sentence of the abstract. An RSS feed can also be broken up into sub-segments, and a user can be provided with a link within the feed for requesting additional sub-segments, or additional portions of the feed, thus permitting a user to control content delivery where, for example, the user has a bandwidth-constrained or display-constrained device. In embodiments the link may be interactive, and may be activated or manipulated by a user with a control such as a button, thumbpad, touchscreen, dial button, or stylus.

In embodiments an RSS feed may further comprise inserting a phone number into the feed, wherein interacting with the phone number on a cellular phone or other telecommunications-capable device initiates a telephone call. The telephone call could be to a content source, such as to allow a user to hear a voice rendition of the content of the RSS feed, to hear related content, such as programming related to the RSS feed, to initiate a transaction, such as related to the content of the RSS feed, to request a particular type of additional information, to allow the user to subscribe to the feed, or the like.

In embodiments the RSS feed may include a time-related component, such as a schedule for the delivery of additional content. In embodiments the time-related component may be fed to a calendar, task list, or related facility, thus setting an appointment related to the time-related component in a user's electronic calendar, such as on a handheld device, or on a conventional personal computer or laptop computer.

In embodiments an RSS feed may be provided with a separate layer of security that is associated with a security facility of a wireless device. For example, an RSS feed may be encrypted so that it may only be read by a specific type of wireless device, a specific wireless device, or on a specific wireless device only after entry of a password that is issued to a known user of that wireless device. In embodiments security may be associated with a location facility of the wireless device (such as GPS, cellular triangulation, or the like), such as to allow a user to access an RSS feed only if the user is physically located in a particular place. For example, a user attending a live concert or other event might be permitted to view an RSS feed about the concert, but other users might be excluded from that content, creating a secure new media channel for event attendees.

In embodiments a user interface for a wireless or handheld device may be customized to include menus that specifically relate to RSS content. For example, an interface may be provided with a separate RSS menu icon, drop down selection or the like for allowing a user to place such a device in an RSS mode. Within an RSS mode, initiated by an RSS menu option, a user may be provided with options to take actions related to RSS, such as subscribing to feeds, selecting feeds from a set of feeds, prioritizing feeds, selecting feeds as favorites, or the like. In embodiments, an RSS mode may include a menu item for each of (or a subset of) the components of the RSS schema. For example, a menu icon, drop down item, or the like may allow a user to select and view the title of an RSS feed, the abstract, text, the authors, or other content. In embodiments the user interface of a wireless or handheld device may have an RSS search icon, menu or screen that returns RSS results in response to entry of a keyword. In embodiments results may be returned that include commercial and non-commercial result sets, which may be distinguished on the screen, such as by screen location, by an icon that identifies them as such, or by another indicator of the distinction, such as color, font, underlining, italics, boldface type, highlighting, or the like.

Thus, in embodiments an RSS-customized user interface for a wireless handheld device is provided.

In another aspect, the infrastructure 416 may include improved pinging systems. The only current form of network service in an RSS environment is a primitive system of "pings", such as those provided by weblogs.com, that permit users to track changes and updates to content. When a producer updates its RSS output file, a message is sent to a central file server. When consumers want to know if there are updated RSS outputs from particular sources they go to the central file and see if there is a recent message from the producer of choice, rather than retrieving the RSS source directly. When new content is available, the consumer may send an electronic request directly to the producer's output file and read the contents into the consumers local files, archive, or repository. The infrastructure 416 for an enhanced syndication system may provide improved pinging systems. For example, a central server may be secure. In such a system, each request for a ping may carry an encryption-based key for the requestor. Responses to that requestor, which may be verified, for example with reference to a trusted third party, or using some other technique, may be time bound with constraints on start times, stop times, frequency, quotas, or the like. In another embodiment, the requestor may simply use a unique identification number. Pings may be subscription based, such that a for-fee pinger may be used more frequently than a free pinger. Thus there is disclosed herein a secure pinger for use in an RSS system. Also disclosed herein is a managed pinger, which may limit ping responses according to subscription levels, frequency, or any other suitable criteria.

The infrastructure 416 may more generally provide traffic management services including but not limited to real time monitoring of message latency, traffic and congestion, and packet quality across a network of end-to-end RSS exchanges and relationships. This may include real time monitoring of special traffic problems such as denial of service attacks or overload of network capabilities. Another service may be Quality-of-Service management that provides a publisher with the ability to manage time of sending of signaling messages for pingers, time of availability of the signaled-about messages, unique identifiers which apply to the signaling message and the signaled-about message or messages. This may also include quality of service attributes for the signaled-about message or messages and criteria for selecting end user computers that are to be treated to particular levels of end-to-end quality of service. This may be, for example, a commercial service in which users pay for higher levels of QoS.

It will be generally appreciated that the arrangement of layers and interfaces may vary, however in one embodiment syndication 414 may communicate directly with sources 402 while the applications 406 may communicate directly with users 404. Thus in one aspect, the systems described herein enable enhanced syndication systems by providing a consistent framework for consumption and republication of content by users 404. In general, existing technologies such as RSS provide adequate syndication services, but additional elements of a syndication system 400, such as social networking and semantic content management, have been provided only incrementally, and only on an ad hoc basis from specific service providers. The functions and services described above may be realized through, for example, the services oriented architecture described below with reference to FIG. 5, and/or any of the markup languages described below with reference to FIG. 6.

In one example model of an end-to-end content syndication system for, e.g., RSS, OPML, or other content, may include the following elements: convert, structure, store, spider, pool, search, filter, cluster, route, run. Conversion may transform data (bi-directionally) between application-specific or database-specific formats and the syndication or outlining format. Structure may be derived from the content, such as a knowledge structure inherent in interrelated OPML outlines, or metadata contained in RSS tags. Storage may occur locally on a user device, or at a remote repository. Spiders may be employed to search repositories and local data on user devices, to the extent that it is made publicly available, or actively published. Pools of data may be formed at central repositories or archives. Search may be conducted across one or more pools of data. Filters may be employed to select specific data feeds, items within a data feed, or elements of an OPML tree structure. Specific items or OPML tree branches may be clustered based upon explicit search criteria, inferences from metadata or content, or community rankings or commentary. Routing may permit combinations among content from various content sources using, e.g., web services or superservices. Such combinations may be run to generate corresponding display of results. Other similar or different combinations of elements from the broad categories above may be devised according to various value chains or other conceptual models of syndication services.

More generally, well-defined interfaces between a collection of discrete modules for an established value chain may permit independent development, improvement, adaptation, and/or customization of modules by end users or commercial entities. This may include configurations of features within a module (which might be usefully shared with others, for example), as well as functional changes to underlying software.

For example, an author may wish to use any one or more of a number of environments to create content for syndication. By providing a module with a standardized interface to RSS posting, converters may be created for that module to convert between application formats and an RSS-ready format. This may free contributors to create content in any desired format and, with suitable converters, readily transform the content into RSS-ready material. Thus disparate applications such as Microsoft Word, Excel, and Outlook may be used to generate content, with the author leveraging off features of those applications (such as spell checking, grammar checking, calculation capabilities, scheduling capabilities, and so on). The content may then be converted into RSS material and published to an RSS feed. As a significant advantage, users may work in an environment in which they are comfortable, and simply obtain needed converters to supply content to the RSS network. As a result, contributors may be able to more efficiently produce source material of higher quality. Tagging tools may also be incorporated into this module (or some author module) to provide any degree of automation and standardization desired by an author for categorization of content.

As another example, appropriate characterization of RSS material remains a constantly growing problem. However, if tagging occurs at a known and predictable point in the RSS chain, e.g., within a specific module, then any number of useful applications may be constructed within, or in communication with that module to assist with tagging. For example, all untagged RSS posts may be extracted from feeds and pooled at a commonly accessible location where one or more people may resolve tagging issues. Or the module may automatically resolve tagging recommendations contributed by readers of the item. Different rules may be constructed for different streams of data, according to editorial demands or community preferences. In short, maintaining a separate tagging module, or fixing the tagging function at a particular module within the chain, permits a wide array of tagging functions which may be coordinated with other aspects of the RSS chain.

In another aspect, a well-defined organization of modules permits improved synchronization or coordination of different elements of the modules in the RSS chain. Thus for example centralized aggregators may be provided, to improve usability, or to improve the tagging of content with metadata, where a combination of lack of standards and constantly evolving topics has frustrated attempts to normalize tagging vocabulary. By explicitly separating tagging from content, visibility of tagging behavior may be improved, and yield better tag selection by content authors. Similarly, search techniques (mapping and exploration) may be fully separated from indexing (pre-processing) to permit independent improvement in each.

A well-established "backplane" or other communications system for cooperating RSS modules (or other data feeds) may enable a number of business processes or enterprise applications, particularly if coupled with identity/security/role management, which may be incorporated into the backplane, or various modules connected thereto, to control access to data feeds.

For example, a document management system may be enhanced using an enhanced RSS system. Large companies, particularly document intensive companies such as professional services firms including accounting firms, law firms, consulting firms, and financial services firms, employ sophisticated document management systems that provide unique identifiers and metadata for each new document created by employees. Each new document may also, for example, be added to an RSS feed. This may occur at any identifiable point during the document's life, such as when first stored, when mailed, when printed, or at any other time. By viewing the RSS feed with, for example, topical filters, an individual may filter the stream of new documents for items of interest. Thus, for example, a partner at a law firm may remain continuously updated on all external correspondence relating to SEC Regulation FD, compliance with Sarbanes Oxley, or any other matter of interest. Alternatively, a partner may wish to see all documents relating to a certain client. Similarly, a manager at a brokerage house may wish to monitor all trades of more than a certain number of shares for a certain stock. Or an accountant may wish to see all internal memoranda relating to revisions to depreciation allowances in the federal tax code. An enhanced RSS system may provide any number of different perspectives on newly created content within an organization.

Other enterprise-wide applications may be created. For example, a hospital may place all prescriptions written by physicians at the hospital into an RSS feed. This data may be viewed and analyzed to obtain a chronological view of treatment.

Figure 5:
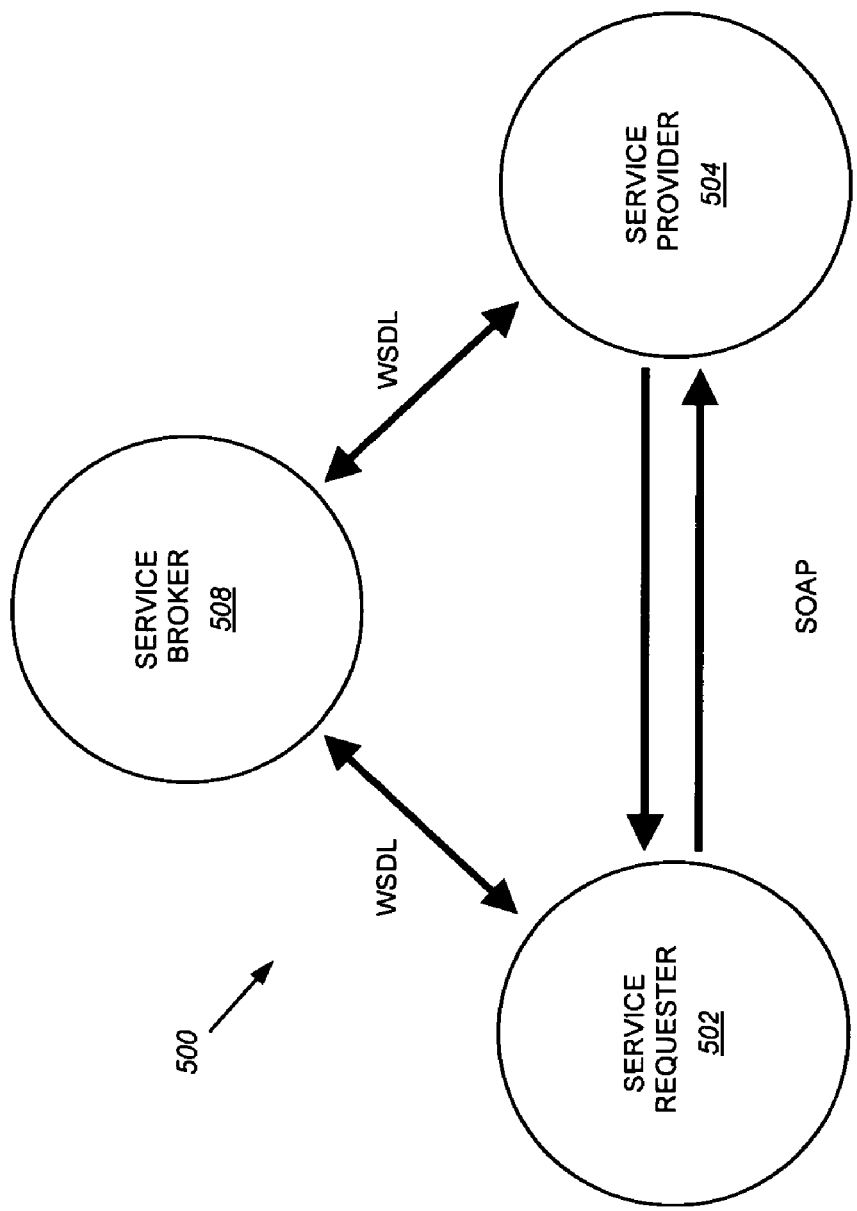
FIG. 5 depicts a system for delivering services in a syndication system.

FIG. 5 depicts a system for delivering services in a syndication system. As depicted, one technology for delivering services within the conceptual framework above is a service oriented architecture. A service oriented architecture ("SOA") 500 may include a service requester 502, a service provider 504, and a service broker 508.

In general, the service requester 502, which may be any of the clients 102 described above, discovers services and receives service descriptions through an exchange with the service broker 508 using a suitable syntax such as the Web Services Description Language ("WSDL"). The service provider 504 publishes service descriptions to the service broker 508, also using a syntax such as WSDL. The service requester 502 uses a service through communications with the service provider 504, using a transport protocol such as Simple Object Access Protocol ("SOAP"). An SOA 500 may include any number of requesters 502, brokers 508, and providers 504. Additionally, a number of protocols and standards may be employed to orchestrate the deployment of services in an SOA 500. In a web services embodiment, the Web service protocol stack is employed to define, locate, implement and interact with Web services. In general, this includes four main areas: service transport, XML messaging, service description, and service discovery. Service transport transports messages among network applications using protocols such as HyperText Transport Protocol ("HTTP"), File Transfer Protocol ("FTP"), Simple Mail Transfer Protocol ("SMTP"), and more recently the Blocks Extensible Exchange Protocol ("BEEP"). XML messaging encodes messages in a common XML format using, for example, XML-RPC, SOAP, and REST. The service description is used to describe the public interface for services, typically using WSDL as noted above. Service discovery may use WSDL, along with Universal Description, Discovery, and Integration ("UDDI"), which provides a platform independent, XML-based registry for public Internet listings.

An SOA 500 architecture may be used, for example, in an enhanced syndication system to relate metadata in an item of content to services that are available from the registry. Thus, for example, a publicly available registry may provide, among other things, a number of viewers for graphical images. An RSS item may refer to an image source, such as an MRI image in a medical record from a hospital, and may specify a viewer for the source image that is available through the registry. In operation, a client with appropriate permissions to view the image (also as managed, e.g., through the metadata for the enhanced syndication system), may retrieve the appropriate viewer service from the registry, and apply the viewer to view the source image. In this example, viewers may be freely provided, or may be licensed and made available through the registry on a fee per use basis or some other licensing terms. Similarly, the image source may be made available in various resolutions, each available under a different fee structure. In other embodiments, textual sources may be available in various forms ranging from a title and biographical data to an abstract to the full text of the source. Thus the SOA platform may be used to resell content from an RSS archive, using viewer or access privilege services made available through the registry. Other aspects such as identity and affiliation, as well as verification of these, may be made available as services in the SOA 500.

Figure 6:
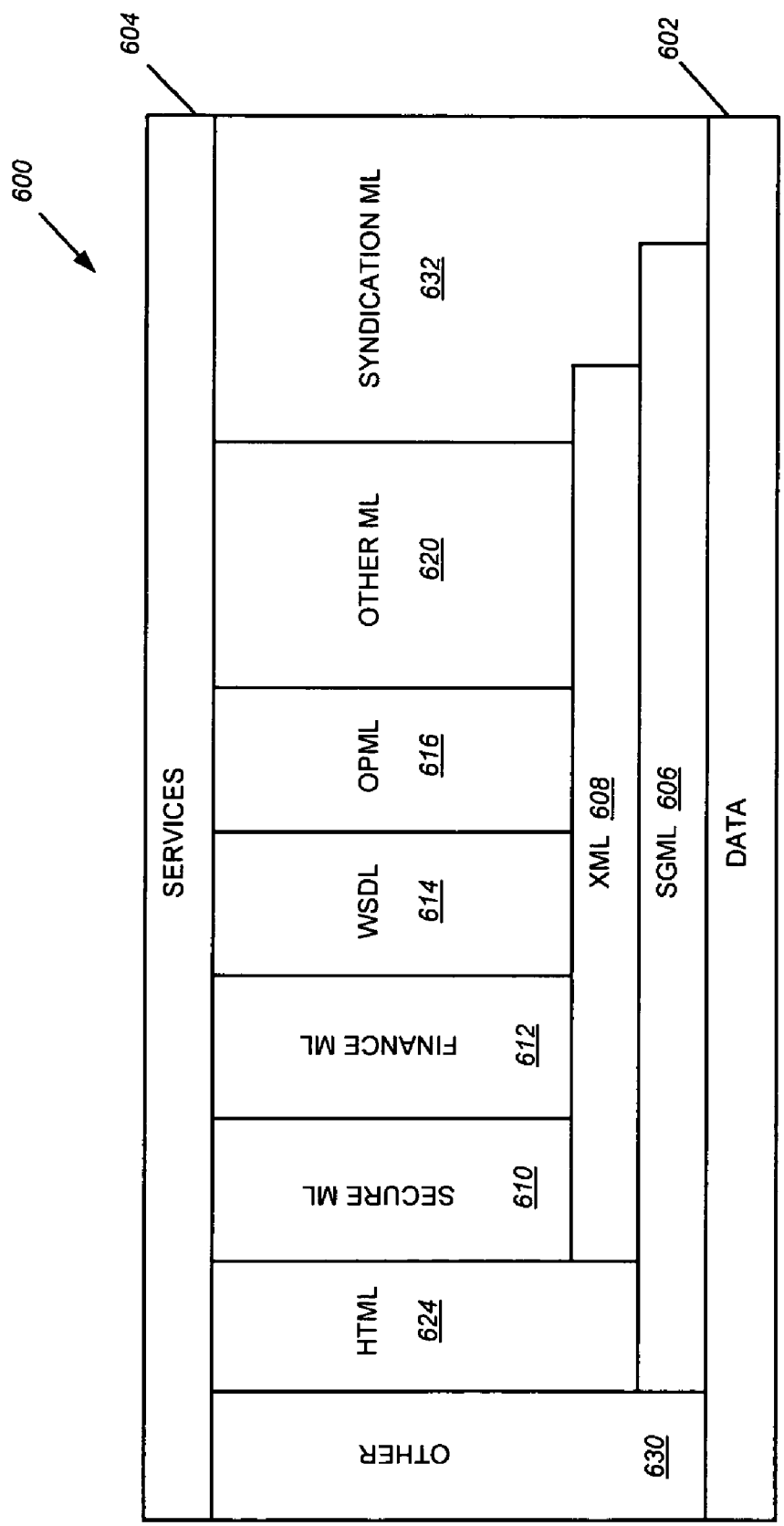
FIG. 6 shows an XML environment for syndication systems.

FIG. 6 shows an XML environment for syndication systems. As represent in FIG. 6, an XML environment 600 includes data 602, which may be any of the content source or other data sources described above that interacts with services 604, which may execute on a client 102, a server 104, or any other entity within a network.

Services 604, which may be, for example, any of the services described above with reference to FIG. 4, may employ a variety of standards, protocols, and programming languages to interact meaningfully with the data 602. This includes, for example, the use of programming tools that permit program logic to be deployed in, e.g., Java, Windows, Perl, PHP, C/C++, and so on. This also includes parsing, processing, and database access using, e.g., data binding (mapping XML components into native formats of various programming languages), Document Object Model ("DOM", a programming interface for manipulation of XML/HTML as program objects), Simple API for XML ("SAX", another API for XML documents), XSL (a stylesheet expression language), XSL Transformations ("XSLT", a language for transforming XML documents into other XML documents), XML Path Language ("XPATH", a language for referring to parts of XML documents), XSL Formatting Objects ("XSL-FO", an XML vocabulary for formatting semantics), and a variety of tools for queries and other access to commercial databases. Further, presentation may be provided using, e.g., XHTML, CSS/XSL-FO, SMIL, WSUI, and a host of other presentation tools. Services 604 may also employ various other XML-oriented tools for messaging, metadata, and web services, including SOAP, XML-RPC, RDF, UDDI, WSDL, and the like. Other specifications, such as the Voice eXtensible Markup Language (VoiceXML), Security Services Markup Language (S2ML), and OASIS Security Assertion Markup Language (SAML), provide special purpose grammars for specific functions. In general, these tools in various combinations permit a relatively arbitrary deployment of functions as services on top of content structured using XML grammars.

The services 604 may interact with data 602 through one or more established grammars, such as a secure markup language 610, a finance markup language 612, WSDL 614, the Outline Programming Markup Language ("OPML") 616, or other markup languages 620 based upon XML 608, which is a species of the Standard Generalized Markup Language ("SGML") 606. The interaction may be also, or instead, through non-XML grammars such as HTML 624 (which is a species of SGML) or other formats 630. More generally, a wide array of XML schemas have been devised for industry-specific and application-specific environments. For example, XML.org lists the following vertical industries with registered XML schemas, including the number of registered schemas in parentheses, all of which may be usefully combined with the systems described herein, and are hereby incorporated by reference in their entirety: Accounting (14), Advertising (6), Aerospace (20), Agriculture (3), Arts/Entertainment (24), Astronomy (14), Automotive (14), Banking (10), Biology (9), Business Reporting (2), Business Services (3), Catalogs (9), Chemistry (4), Computer (9), Construction (8), Consulting (20), Customer Relation (8), Customs (2), Databases (11), E-Commerce (60), EDI (18), ERP (4), Economics (2), Education (51), Energy/Utilities (35), Environmental (1), Financial Service (53), Food Services (3), Geography (5), Healthcare (25), Human Resources (23), Industrial Control (5), Insurance (6), Internet/Web (35), Legal (10), Literature (14), Manufacturing (8), Marketing/PR (1), Math/Data, Mining (10), Multimedia (26), News (12), Other Industry (12), Professional Service (6), Public Service (5), Publishing/Print (28), Real Estate (16), Religion, Retail (6), Robotics/AI (5), Science (64), Security (4), Social Sciences (4), Software (129), Supply Chain (23), Telecommunications (26), Translation (7), Transportation (10), Travel (4), Waste Management, Weather (6), Wholesale, and XML Technologies (238).

Syndication services, described in more detail below, may operate in an XML environment through a syndication markup language 632, which may support syndication-specific functions through a corresponding data structure. One example of a currently used syndication markup language 632 is RSS. However, it will be appreciated that a syndication markup language ("SML") as described herein may include any structure suitable for syndication, including RSS, RSS with extensions (RSS+), RSS without certain elements (RSS−), RSS with variations to elements (RSS'), or various combinations of these (e.g., RSS'−, RSS'+). Furthermore, an SML 632 may incorporate features from other markup languages, such as a financial markup language 612 and/or a secure markup language 610, or may be used in cooperation with these other markup languages 620. More generally, various combinations of XML schemas may be employed to provide syndication with enhanced services as described herein in an XML environment. It will be noted from the position of SML 632 in the XML environment that SML 632 may be XML-based, SGML-based, or employ some other grammar for services 604 related to syndication. All such variations to the syndication markup language 632 as may be usefully employed with the systems described herein are intended to fall within the scope of this disclosure, and may be used in a syndication system as that term is used herein.

According to the foregoing, there is disclosed herein an enhanced syndication system. In one aspect, the enhanced syndication system permits semantic manipulation of syndicated content. In another aspect, the enhanced syndication system offers a social networking interface which permits various user interactions without a need to directly access underlying syndication technologies and the details thereof. In another aspect, a wide variety of additional services may be deployed in combination with syndicated content to enable new uses of syndicated content. In another aspect, persistence may be provided to transient syndicated content by the provision of a database or archive of data feeds, and particularly the content of data feeds, which may be searched, filtered, or otherwise investigated and manipulated in a syndication network. Such a use of a syndication system with a persistent archive of data feeds and items therein, is now described in greater detail.

Figure 7:
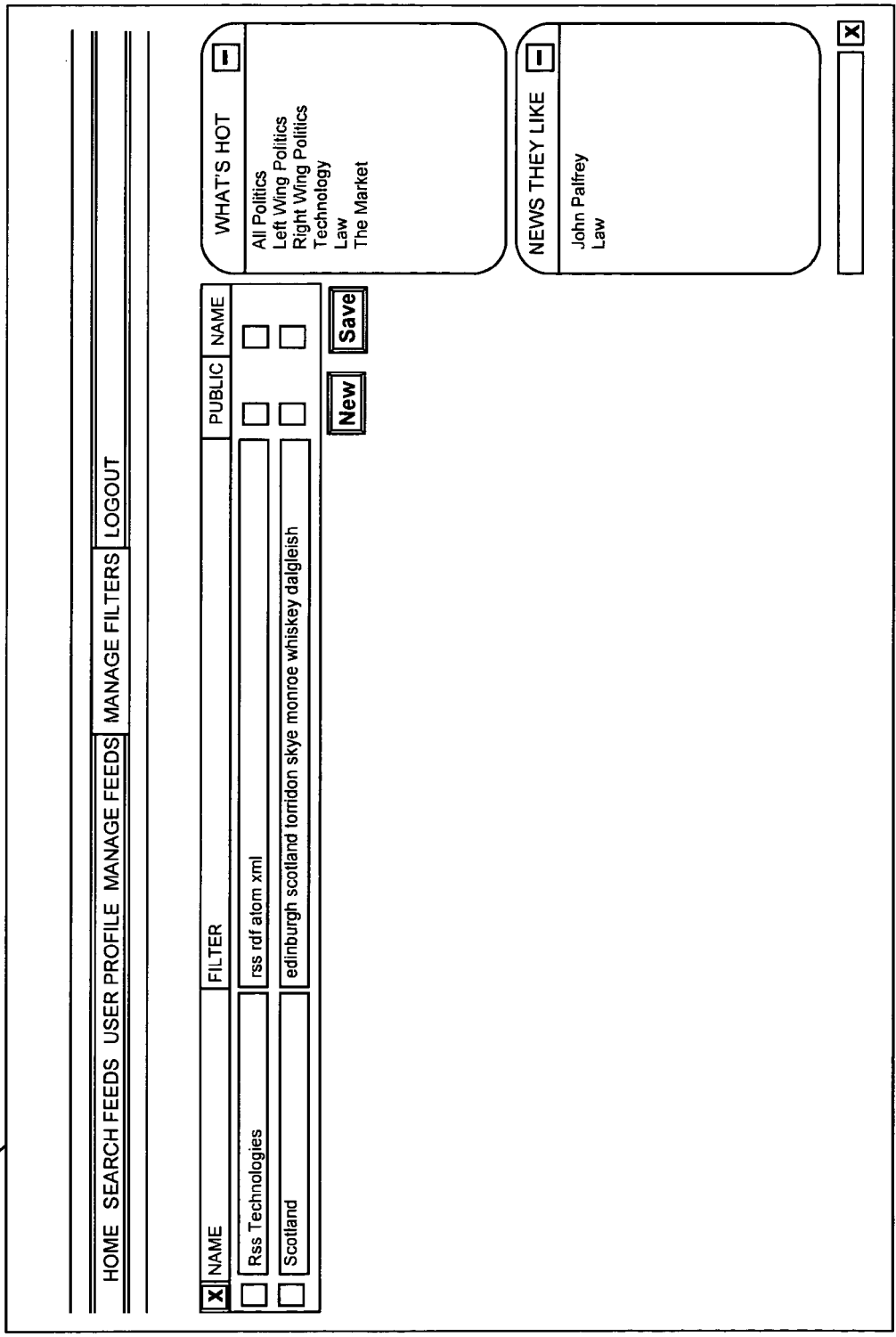
FIG. 7 shows a user interface for a syndication system.

FIG. 7 shows a user interface 700 for data feed management. More particularly, FIG. 7 depicts a manage filters page in which a user can create, edit, and share filters. The page may include navigation buttons and a "What's Hot" and a "News They Like" workspace. In addition, the page may provide a list of available filters. New filters may be created, and rules for each filter may be defined using, for example, Boolean or other operators on defined fields for data feeds, or on full text of items within data fields. In order to promote community activity, each filter may be made public for others to use, and the rules and other structure of each filter may also be optionally shared for others to inspect. As a significant advantage over existing systems, these filters may be applied in real time to RSS data feeds or other data feeds to narrow the universe of items that are displayed to a user.

In one aspect, the systems described herein may be used to scan historical feed data and locate relevant data feeds. For example, filters may be applied to historical feed data to identify feeds of interest to a user. For example, by searching for words such as "optical" and "surgery" in a universe of medical feeds, a user may locate feeds relevant to optical laser surgery regardless of how those feeds are labeled or characterized by other users or content providers. In another complementary application, numerous filters may be tested against known relevant feeds, with a filter selected according to the results. This process may be iterative, where a user may design a filter, test it against relevant feeds, apply to other feeds to locate new relevant feeds, and repeat. Thus, while real-time or near real time filtering is one aspect of the systems described herein, the filtering technology may be used with historical data to improve the yield of relevant material for virtually any topic of interest.

Another advantage of filtering historical data is the ability to capture transient discussions and topics that are not currently of interest. Thus, a user interested in the 1996 U.S. Presidential campaign may find little relevant material on current data feeds, but may find a high amount of relevant data in the time period immediately preceding the subsequent 2000 campaign. Similarly, an arbitrary topic such as Egyptian history may have been widely discussed at some time in the past, but receive very little attention today. The application of filters to historical feeds may provide search functionality similar to structured searching of static Web content. Thus there is disclosed herein a time or chronology oriented search tool for searching the contents of one or more sequential data feeds.

In another aspect, the filters may be applied to a wide array of feeds, such as news sources, to build a real-time magazine dedicated to a particular topic. The results may be further parsed into categories by source. For example, for diabetes related filters, the results may be parsed into groups such as medical and research journals, patient commentaries, medical practitioner Weblogs, and so forth. The resulting aggregated data feed may also be combined with a readers form, editor's overview, highlights of current developments, and so forth, each of which may be an additional data feed for use, for example, in a Web-based, real-time, magazine, or a new aggregated data feed.

In general, the filter may apply any known rules for discriminating text or other media to identified data feeds. For example, rules may be provided for determining the presence or absence of any word or groups of words. Wild card characters and word stems may also be used in filters. In addition, if-then rules or other logical collections of rules may be used. Proximity may be used in filters, where the number of words between two related words is factored into the filtering process. Weighting may be applied so that certain words, groups of words, or filter rules are applied with different weight to the ultimate determination of whether to filter a particular item. External references from an item, e.g., links to other external content (either the existence of links, or the domain or other aspects thereof) may be used to filter incoming items of a data feed. External links to a data feed or data item may also be used, such as by determining relevance by looking at the number of users who have linked to an item. This process may be expanded to measure the relevance of each link by examining the number of additional links by the linking entity. In other words, if someone links to a reference and that user has no other links, this may be less relevant than someone who links to the reference and has one hundred other links. This type of linking analysis system is provided, for example by Technorati.

Filters may apply semantic analysis to determine or approximate the tone, content, or other aspects of an item by analyzing words and word patterns therein. Filters may also examine the source of an item, such as whether it is from a .com top level domain or a .edu top level domain. The significance of a source designation as either increasing or decreasing the likelihood of passing through the filter may, of course, depend on the type of filter. Additionally, synonyms for search terms or criteria may be automatically generated and applied alongside user specified filter criteria.

Metadata may be used to measure relevance. Data feeds and data items may be tagged with either subject matter codes or descriptive words and phrases to indicate content. Tags may be provided by an external trusted authority, such as an editorial board, or provided by an author of each item or provider of each data feed. These and any other rules capable of expression through a user interface may be applied to items or posts in data feeds to locate content of interest to a particularly user.

As noted above, a user may also share data feeds, aggregated data feeds, and/or filters with others. Thus, in general there is provided herein a real-time data mining method for use with data feeds such as RSS feeds. Through the intelligent filtering enabled by this data feed management system, automatically updating information montages tailored to specific topics or users may be created that include any number of different perspectives from one to one hundred to one thousand or more. These real-time montages may be adapted to any number of distinct customer segments of any size, as well as business vertical market applications.

In another aspect, filters may provide a gating technology for subsequent action. For example, when a number of items are identified meeting a particular filter criteria, specific, automated actions may be taken in response. For example, filter results, or some predetermined number of filter results may trigger a responsive action such as displaying an alert on a user's monitor, posting the results on a Weblog, e-mailing the results to others, tagging the results with certain metadata, or signaling for user intervention to review the results and status. Thus, for example, when a filter produces four results, an e-mail containing the results may be transmitted to a user with embedded links to the source material.

Figure 8:
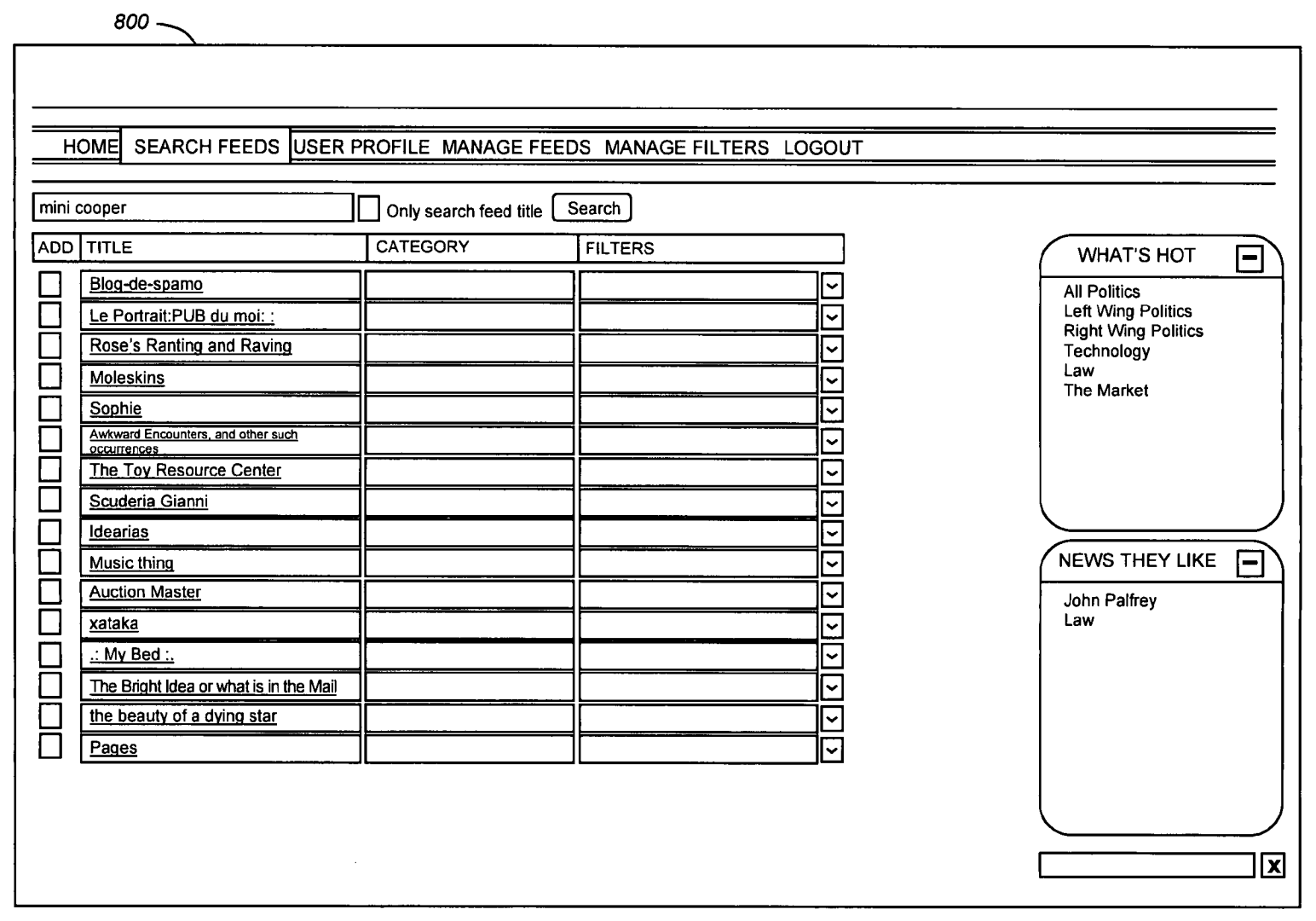

FIG. 8 shows a user interface 800 for data feed management. More particularly, FIG. 8 depicts a search feeds page in which a user can search for additional data feeds to monitor. The page may include navigation buttons and a "What's Hot" and a "News They Like" workspace. In addition, the page may include a text input field for user input of one or more search terms. There may also be one or more checkboxes or other controls for additional search parameters. For example, a user may select whether to search titles only, or other information in the description of the feed or individual items or postings in the feed. The search itself may also be stored, so that new searches for the same subject matter will optionally not include feeds that a user has already reviewed and rejected. Alternatively, the search may be persistent, so that the request search continues to execute against a database of feeds and posts as new feeds and new posts are added. Thus a user may leave the search and return to the search at a later time to review changes in results. The results for a search may be presented in the user interface along with a number of user controls for appropriately placing the feed within the user's feed environment. For example, a user may provide a new, user-assigned category to a feed, or select from one or more of the user's pre-existing categories. The user may also specify one or more filters, either pre-built or custom-built by the user to apply to items in the data feed once it is added. After a feed has been added, the user may review items passing through the assigned filter, if any, in the home page discussed above.

It will be appreciated that search results will be improved by the availability of well organized databases. While a number of Weblogs provide local search functionality, and a number of aggregator services provide lists of available data feeds, there does not presently exist a consumer-level searchable database of feed contents, at least nothing equivalent to what Google or Altavista provide for the Web. As such, one aspect of the system described herein is a database of data feeds that is searchable by contents as well as metadata such as title and description. In a server used with the systems described herein, the entire universe of known data feeds may be hashed or otherwise organized into searchable form in real time or near real time. The hash index may include each word or other symbol and any data necessary to locate it in a stream and in a post.

One useful parameter that may be included for searching is age. That is, the age of a feed, the age of posts within a feed, and any other frequency data may be integrated into the database for use in structured user searches (and the filters discussed in reference to FIG. 7).

As a further advantage, data may be retrieved from other aggregators and data feeds on a well-defined schedule. In addition to providing a very current view of data streams, this approach prevents certain inconsistencies that occur with currently used aggregators. For example, even for aggregator sites that push notification of updates to subscribers, there may be inconsistencies between source data and data feed data if the source data is modified. While it is possible to renew notification when source material is updated, this is not universally implemented in aggregators or Weblog software commonly employed by end users. Thus an aggregator may extract data from another aggregator that has not been updated. At the same time, an aggregator or data source may prevent repeated access from the same location (e.g., IP address). By accessing all of this data on a regular schedule (that is acceptable to the respective data sources and aggregators) and locally storing the results, the server described herein may maintain a current and accurate view of data feeds. Additionally, feeds may be automatically added by searching and monitoring in real time, in a manner analogous to Web bots used by search engines for static content.

In another aspect, a method of selling data feed services is disclosed herein. In this method, RSS data which is actually static content in files may be serialized for distribution according to some time base or time standard such as one item every sixty seconds or every five minutes. In addition, data may be filtered to select one item of highest priority at each transmission interval. In another configuration, one update of all items may be pushed to subscribers every hour, or on some other schedule in an effective batch mode. Optionally, a protocol may be established between the server and clients that provides real time notification of new items. A revenue model may be constructed around the serialized data in which users pay increasing subscription rates for increasing timeliness, with premium subscribers receiving nearly instantaneous updates. This in one aspect, a data feed system is modified to provide time-based data feeds to end users. This may be particularly useful for time sensitive information such as sports scores or stock prices. In another embodiment, the end-user feed may adhere to an RSS or other data feed standard, but nonetheless use a tightly controlled feed schedule that is known to both the source and recipient of the data to create a virtual time based data feed.

Figure 9:
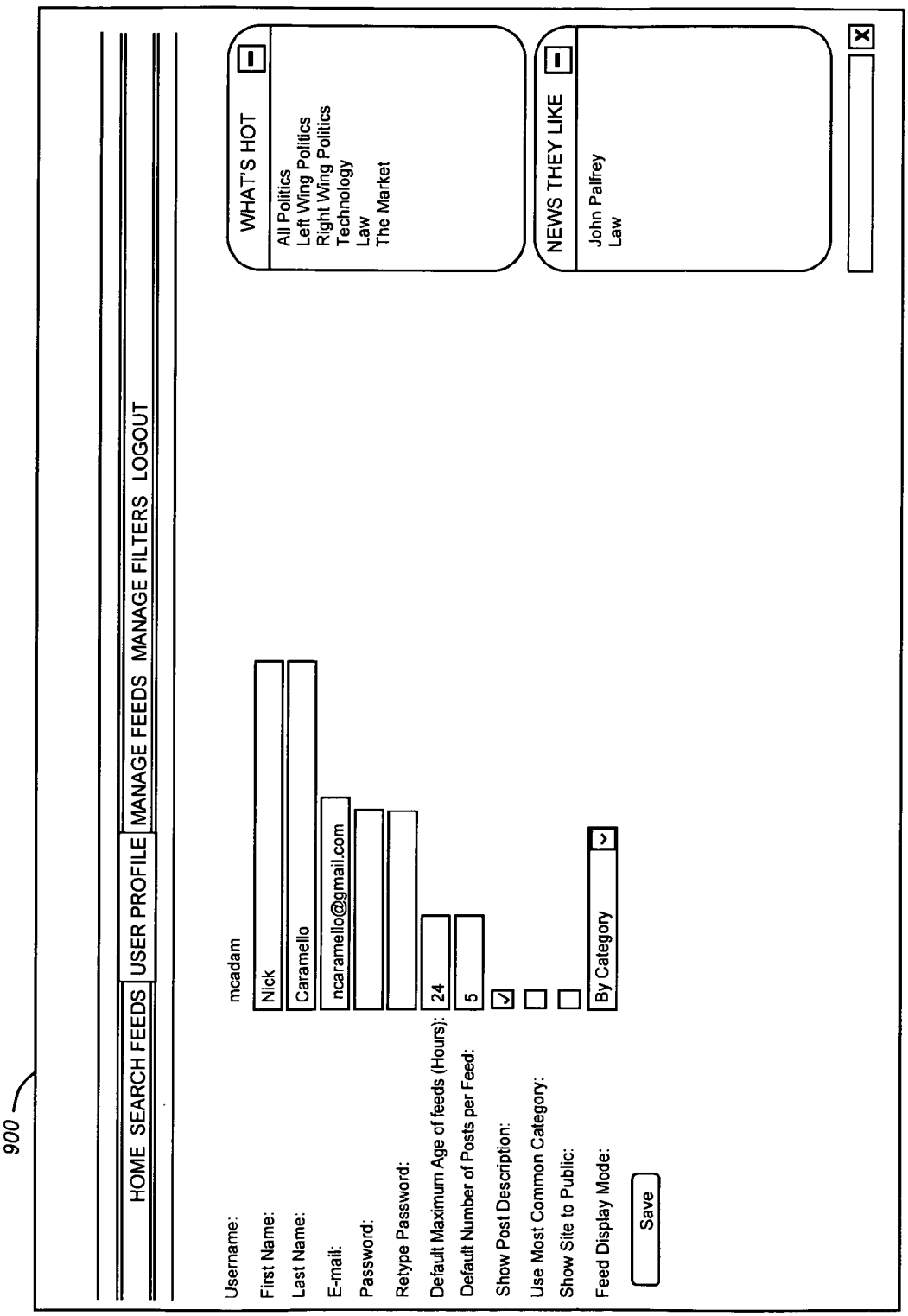
FIG. 9 shows a user interface for a syndication system.

FIG. 9 shows a user interface 900 for data feed management. More particularly, FIG. 9 depicts a user profile page in which a user can search for additional data feeds to monitor. The page may include navigation buttons and a "What's Hot" and a "News They Like" workspaces. In addition, the page may include text entry boxes, check boxes, and other controls, along with a save button for saving profile data. Text entry items may include, for example, a first name, last name, e-mail address, password (and retype password), and a default maximum age of feeds (e.g., in hours) and a default minimum and/or maximum number of posts per feed for controlling a user display thereof, such as in the home page. Checkboxes may provide for selection of certain features. For example, a user may choose to have post descriptions displayed, a user may make his home page or features thereof public, a user may choose to use common categories provided by the system, and a user may choose among one or more pre-defined or user configured display modes for feeds.

Additional profile information, such as user interests, preferences, and biographical data may also be optionally provided. This data and other user profile data may be used to target advertising associated with data feed sites or content. Thus a data feed management system is described herein in which ads are delivered that are of value to customers. In addition to self-signaling through profile data, the system may apply customer-filtering, behavioral analysis, or any other analytic tools, as applied to the user's feed selection and displayed posts, to select appropriate advertisements for that user. The revenues from advertisements may be shared in a number of ways, and may include shares of revenue to, for example, the operator of the data feed management system, an intermediary that places an ad that results in a sale, and/or individual or institutional content providers who contributed to the relevant data feed audience.

In another aspect of the systems described herein, feeds, posts, and/or filters may be clustered and shared in a number of ways as described above. Particular configurations may be branded and sold as a value-added service. Thus, for example, Warren Buffet's data feed selection and filtering may be of great interest to investors, bankers, and financiers. These selections may be sold to users who wish to see data feeds in the same manner as Warren Buffet. Similarly, someone may be interested in the writings and readings of Martha Stewart, Bill Clinton, Bill O'Reilly, Bill Gates, or Bill Belichick. Any of these individuals may brand and resell their selection of data feeds and design and use of filters. Similarly, commercial, political, or other institutional entities may present an official RSS feed identity. This may be provided for free for promotional purposes, such as promotion of a political party in a campaign, or promotion of a seasonal sale event by a retailer. Similarly, topical selections may be promoted by trade groups or individuals. For example, a biotech or patent filter may be promoted by a patent law firm. In these applications, the service sold or promoted may include either the filters and selections themselves, which an end user may then modify or use as desired, or an aggregated feed of results from the filters and selections without identification of the underlying criteria. Access to such an aggregated feed may be controlled through password based protection to a resulting Weblog, or using the identity-based RSS technology described above.

In one embodiment, a user may, either for a fee as described above, or for free, such as among a group of friends of interest-based community of bloggers, share not just search results, but rules for finding those search results. In another application of this technology, a buddy list or other community may share aggregator configurations and other data. In another application of this, a recommendation engine may identify popular and successful search and filtering criteria that match a particular use profile.

In one aspect, there is described herein a systematic approach to managing data feeds in an integrated, and possibly Web-based, user interface. In a first step, the user may process feeds, including for example searching for, analyzing and selecting feeds. In second step, a user may process posts within a feed, such as by filtering the posts as described above. In a third step, the aggregated and filtered results may be displayed to the user. This systematic approach also readily accommodates subsequent processing of the resulting items, such as by branding the technique for locating those items or by permitting sharing of the technique, both of which are described above. Additional processing steps may also include, for example, aggregating results into an aggregated feed, or any of the other processing steps identified in the foregoing detailed description.

A number of enhanced syndication systems providing security are now described in greater detail. While a number of examples of RSS are provided as embodiments of a secure syndication system, it will be appreciated that RDF, Atom, or any other syndication language, or OPML or other structured grammar, including more generally the S-definition set out above, may be advantageously employed within a secure syndication framework as set forth herein.

Security may impact a number of features of a syndication system. For example, a data stream system may use identity assignment and/or encryption and/or identity authentication and/or decryption by public and private encryption keys for RSS items and similar structured data sets and data streams. The system may include notification of delivery, as well as interpretation of delivery success, failure, notification of possible compromise of the end-to-end security system, non-repudiation, and so on. The identity assignment and encryption as well as the authentication and decryption as well as the notification and interpretation may occur at any or multiple points in the electronic communication process, some of which are illustrated and described below. A secure RSS system may be advantageously employed in a number of areas including, but not limited to general business, health care, and financial services. Encryption may be employed in a number of ways within an RSS system, including encryption and/or authentication of the primary message, notification to a sender or third party of receipt of messages, interpretation of delivery method, and processing of an RSS item during delivery.

In item-level encryption of the primary message, an item from an RSS source or similar source may be assigned an identifier (which may be secure, such as a digital signature) and/or encrypted with a key (such as a private key in a Public Key Infrastructure (PKI)) and transmitted to a recipient, who may use a corresponding public key associated with a particular source to authenticate or decrypt the communication. A public key may be sent to the recipient simultaneously or in advance by a third party, or collected by the recipient from a third-party source such as a public network location provided by the source, or a trusted third party. In other embodiments, an intended recipient may provide a public key to a sender, so that the sender (which may be a content source, aggregator, or other RSS participant) may encrypt data in a manner that may only be decrypted by the intended recipient. In this type of exchange, the intended recipient's public key may similarly be published to a public web location, e-mailed directly from the recipient, or provided by a trusted third party.

In tag-level encryption of fields of data delimited within a message, similar encryption techniques may be employed.

By using tag-level encryption, security may be controlled for specific elements of a message, and may vary from field to field within a single message.

In a notification system, a secondary or meta return message may be triggered by receipt, authentication, and/or decryption of the primary message by a recipient, and sent by the recipient to the message originator, or to a third party, to provide reliable notification of receipt.

In interpretation of delivery information, a sender or trusted intermediary may monitor the return message(s) and compare these with a list of expected return messages (based for example on the list of previously or recently sent messages). This comparison information may be interpreted to provide information as to whether a communication was successful, and in the case of communication to more than one recipient to determine how many and what percentage of communications were successful. The receipt of return messages that do not match the list of expected messages may be used to determine that fraudulent message are being sent to recipients, perhaps using a duplicate of an authentic private key, and that the security service may have been compromised.

In another aspect, a series of encryption keys may be used by the source and various aggregators or other intermediaries in order to track distribution of items through an RSS network. This tracking may either use notification and interpretation as described herein, or may simply reside in the finally distributed item, which will require a specific order of keys to properly decrypt some or all of the item. If this system is being used primarily for tracking, rather than security, encryption and decryption information may be embedded directly into the RSS item, either in one of the current fields, or in a new field for carrying distribution channel information (e.g., <DISTRIBUTION> . . . </DISTRIBUTION>.

In another aspect, the message may be processed at any point during distribution. For example, the communication process may include many stages of processing from the initial generation of a message, through its ultimate receipt. Any two or more stages may be engaged in identity assignment and/or encryption as well as the authentication and/or decryption as well as notification and/or interpretation. These stages may include but are not limited to message generation software such as word-processors or blog software, message conversion software for producing an RSS version of a message and putting it into a file open to the Internet, relay by a messaging service such as one that might host message generation and RSS conversion software for many producers, relay by a proxy server or other caching server, relay by a notification server whose major function is notifying potential recipients to "pull" a message from a source, and services for message receiving and aggregating and filtering multiple messages, message display to recipients, and message forwarding to further recipients.

In another aspect, a message may include one or more digital signatures, which may be authenticated with reference to, for example, the message contents, or a hash or other digest thereof, in combination with a public key for the purported author. Conversely, a recipient of a digitally signed item may verify authenticity with reference to the message contents, or a hash or other digest version thereof, in combination with a private key of the recipient.

Figure 10:
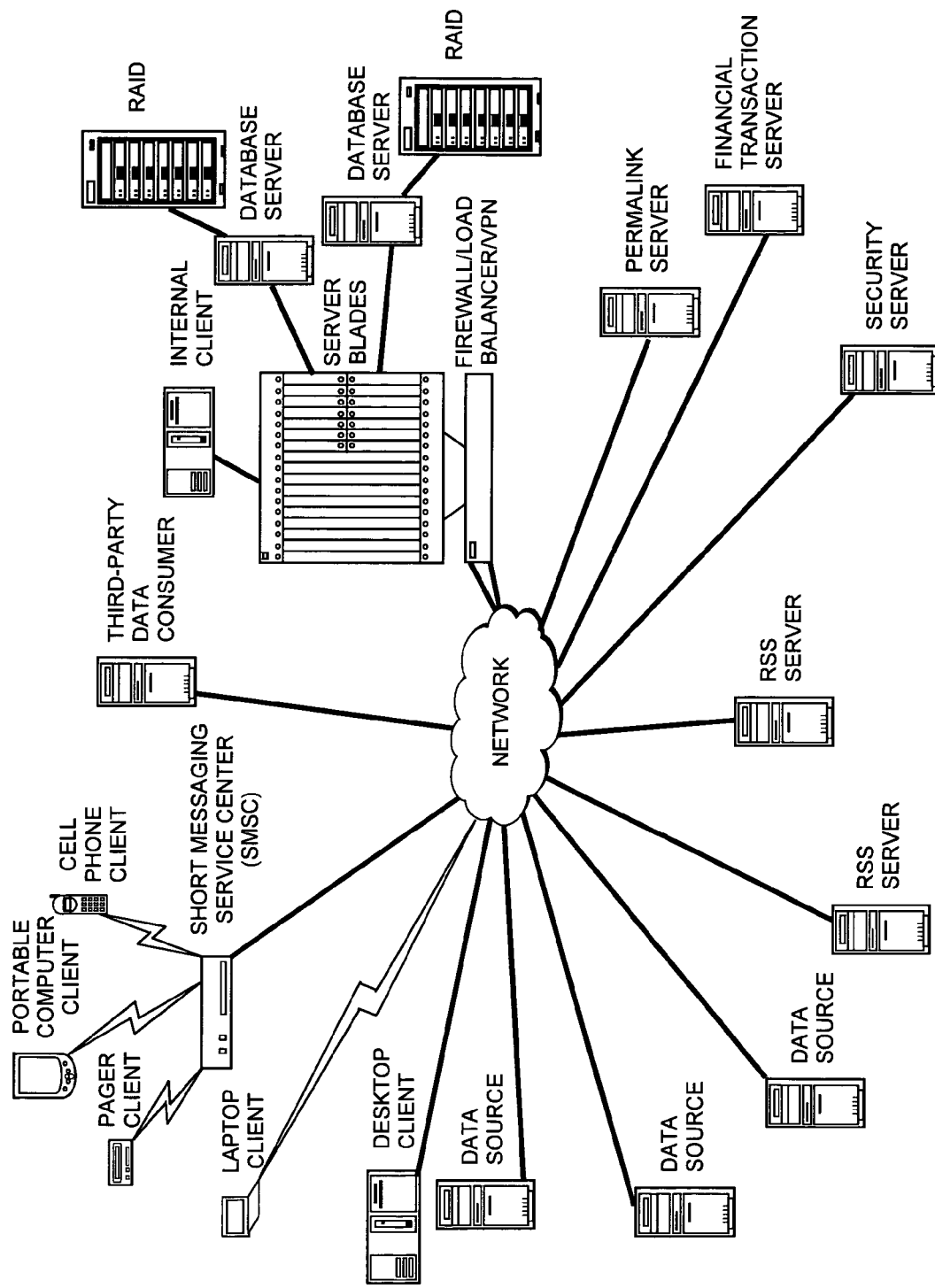
FIG. 10 shows participants in a secure syndication system.

Referring now to the figures, FIG. 10 shows a number of participants interconnected through a data network, any of which may participate in a secure RSS system as described herein. This may include, content publishers or other data sources, aggregators, RSS servers, mobile devices such as laptops, cell phones, portable computers, pagers, wireless e-mail devices, and so on, as well as local networks sharing a network connection, and any devices that might be connected to such a local network.

Figure 11:
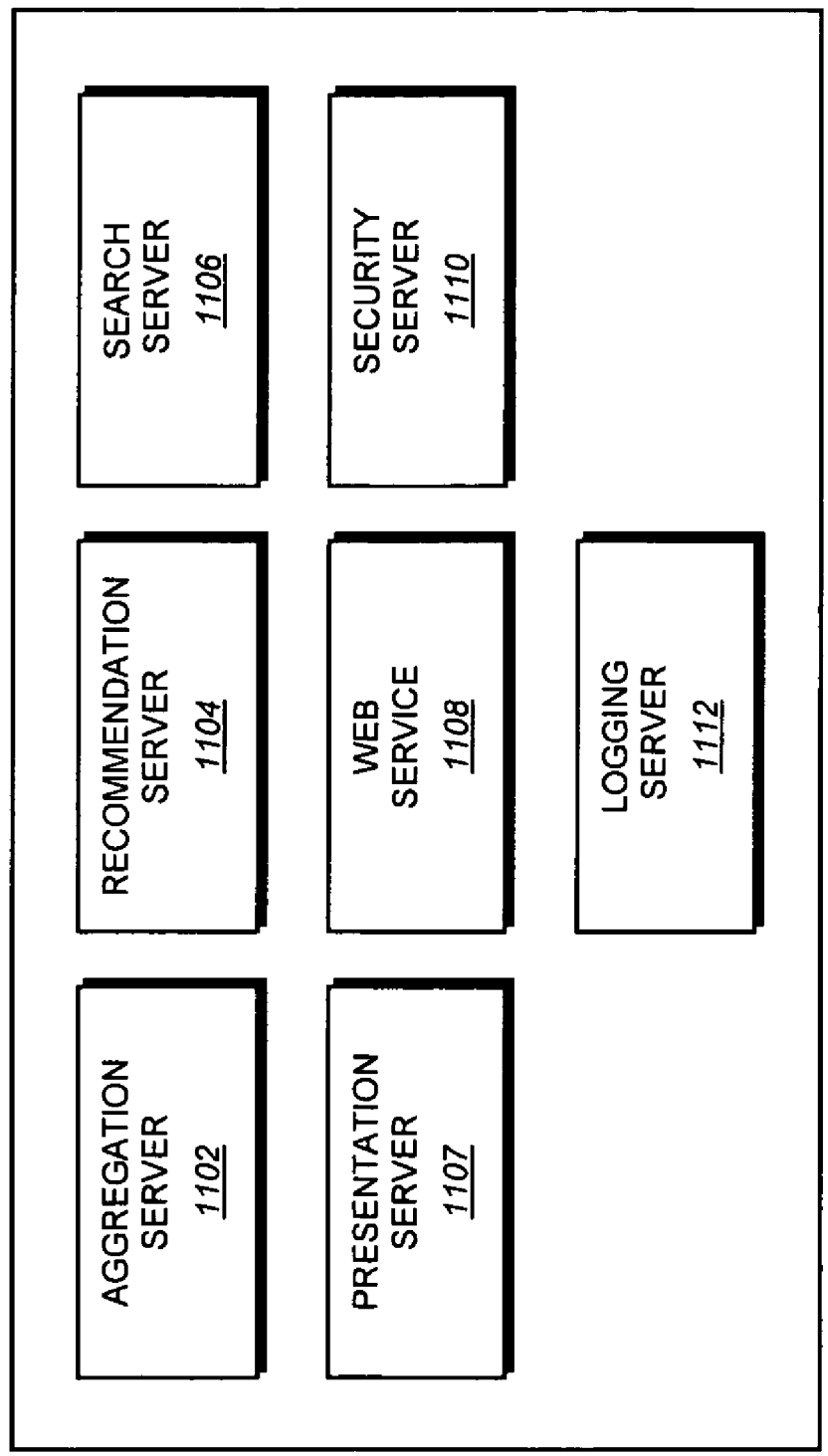
FIG. 11 shows logical servers in a secure syndication system.

FIG. 11 shows a number of logical servers 1100 that may be used in a secure RSS system. This may include, for example, an aggregation server 1102 that provides aggregation services including filtering of data streams, a recommendation server 1104 that may recommend new streams based on any suitable algorithms and available data, a search server 1106 that may provide search functions for RSS source data or indexed source data in a database, a presentation server 1107 that may manage connections to RSS clients, a web server 1108 that may manage traffic using any web-based protocols such as HTTP and/or HTML, a security server 1110 that provides security services such as those described below, and a logging server 1112 to log activities and users. It should be appreciated that these logical servers may reside on different physical devices at different locations in a data network, or may reside on a single device, or some combination of these. All such configurations are intended to fall within the scope of this disclosure unless a more specific configuration is required or otherwise clear from the context.

Figure 12:
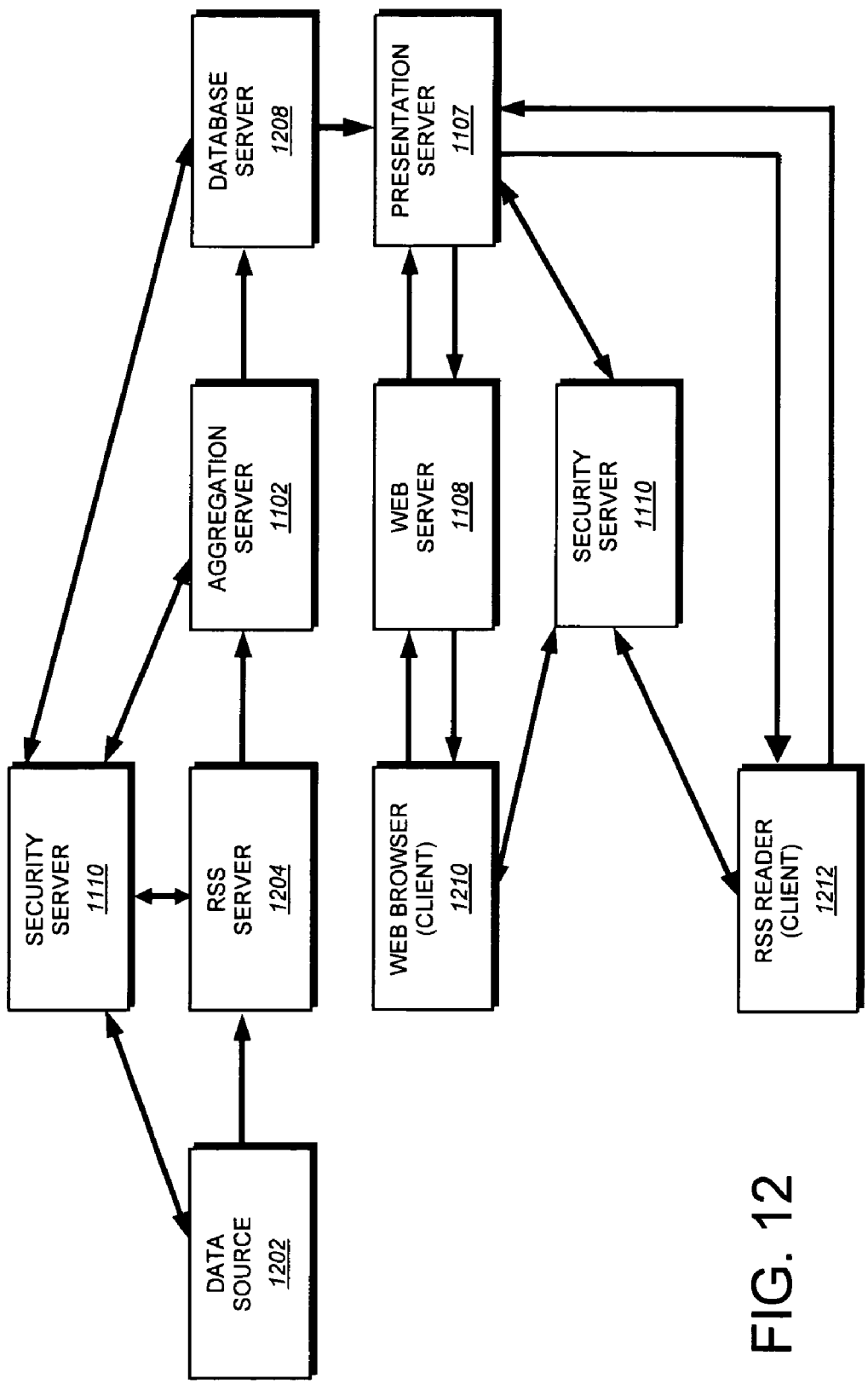
FIG. 12 shows reader interaction with a secure syndication system.

FIG. 12 shows an RSS reader 1212 accessing RSS content using the servers described above. In one embodiment, the reader connection to a presentation server may employ Secure Socket Layers (SSL), an SSH secure shell, Secure HTTP (S-HTTP) or other known web security technologies to provide a secure connection across a network between a client device and an RSS presentation server 1107.

The security server 1110 may also, or instead, communicate with various other components of the syndication system to provide secure end-to-end communications. It will be appreciated that any number of security servers 1110 may be employed. A security server 1110 may employ a number of different techniques for secure communications. For example, the security server 1110 may manage keys and key exchanges for security systems such as PKI (Public Key Infrastructure), PGP (Pretty Good Privacy), and so on. Security servers 1110 may provide key management and exchange independently, or may operate with reference to a trusted third party such as Entrust or VeriSign. In one aspect, the security system may be certificate based, with each user and component that participates in the secure RSS system having its own certificate issued from or signed by a certificate authority (which may again be a trusted third party).

Encryption based systems may use a wide array of cryptographic technologies including a number of those readily available in current commercially available operating systems and applications. This includes DES, S/MIME, Exchange Server Security, PGP, RSA, and various other forms of symmetric and asymmetric cryptography having various strengths (i.e., length of keys or encryption blocks), along with a number of techniques for managing keys, certificates, and associated access privileges. In general, any of these may be applied to a secure syndication system for various purposes. For example, data sources 1202 or other stored content may be stored in an encrypted form. As another example, data may be encrypted for communication over an open network. As another example, data may be encrypted for decryption by some subset of participants in the system, thus providing selective access to data on a policy or explicit permission basis. As another example, data may be authenticated using a digital signature that may be used to ensure that data has not been tampered with.

A number of schemas for (RSS-compliant) S-definitions are set out below showing a number of security features. In general, this may include encryption of individual fields or sub-portions of RSS's XML schema, encryption of entire RSS items, signatures for some or all of an RSS item, or security information for the item specifying, for example, where and how to obtain credentials to review a secure RSS item, encryption types, trusted authority information, and so on.

```
<?xml version="1.0"?>
<!-- RSS generated by NewsILike on Sep. 30, 2002; 4:00:
    00 AM Pacific-->
<rss version="2.0"
xmlns:newsilike="http://docs.newsilike.com/extensions-
    Module">
<channel>
<title>Scripting News</title>
<link>http://www.scripting.com/</link>
<description>A weblog about scripting and stuff like
    that.</description>
<language>en-us</language>
<newsililke:permanentLink>
http://www.newsilike.com/permalink/
    9A48FC1B2074A00E
</newsillike:permanentLink>
</channel>
</rss>
<?xml version="1.0"?>
<!-- RSS generated by NewsILike on Sep. 30, 2002; 4:00:
    00 AM Pacific-->
<rss version="2.0"
xmlns:newsilike="http://docs.newsilike.com/extensions-
    Module">
<channel>
<title>Scripting News</title>
<link>http://www.scripting.com/</link>
<description>A weblog about scripting and stuff like
    that.</description>
<language>en-us</language>
<newsilike:permanentLink>
http://www.newsilike.com/permalink/
    9A48FC1B2074A00E
</newsilike:permanentLink>
<newsilike:timeStamp>Sep. 30, 2002 4:00:00 AM
    Pacific</newsilike:timeStamp>
<newsilike:uniqueID>
13831786.1113475091493
<newsilike:uniqueID>376218.1113446404657</newsi-
    like:uniqueID>
</newsilike:uniqueID>
<signature xmlns="http://www.w3.org/2000/09/xmld-
    sig#">
</signature>
<newsilike:restrictedData>
<!--The following data is encrypted using the intended
    recipient's public key-->
ff8d 02 03 50 25 bd 84 . . . 13 6c 6d b2 13 4f f6 a6
</newsilike:restrictedData>
</channel>
</rss>
```

The above example shows use of a unique ID for an item assigned by its source (<newsilike:uniqueID>), as well as encrypted data enclosed within a restricted data tag (<newsilike:restrictedData>). While the annotation indicates that the data has been encrypted with an intended recipient's public key, it will be appreciated that the data may instead be encrypted using a private key, such as to provide authentication of source through public key decryption. In other variations, the restrictedData may provide decryption or key information for data encrypted within one of the other fields, such as the author, source, title, message body, date, time, channel, or any other field within RSS, or more generally, the S-definition described above. In other embodiments, such as the message-level encryption described above, the entire message, optionally with the exception of certain header information used for identification, may be encrypted using the various techniques described herein. The following exchange of messages provides another example of use of encryption in which a secure, token may be received from a subscriber:

```
<?xml version="1.0" encoding="utf-8" ?>
<RequestClientAuthenticationToken>
<Credentials>
00 a0 83 52 58 ab 6d fb . . . 55 16 2c 73 df00 13 8f
</Credentials>
<AccessTo>
NewsILikeSearchFunction
</AccessTo>
</RequestClientAuthenticationToken>
<?xml version="1.0" encoding="utf-8" ?>
<NewsILike>
<Time>2005-04-14 08:10:24</Time>
<ClientAuthenticationToken>
1f ba 93 09 27 f3 eb f3 . . . f9 49 32 0d 28 7f 52 f9
</ClientAuthenticationToken>
<Restrictions>
<AccessTo>NewsILikeSearchFunction</AccessTo>
<ExipirationTime>2005-04-15    08:00:00</Expiration-
    Time>
<IPAddress>194.27.48.102</IPAddress>
<User>Joe Smith</User>
<Sessions>1</Sessions>
</Restrictions>
</NewsILike>
```

As noted above, encryption may be employed more generally within messages, or among participants in a secure syndication system to achieve a wide range of possible new uses of syndication: Various uses of a secure syndication system are described below. It will be appreciated that these systems may be deployed using a number of cryptographic techniques of varying degrees of strength using an exercise of ordinary skill in the relevant arts.

In one aspect, data feeds or aggregated data feeds provided from a server for the system described herein may include a security layer for securely transmitting RSS or other feeds so that only authorized subscribers can decode the feed. A closely related concept in cryptography is the concept of identity. An identity service or layer may also be added to RSS or other feeds from the server used with the systems described herein. This service may, for example provide for digital signatures of feeds that allow verification of identity, or encryption that can only be decoded by users having a specific key (or identity).

Keys or passwords may be used to control access to data feeds and to authenticate user identity. Various applications may use, for example, symmetric encryption for security, and asymmetric public/private key encryption for identity. A number of such techniques are known to those of skill in the art and may be usefully employed with the systems described herein. Certificates may also be employed. A certificate is effectively a unique identifier of identity that can be verified through a trusted third party. The certificate is typically installed on a user computer, and enables a negotiation of a secure connection with other, similarly configured devices. VeriSign provides certificates commonly used in a number of software applications and Public Key Infrastructure applications, and these certificates are suitable for use with the enhanced security/identity layer described herein.

In one embodiment, there is disclosed herein a certificate-based data feed. In this embodiment, a user certificate may be embedded into a user RSS post so that the source can be affirmatively identified. Similarly, a subscriber to a feed may be identified by reference to an installed certificate. In one aspect, RSS communications may be securely restricted to specific sources and recipients, with decryption of data occurring, for example, through a one way key exchange between participants.

In another aspect, useful applications may be built upon a secure RSS system. If coherent access to a data feed is restricted to a specified source and recipient, such as through key exchange or other encryption based negotiation, then sensitive materials may be posted as an RSS feed and subscribed to by authorized recipients. For example, an entire patient medical history may be stored as a secure RSS feed. Similarly, tax filings, legal files, or other private documents or collections of documents may be stored as an RSS feed, with the owner granting transient or revocable access thereto for specific purposes. Returning to the medical history example, a business traveler in a foreign city may become ill, and provide immediate access to medical records for a treating physician. As a significant advantage over existing methods for file handling, an owner's discretion to grant access is not in any way inhibited by a current holder of physical files. Thus where a patient might ordinarily have to provide written authorization to a holder of medical records to release same, or worse still, physically retrieve the files in person, a patient with medical records stored in a secure RSS data format can grant access anywhere at any time and manage access in any manner most suitable to the patient's treatment.

In another application of secure RSS data, access may be role based. Thus, access may be granted, for example, to registered physicians. If a physician's license is revoked, the physician's certificate or identity may be updated immediately. As a consequence, the physician may be denied access to a patient's records even if the patient is not yet aware that the physician's license to practice medicine has been suspended or revoked. In a role based system, a number of feeds may also be configured to provide varying degrees of access to different users. Thus for example, all personal records may be stored as a number of RSS data feeds, with attorneys have access to one data set, law enforcement officers another data set, accountants another data set, and so forth. Optionally, the data may constitute a single feed of data with different portions of the feed encrypted differently according to desired access. In another aspect of role-based data feed systems, a particular data feed may be filtered, or display thereof varied, according to the recipient of the data. Thus a radiologist may receive a different view of medical data than an internist, a surgeon, or a nurse.

Roles or identities may be used in other ways. For example, feed selection may be governed in part by feed source. Thus, a user may only want to review feeds from, for example, registered doctors or certified financial planners. The status of these and other professionals may be associated with respective certificates, so that status, certification, or any other criteria may be determined along with identity when reviewing sources of feeds and/or aggregated feeds. Thus, there is also disclosed herein a technique for ranking, selecting, or filtering feeds and/or posts according to a criteria whose locus of evaluation does not exist within the network, but can be verified with reference to data in the feeds and/or posts. In another aspect, there is disclosed herein a technique for ranking, selecting, or filtering feeds and/or posts according to a criteria that is verified with reference to a trusted third party, such as through a certificate. In another aspect, a filter may be applied to feeds and/or posts that only accepts items from sources with verifiable identities.

Security keys that can be used by end-user computers to authenticate the signaling message itself, or elements within the signaled message (e.g., author, time, and source), or the signaled-about message. Security may be used to enable any number of cryptographically-based functions, including authenticity of a source, non-repudiation of content or time (such as for reliable date stamping), confidentiality of a message or other content, for which access may be limited to an individual reader, a list of specifically identified readers, or readers associated with a formal group, to name just a few examples. Security may also enable subscription-type services in which messages are made available on a subscription basis that controls keys used to decrypt contents rather than physical access to a feed.

Figure 13:
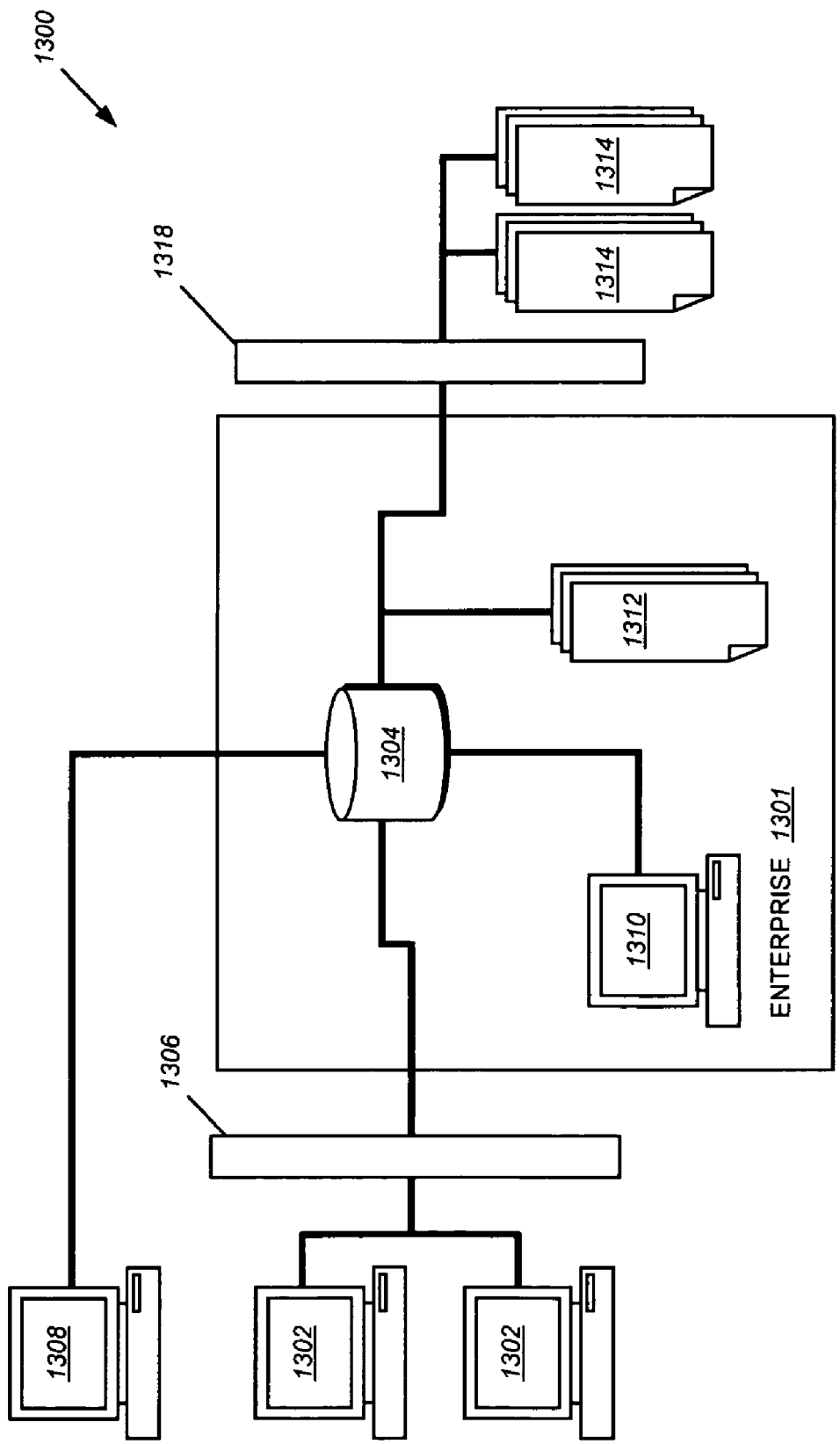
FIG. 13 shows a secure syndication infrastructure.

FIG. 13 shows a secure RSS system. The secure RSS system 1300 may include, for example one or more external clients 1302 communicating with a syndication server 1304 of an enterprise 1301 through a first firewall 1306, one or more other external clients 1308 communicating with the syndication server 1304 through a non-secure or public access port, one or more internal clients 1310 communicating with the syndication server 1304 through a local, corporate, or other private network, one or more data feeds 1312 providing syndicated content to the syndication server 1304 through a local, corporate or other private network, and one or more external data feeds 1314 providing syndicated content to the syndication server 1304 through a second firewall 1318. The firewalls 1306, 1318, syndication server 1304, and corresponding networks may be of suitable scale to provide an infrastructure for an enterprise-class syndication system. Thus in one aspect, there is provided herein a secure, enterprise-class syndication system capable of interacting with external syndicated content and/or readers through a public network.

The external clients 1302 may be, for example authorized readers of content maintained on the syndication server 1304. The other external clients 1308 may be public or anonymous readers of content maintained on the syndication server 1304, which may be different from the content provided to authorized readers. In one embodiment, two physically separate syndication servers 1304 may be provided for more complete and secure separation of public and private content. In another embodiment, the syndication server 1304 may include two separate logical servers. The syndication server 1304 may gather, aggregate, and/or index content from the internal data feed(s) 1312 as well as any number of external data feeds 1314. Data retrieved from the external data feeds 1314 may be scanned or otherwise reviewed before indexing or republication through the syndication server 1304. In one aspect, the syndication server 1304 may provide a public source of scanned or otherwise reviewed, cleansed, or secured data to external clients 1308. The syndication server 1304 may also provide secure, verifiable date or time stamping for external references. The syndication server 1304 may provide any of the user interfaces or other functions described above consistent with a syndication platform.

In another aspect, a secure syndication infrastructure may include, for example, web-based aggregator and a database, such as the syndication server 1304 above, behind a firewall, such as the firewall 1306 above. Access to the aggregator by external readers, which may be external clients 1302 or 1308 above, may be through SSL security or other strong encryption from the browser/reader to the web-based aggregator. The syndication server 1304 may maintain a certificate system, or employ a third party certificate service (not shown) such as VeriSign to authenticate itself to visitors, or to authenticate visitors.

In one aspect, the secure syndication system 1300 may be employed by an enterprise to regulate communications to authorized users such as employs and the general public, while permitting syndicated content to be supplemented with external content that has been reviewed for security or other parameters (appropriateness, relevance, reliability, etc.). In another aspect, the secure syndication system 1300 may be offered as a service to publishers of syndicated content, in which publishers may control access to content or employ other security features of the system 1300.

It will be appreciated that the syndication server 1304 may include an array of syndication related sub-systems. For example, the syndication server 1304 may operate one or more spiders that locate new syndicate content throughout the Internet, and a corresponding index or database of such content. The syndication server 1304 may provide a search engine (for public and/or private use) of indexed content, known data feeds, known authors, and so forth. The syndication server 1304 may provide aggregator and or filter functions such as those described above. The syndication server 1304 may also provide publication of syndicated content. In one aspect, a browser may display both secure and insecure feeds within a single interface, and may either visually distinguish between these feeds or provide no visual distinction. For example the feeds may be prominently grouped within separate areas of a user interface labeled as secure or insecure, or the feeds may be grouped together, but shaded or colored differently according to security status, or the feeds may appear identical and be grouped together.

A certificate and encryption manager may communicate with one or more other entities within the system 1300 to provide secure data transmission, authentication, authorization, and any other functions that might be associated with cryptographic capabilities. The system 1300 may employ approved sources, uses and user lists to control access to data, as well as accessing to writing, editing, posting capabilities within the secure RSS system 1300. The browser may be any conventional browser used to view syndicated content within the system 1300.

A source spider or bot may continuously search the World Wide Web and RSS feeds/files for new subject matter outside the system firewall 1318. A source authenticator and/or gatekeeper, which may be, for example, within the firewall 1318, the syndication server 1304, or somewhere else within the system 1300, may review sources identified by the spider using, for example, the approved lists, and transmit approved references to the database of sources and items. A security system such as SSL can be used to secure all communications that occur outside the firewall, and may provide a secure, externally accessible RSS system. Access and sessions may be, for example certificate based using internally managed certificates, or certificates issued by a trusted, external source such as VeriSign or Entrust.

Security may be extended to all RSS functions including pinging, posting, distribution (RSS channels and aggregators) and reading. The system can offer a secure write point behind a firewall, so that a blog or other RSS-based content provider is secure. The system may also mix secure and unsecured elements, such as by referencing external data feeds 1314 and internal data feeds 1312. The external feeds 1314 may be either secured by processing them through the gatekeeper, or may be used within the system 1300 along with a tag or other identifier noting that they are external, untrusted references. Similarly, the system 1300 could provide administrative tools to permit control of access to outside sources by users of the system, or according to system privileges or policies.

The security system 1300 could be deployed or used differently for other functions, such as secure pinging through a secure session between parties. It should also be appreciated that different network communication mediums may have different security, session, and communication characteristics. An RSS system with session and security capabilities may effectively incorporate any features from these complementary systems (e.g., electronic mail, ftp, instant messaging, peer-to-peer file sharing, HTTP browsing) that might be usefully combined with the RSS systems. Thus, for example, an RSS channel may be configured to provide continuous presence in a manner similar to IRC or instant messaging systems. RSS channels or items may have file attachments made available for download using hierarchical path names and file transfer capabilities of ftp. In another aspect, users or participants could have continuous presence like instant messaging, which may significantly improve social aspects of the systems described herein. Peer-to-peer networking techniques, such as the BitTorrent techniques for managing upload and download traffic for popular content, may be incorporated into the managed RSS system described herein.

In one aspect, all RSS communications may be made secure. The pinger of a conventional RSS system may effectively become a session manager where sessions are used to carry RSS data. Within a session, encryption keys (or challenge/response-based encryption communications) may be transferred before or in parallel with other feed-based communications. The session manager may provide notifications of updates, function as a carrier of core content, and provide traffic management for an RSS-based communication medium. Additionally, network management-like protocols may be employed to distribute content (e.g., feeds or items) and manage traffic (e.g., ping requests) within an active RSS network. Thus, for example, pinging responsibility may be distributed among a number of different servers that function like domain name servers in TCP/IP systems. Regional participants could handle regional traffic, and transfer or share ping load during busy times or route around congestion points. This offers significant advantages over current ping systems in which pingers simply drop excess ping requests.

In another aspect, digital rights management systems may be employed with policy-based or authority or permission based access to RSS content. Additional functions and relationships may be generally as depicted in the figure, and may include any of the system components described above for use with an RSS system.

These and other variations may be used in a secure syndication system as described herein. A number of basic syndication operations are now considered in greater detail.

Figure 14:
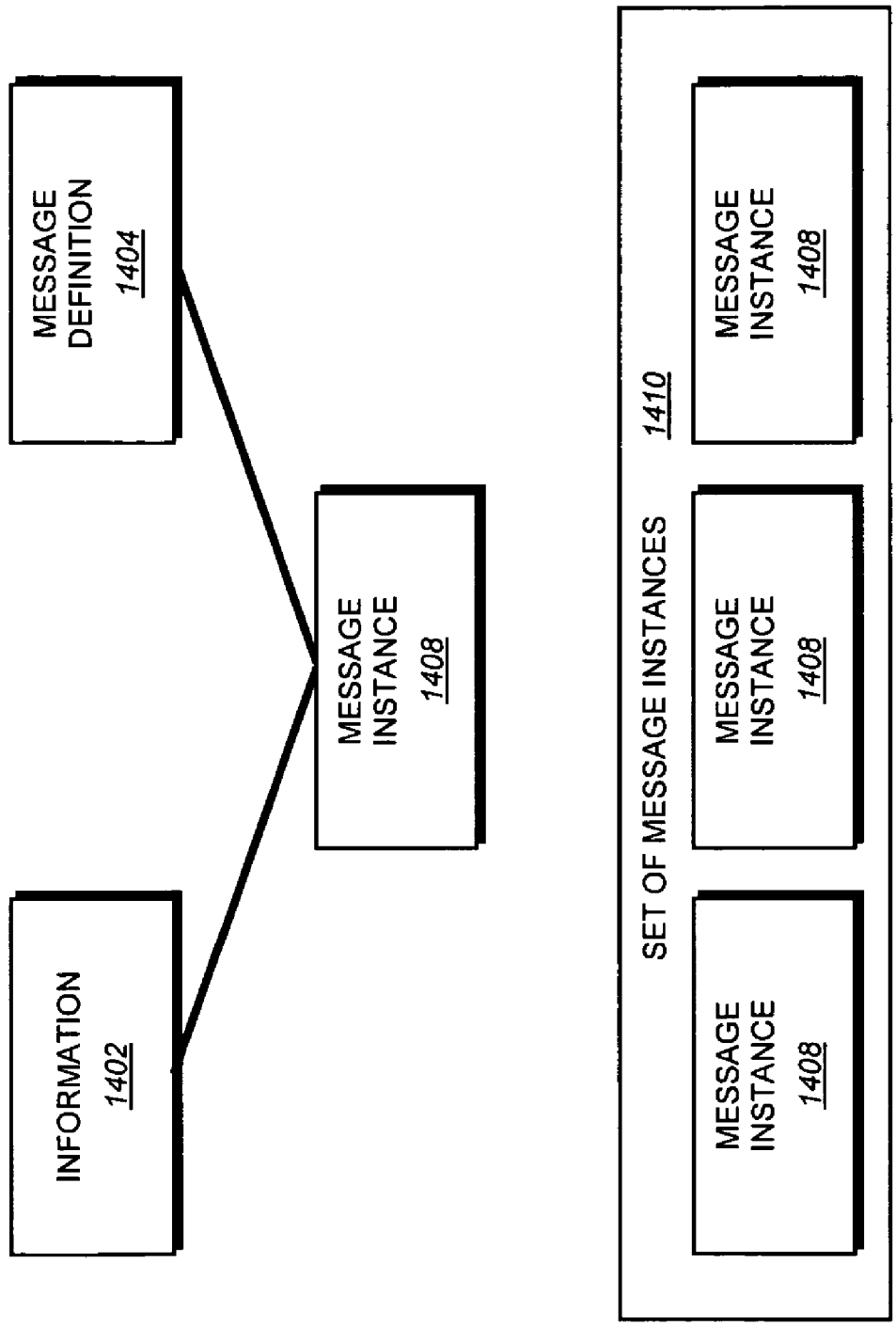
FIG. 14 shows a structure for syndicated content.

FIG. 14 shows a typical interaction between Internet-based services. A typical interaction may involve passing information 1402 between machines on a network, such as any of the internetworks 110 described above. The information 1402 may be formatted as a message instance 1408 that may conform to a message definition.

Two widely known message definitions used for Internet syndication are RSS 2.0 (RSS) and the Atom Syndication Format Draft Version 9 (Atom, as submitted to the IETF on Jun. 7, 2005 in the form of an Internet-Draft). The system disclosed herein may include a message definition 1404, referred to herein variously as the "S-definition" or the "Enhanced Syndication Services (ESS) definition", which may incorporate features of, and may supplement features of, these and any other syndication message definitions, or other definitions useful for enhanced services as described generally above. Any message conforming to the S-definition may be referred to as an S-message or an ESS message. RSS and Atom may be viewed as species of the S-definition.

The S-definition may be described in terms of XML or any other suitable standardized or proprietary format. XML, for example, is a widely accepted standard of the Internet community that may conveniently offer a human-readable and machine-readable format for an S-definition. Alternatively, the S-definition may be described according to another syntax and/or formal grammar. Generally, any commonly accepted expression of the S-definition may be used with the systems described herein.

The message instance 1408 may conform to a message definition 1404, which may be an abstract, typed definition. The abstract, typed definition may be expressed, for example, in terms of an XML schema, which may without limitation comprise XML's built-in Document Type Definition (DTD), XML Schema, RELAX NG, and so forth. The information 1402 may also, or instead, be represented as a set of message instances 1410, wherein each message instance 1408 in the set 1410 may be atomic and wherein the message instances 1408 in the set 1410 may be ordered and/or may naturally occur as a series. It should be appreciated that the information 1402 may change over time and that any change in the information 1402 may naturally be associated with a change in a particular message instance 1408 and/or a change in the set of message instances 1410.

Figure 15:
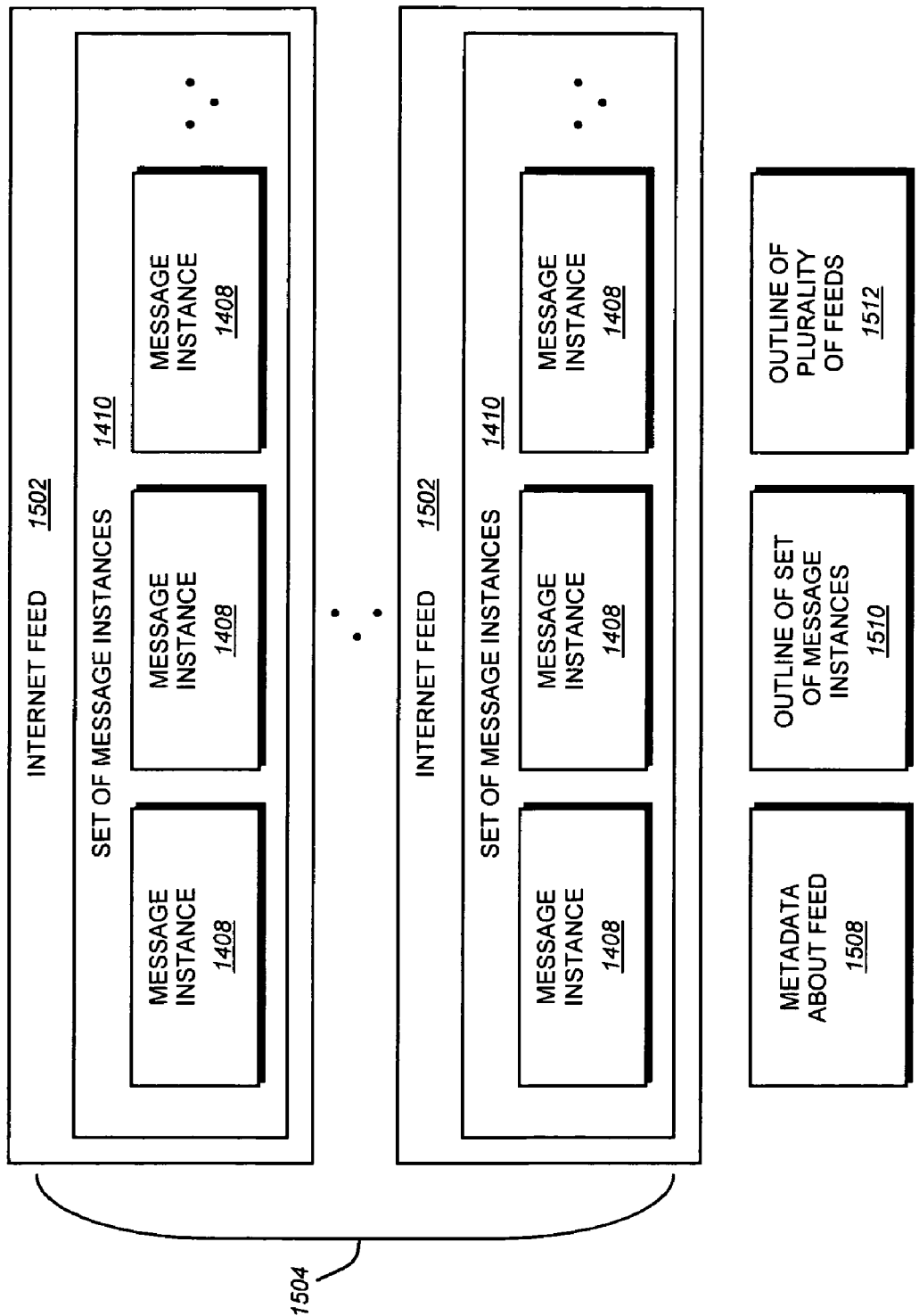
FIG. 15 shows a data feed of syndicated content.

FIG. 15 shows a data feed of syndicated content. A syndicated data feed may be implemented as one or more network services. Typically, this would entail provisioning a data feed 1502 over a network such as the Internet, or any other internetwork 110 described above. The data feed 1502 may include a set of messages 1410. As depicted with horizontal ellipsis, the set of message instances 1410 may vary over time, more specifically growing as message instances 1410 or items, as they are referred to elsewhere herein, accumulate over time in the data feed 1502.

The data feed 1502 may be associated with one or more message instances 1508 comprising metadata associated with the data feed 1502 and/or the message instance(s) 1508. The data feed 1502 may conversely be associated with a message instance 1510 including an outline of the set of message instances 1410. The outline of the set of message instances 1410 may identify some or all of the set of message instances 1410 and/or may include excerpts of one or more message instance 1408 from within the set of message instances 1410. Similarly, a plurality of data feeds 1504 may be outlined within a message instance 1512 associated with that data feed(s) 1502.

When the message instance 1408 resides in the set of message instances 1410, the message instance 1408 may be referred to as an entry. When the message instances 1408 includes an outline (such as message instance 1510 or message instance 1512), the message instance 1408 may be referred to as a list. It should be appreciated, however, that the words "list" and "outline" may be used interchangeably in some descriptions. When the message instance 1408 specifically comprises metadata associated with the data feed 1502 (such as message instance 1508), the message instance 1408 may be referred to as a channel definition or channel. When the list associated with message instance 1512 contains metadata associated with more than one data feed 1502, the message instance 1512 may be referred to as a metachannel, aggregate channel, or channel guide. It should be appreciated that any message instance 1408 may include metadata. When the message instance 1408 specifically comprises a URI or other resolvable reference that is associated with a retrieval location for a feed, the message instance 1512 may be referred to as a subscription request. The retrieval location may without limitation comprise a network address, a network protocol, a path, a virtual path, and/or a filename.

The S-definition may include any or all of the elements of the following standards and drafts, all of which are hereby incorporated in their entirety by reference: RSS 2.0; Atom Syndication Format as presented in the IETF Internet-Draft Version 9 of the Atom Syndication Format; OPML 1.0; XML Signature Syntax (as published in the W3C Recommendation of 12 Feb. 2002); the XML Encryption Syntax (as published in the W3C Recommendation of 10 Dec. 2002); the Common Markup for Micropayment per-fee-links (as published in the W3C Working Draft of 25 Aug. 1999). The elements of these specifications, which may be employed to support enhanced syndication services as described herein, include without limitation: channel, title, link, description, language, copyright, managing editor (managingEditor), Web master (webmaster), publication date (pubDate), last build date (lastBuildDate), category, generator, documentation URL (docs), cloud, time to live (ttl), image, rating, text input (textInput), skip hours (skipHours), skip days (skipDays), item, author, comments, enclosure, globally unique identifier (guid), source, name, URI, email, feed, entry, content, contributor, generator, icon, id, logo, published, rights, source, subtitle, updated, opml, head, date created (dateCreated), date modified (dateModified), owner name (ownerName), owner e-mail (ownerEmail), expansion state (expansionState), vertical scroll state (vertScrollState), window top (windowTop), window left (windowLeft), window bottom (windowBottom), window right (windowRight), head, body, outline, signature (Signature), signature value (SignatureValue), signed information (SignedInfo), canonicalization method (CanonicalizationMethod), signature method (SignatureMethod), reference (Reference), transforms (Transforms), digest method (DigestMethod), digest value (DigestValue), key information (KeyInfo), key value (KeyValue), DSA key value (DSAKeyvalue), RSA key value (RSAKeyValue), retrieval method (RetrievalMethod), X509 data (X509Data), PGP Data (PGPData), SPKI Data (SPKIData), management data (MgmtData), object-(Object), manifest (Manifest), signature properties (SignatureProperties), encrypted type (EncryptedType), encryption method (EncryptionMethod), cipher data (CipherData), cipher reference (CipherReference), encrypted data (EncryptedData), encrypted key (EncryptedKey), reference list (ReferenceList), encryption properties (EncryptionProperties), price, text link (textlink), image link (imagelink), request URL (request URL), payment system (paymentsystem), buyer identification (buyerid), base URL (baseurl), long description (longdesc), merchant name (merchantname), duration, expiration, target, base language (hreflang), type, access key (accesskey), character set (charset), external metadata (ExtData), external data parameter (ExtDataParm).

The S-definition may include elements pertaining to medical devices, crawlers, digital rights management, change logs, route traces, permanent links (also known as permalinks), time, video, devices, social networking, vertical markets, downstream processing, and other operations associated with Internet-based syndication, all of which may be employed to provide enhanced syndicated services as described herein. This includes, without limitation: clinical note (ClinicalNote), biochemistry result (BiochemistryResult), DICOM compliant MRI image (DCMRI), keywords (Keywords), license (License), change log (ChangeLog), route trace (RouteTrace), permalink (Permalink), time (Time), shopping cart (ShoppingCart), video (Video), device (Device), friend (Friend), market (Market), downstream processing directive (DPDirective), set of associated files (FileSet); revision history (RevisionHistory), revision (Revision), branch (Branch), merge (Merge), trunk (Trunk), and symbolic revision (SymbolicRevision). The element names may be case sensitive or case insensitive.

The contents of the clinical note element may without limitation include a note written by a clinician, such as a referral letter from a primary care physician to a specialist. The contents of the biochemistry result element may without limitation include indicia of total cholesterol, LDL cholesterol, HDL cholesterol, and/or triglycerides. The contents of the DICOM compliant MRI image element may without limitation include an image file in the DICOM format. The content of the keyword element may without limitation include a word and/or phrase associated with the content contained in the message, wherein the word and/or phrase may be processed by a Web crawler. The content of the license element may without limitation include a URL that may refer to a Web page containing a description of a license under which the message is available. The content of the change log element may without limitation include a change log. The content of the route trace element may without limitation include a list of the computers through which the message has passed, such as a list of "received:" headers analogous to those commonly appended to an e-mail message as it travels from sender to receiver through one or more SMTP servers. The content of the permalink element may without limitation include a permalink, such as an unchanging URL. The content of the time element may without limitation include a time, which may be represented according to RFC 868. The content of the shopping cart element may without limitation include a representation of a shopping cart, such as XML data that may include elements representative of quantity, item, item description, weight, and unit price. The content of the video element may without limitation include a MPEG-4 encoded video file. The content of the device element may without limitation include a name of a computing facility. The content of the friend element may without limitation include a name of a friend associated with an author of an entry. The content of the market element may without limitation include a name of a market. The content of the downstream processing directive element may without limitation include a textual string representative of a processing step, such as and without limitation "Archive This," that ought to be carried out by a recipient of a message.

The above description of the particular elements of the S-definition is intended to be illustrative of the types and semantics of the elements supported by the S-definition that may be used to provide enhanced syndication services. As such, the above description is not intended to be limiting as to the types of elements that might be used or the particular nomenclature therefore.

The S-definition describes a message format that may enable Internet-syndication operations. An S-message according to the S-definition may be associated with one or more of XML, a feature of RSS, a feature of Atom, a feature of OPML, a micropayment, electronic commerce, a representation of medical information, the representation of public information, the representation of private information, the representation of protected information, a tag for a crawler, versioning and/or a change log, a digital signature, basic authentication, digest authentication, may associated with encryption, a license term, a route trace, a permalink, an enclosure or file attachment, a indication of time or a timestamp, e-commerce, searching, filtering, clustering, a database, security, video, a device, a user interface, a rule, non-syndication technologies, social networking, a vertical market, downstream processing, semantic processing, and/or a source.

Schemas typically have required and optional elements. In one embodiment of the S-definition, any or all elements may be optional. Thus, any message comprising one or more element of the S-definition may be a valid S-message. In other embodiments, one or more elements may be required, such as elements used to support underlying syndication functions.

Figure 16:
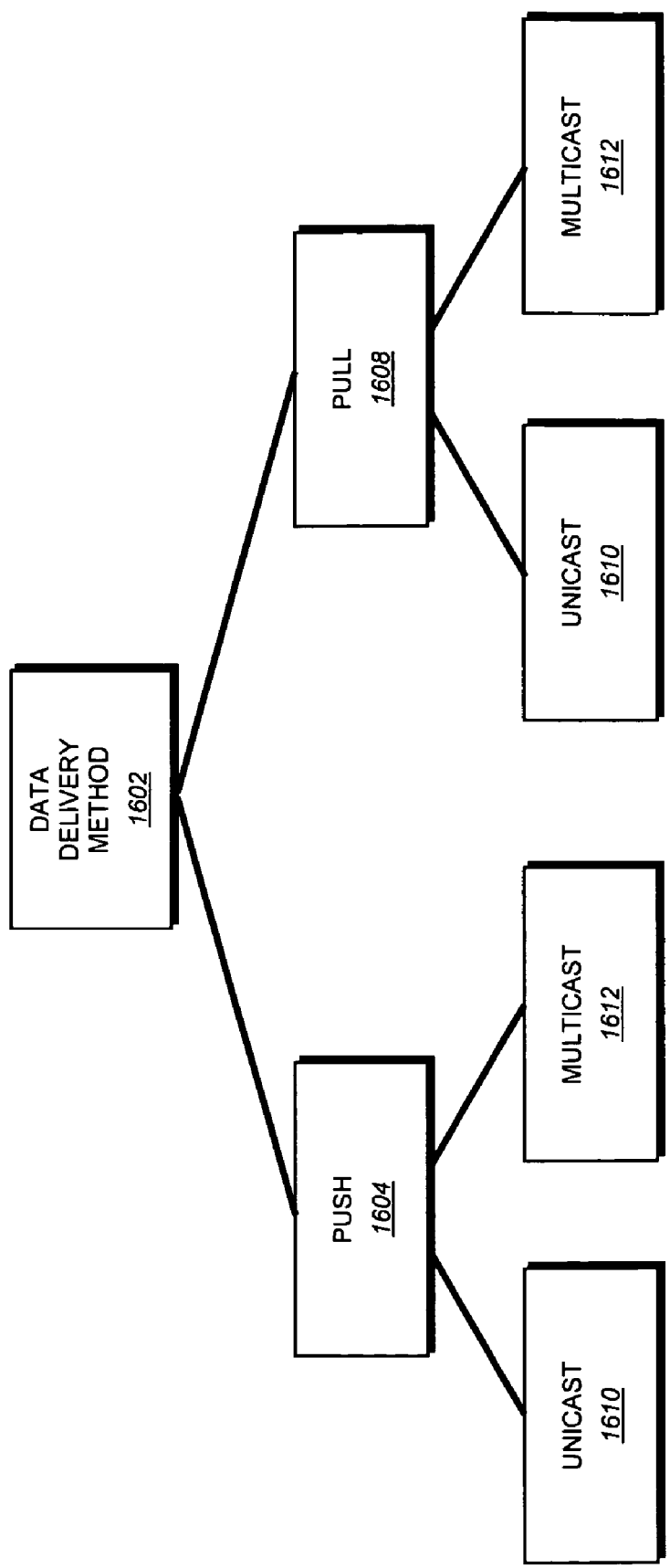

FIG. 16 shows various data delivery methods that may be used with enhanced syndication services described herein. Referring to FIG. 16, embodiments of Internet-based services typically employ a data delivery method 1602, which may include a push facility 1604, a pull facility 1608, a unicast facility 1610, and/or a multicast facility 1612. The push facility 1604 or the pull facility 1608 may include the unicast facility 1610 or the multicast facility 1612. In embodiments and without limitation, the unicast facility 1610 may include TCP/IP, the multicast facility 1612 may include UDP/IP, the push facility 1604 may include RTP or SMTP, and/or the pull facility 1608 may include HTTP. It should be appreciated that the push facility 1604, the pull facility 1608, the unicast facility 1610, and/or the multicast facility 1612 may include any suitable standardized or proprietary protocol.

An instance of the data delivery method 1602 may be specified in terms of a type. Without specifying a particular implementation, the type may indicate whether the instance of the data delivery method 1602 includes the push facility 1604, the pull facility 1608, the unicast facility 1610 and/or the multicast facility 1612. The depicted types include: push, pull, unicast, multicast, unicast/push, unicast/pull, multicast/push, multicast/pull.

Without limitation, in embodiments, a unicast/push instance of the data delivery method 1602 may include as an SMTP-over-TCP/IP session, a unicast/pull instance of the data delivery method 1602 may include an HTTP-over-TCP/IP session, a multicast/push instance of the data delivery method 1602 may include an RTP-over-UDP/IP session, and/or a multicast/pull instance of the data delivery method 1602 may include a session of a facility that pools a plurality of identical pull requests and transmits a single response to the requests via a multicast channel.

In some embodiments, the type of the instance of the data delivery method 1602 may be static, for example and without limitation an entry in a configuration file may specify that the type is to be unicast/pull.

In other embodiments, the type of the instance of the data delivery method 1602 may be dynamic and thus may vary from time to time. For example and without limitation, it should be appreciated that an influx of a plurality of requests from one of more client facilities via the unicast/pull instance of the data delivery method 1602 may overload a server facility attempting to service the plurality of requests. This overload may result in delayed or denied service to the one or more client facilities. Likewise, it is should be appreciated that the multicast/push instance of the data delivery method 1602 may be used to provide service to the one or more clients in anticipation of the plurality of requests, perhaps obviating the need for the plurality of requests and concurrently eliminating the potential overload that may occur in the unicast/pull instance. It follows that, from time to time and in some embodiments, changing the type of the instance of the data delivery method 1602 from unicast/pull to multicast/push may avert an impending overload. Generally, systems according to the present invention may support any suitable dynamic substitution of one type of the instance of the data delivery method 1602 for another type of the instance of the data delivery method 1602.

It will be appreciated that the distinction between push and pull communications may become blurred in a system such as contemporary RSS networks, where a "pinger" provides update information on RSS channels, which may be used by an RSS intermediary, such as an aggregator, to simulate push by signaling to readers when new content is available, even where the content sources is, strictly speaking, a pure pull source that simply provides channel items in response to requests.

In the following discussion of FIGS. 17-24, a single-headed arrow may indicate an instance of the data delivery method 1602. The direction of the arrow may indicate the direction in which the S-message is usually transferred but may not imply the type of the instance of the data delivery method 1602. A line without an arrowhead may indicate an association between two depicted components, but may not imply how that association is implemented or whether the two components are operatively coupled. In one aspect, FIGS. 17-24 characterize operations of the syndication layer 414 of an enhanced syndication services system.

Figure 17:
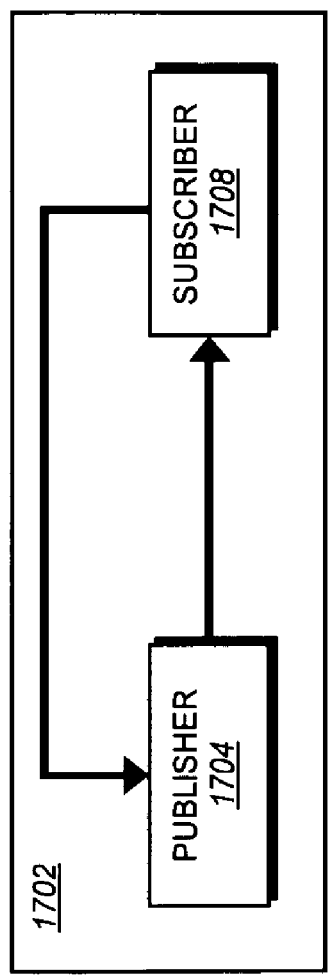

Referring to FIG. 17, a publish/subscribe facility 1702 may include a publisher 1704, which may be, for example the server 104 of FIG. 1 and/or the content source 204 of FIG. 2, and a subscriber 1708, which may be, for example, the client 102 of FIG. 1. The publisher 1704 may include any suitable facility and/or facilities for (1) providing original data; (2) embodying an instance of the original data as an S-message ("the original S-message"); (3) transmitting the original S-message via a network that may be connected to the publisher 1704 ("the publisher's network"); and, optionally, (4) receiving a subscriber's subscription request via the publisher's network. The subscriber 1708 may include any suitable facility and/or facilities that may be capable of (1) receiving the original S-message via a network that may be connected to the subscriber 1708 ("the subscriber's network") and (2) transmitting the subscriber's subscription request via the subscriber's network.

The publisher's network and the subscriber's network may be without limitation IP-based networks. The publisher network may be the same as the subscriber network. Alternatively, the publisher network may be connected to the subscriber network via at least one other network, such as and without limitation the Internet.

Figure 18:
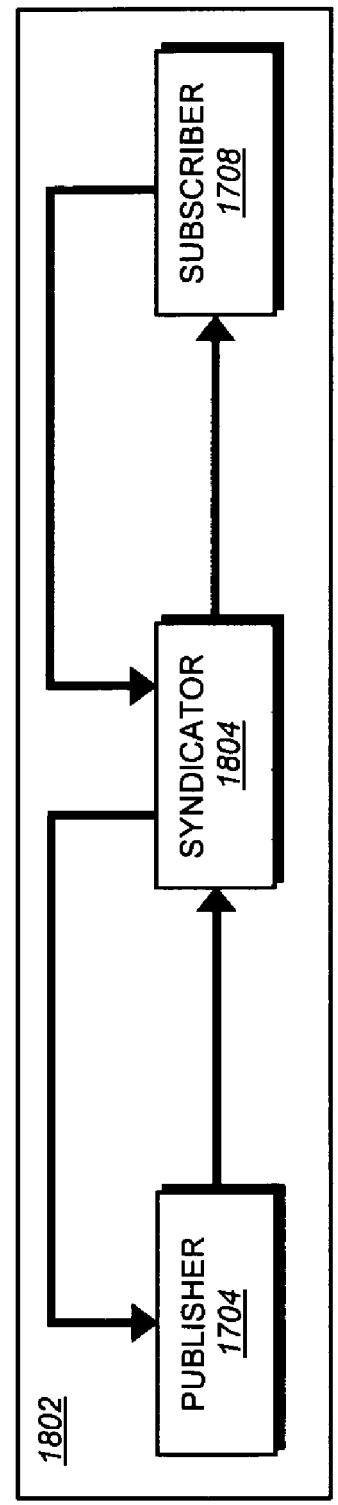

Referring to FIG. 18, a syndication facility 1802, which may be capable of providing Internet syndication, may include the publisher 1704, a syndicator 1804, and the subscriber 1708. The syndicator 1804 may include any suitable facility and/or facilities that may be capable of (1) receiving the original S-message via a network that may be connected to the syndicator 1804 ("the syndicator's network"); (2) providing syndicated data, which may be associated with the original data; (3) embodying an instance of the syndicated data as an S-message ("the syndicated S-message"); (4) transmitting the syndicated S-message via the syndicator's network; (5) receiving the subscriber's subscription request via the syndicator's network; and (6) transmitting a subscription request ("the syndicator's subscription request") via the syndicator's network. The publisher 1704 may further include any suitable facility and/or facilities that may be capable of receiving the syndicator's subscription request.

The syndicated data may include a real-time version of the original data and/or a time-delayed version of the original data. In any case, the version of the original data may include a verbatim reproduction of the original data; a partial reproduction of the original data, which may without limitation represent a shortened, abbreviated, abridged, digested, summarized, and/or truncated version of the original data; a modified instance of the original data, such as and without limitation a translation of the original data into another language; and/or an instance of data generated by a process that may have used the original data as an input. This process may without limitation include a user behavior analyzer, a product reviewer, and/or an aggregator.

The syndicator's network may without limitation be an IP-based network. The syndicator's network may be the same as the subscriber's network and/or the publisher's network. Alternatively, the syndicator's network may be connected to the subscriber's network and/or the publisher's network via at least one other network, such as and without limitation the Internet.

Referring to FIG. 19, the publisher 1704, as described above, may include a number of suitable facilities for providing real time, quasi-real time, scheduled, or ad hoc data 1902 for one or more of time, maps, weather, weather forecasts, sensors, merchants, advertisers, authors, blogs, and so forth. The publisher 1704 may employ a data delivery method 1602 including various network interfaces, protocol stacks, message encapsulations (e.g., as an S-message or an RSS item), and the like. Similarly, a subscription request and/or the subscriber may employ various identical, similar, or different data delivery methods 1602.

Referring now to FIG. 20, the subscriber 1708, as described above, may be capable of both receiving the original S-message and transmitting a subscription to, e.g., a publisher 1704. The subscriber may locally store data 1902 received in the form of syndicated content and any attachments thereto.

Referring now to FIG. 21, the subscriber 1708 may, in embodiments, be associated with a subscriber's agent 2102. The subscriber's agent may include any suitable facility and/or facilities that may be capable of (1) suggesting a subscriber's subscription request on behalf of the subscriber 1708 and (2) transmitting this subscriber's subscription request either via the subscriber's network or via a subscriber's agent's network.

The subscriber's agent's network may without limitation be an IP-based network. The subscriber's agent's network may be the same as the subscriber's network and/or the syndicator's network. Alternatively, the subscriber's agent's network may be connected to the subscriber's network and/or the syndicator's network via at least one other network, such as and without limitation the Internet.

Figure 22:
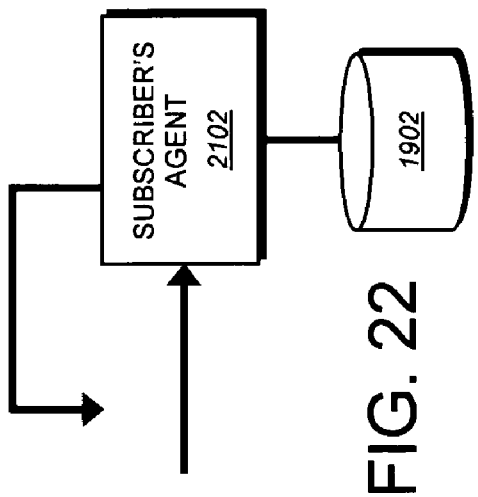

Referring now to FIG. 22, the subscriber's agent 2102, may, for example, search data feeds and suggest new subscriptions, or automatically generate new subscription requests according to user specifications. This may include, for example, a collaborative filtering algorithm that compares a set of third-party or community subscription requests to a set of subscription requests for the subscriber 1708. This comparison may provide a suggestion of a channel that may be of interest to the subscriber 1708. It should be appreciated that, in some embodiments, the subscriber's agent 2102 and the subscriber 1708 may be implemented on the same machine.

Figure 23:
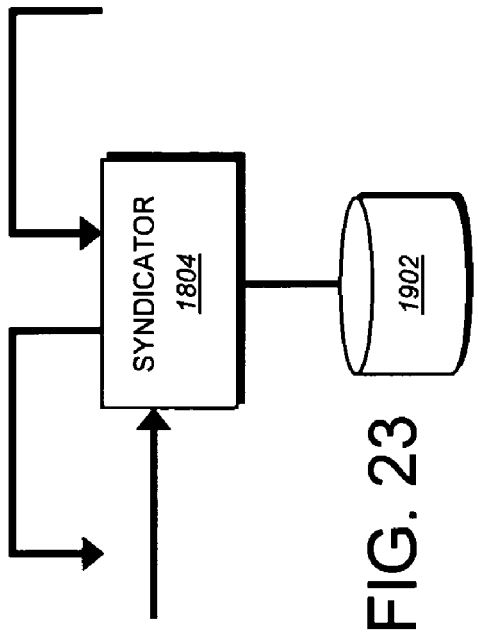

Now referring to FIG. 23, the syndicator 1804, may provide various syndication functions. This may include, for example, receiving S-messages from publishers 1704, processing subscription requests, and publishing new feeds to subscribers 1708. The syndicator 1804 may also process syndicated content under parameters provided by a subscriber 104, including, for example, aggregating a number of channels, filtering individual messages or items within a channel, or publishing subscriber-created aggregate and/or filtered feeds for subscription by third parties.

Figure 24:
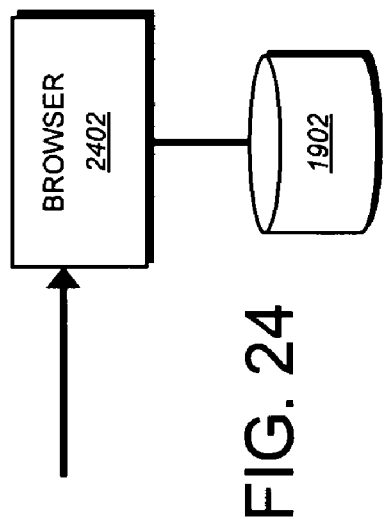

Now referring to FIG. 24, a browser 2402 may display S-messages on a client device using, for example, a default format, a device-specified format, a message specified format, a user specified format, or any combination of these. The browser 2402 may also, or instead, provide local channel selection, filtering, and the like, and may include user interface tools for a user to, e.g., search and select new feeds, configure filters, publish new content or aggregated feeds, and so on.

FIG. 25 shows an example of a syndication message. For the purposes of illustration and without limitation, an instance of an S-message as depicted in FIG. 25 may include various combinations of nested, recursive, hierarchical, referential, or other elements according to the purpose and/or subject matter thereof. An S-message may include, for example, one or more OPML elements, as indicated by the type attribute of the <BODY type="OPML" . . . > element. This element may include any OPML-compliant content or metadata, such as associated <head>, <body>, or <outline> elements. Furthermore, as has been discussed, an S-message may include one or more RSS elements, as indicated in the figure by a <CHANNEL> element, along with any RSS-compliant content or metadata. It should be appreciated that the use of arbitrary elements within an <OUTINE> element, as illustrated, may allow for the arbitrary and unlimited nesting of various elements within an outline.

When an S-message includes more than one element, the elements may be nested and/or grouped. This nesting and/or grouping may or may not be associated with an outline. While a specific example of an S-message is depicted herein, it will be appreciated that other general forms are possible, including forms that contain only RSS, only OPML, or neither of these, as well as various combinations of any of the foregoing, including variations that use elements of RSS and/or OPML in ways that are not compliant with RSS and/or OPML standards. All such combinations are intended to fall within the scope of an S-message, and may be used in any of the syndication or other systems described herein.

Now referring to FIG. 26, an instance of an S-message may include a version history. The <FILESET> element may contain one or more <FILE> elements, which may be representative of the names of one or more associated files. The <SYMBOLICREVISION> element may contain <FILE> elements with id attributes indicating the id or version of the corresponding files that may be associated with a particular symbolic revision. In this example, the symbolic revision indicates which versions of the files in the <FILESET> were "sent to the customer." In embodiments, any number of <SYMBOLICREVISION> elements may be present. There may exist one <REVISIONHISTORY> element associated with each <FILE> in the <FILESET>. The <REVISIONHISTORY> may contain any number of <REVISION> elements. Each <REVISION> element may be representative of a particular revision of the associated file. It should be noted that each <REVISION> may contain a <FILE> element specifying the name, identifier, and/or location of the file containing that revision of the associated file. In this example, it should be appreciated that revision 1.2 of the patent.doc file is stored in a file named "patent.doc.1.2" and that revision 1.1 of the patent.doc file is stored at "http://www.bigarchive.com/patent.doc.1.1". In the <VERSIONHISTORY> for the patent.xls file, it is shown that revision 1.2 of the file is the result of a merge between revisions 1.1.1 and 1.1 of the file. Revision 1.1.1 is itself the result of a branch from revision 1.1.

Generally, the version history may support a representation of a manual revision, an automatic revision, a branch, a merge, a tag or symbolic revision, an attribute or element representative of a type of revision (for example, whether the revision is manual or automatic), a set of associated files across which a tag or symbolic revision may be applied, and so forth. For example, revision 1.2 of the patent.doc file is shown to be an automatic revision caused by a software crash event. It should be appreciated that this S-message may be considered to be a list and, in particular, the revision history elements may be considered to be outlines.

In embodiments, aspects of the syndication facility 1802 may be presented to an application developer in the form of a syndication service API. This syndication service API may include software interfaces allowing the application developer to access one or more syndication services. A syndication service may without limitation create, publish, and/or subscribe to the message instance 1408, an entry, an outline, a list, the data feed 1502, a channel definition, an aggregate channel, and so forth. The application developer may use the syndication service API to develop an application that may utilize one or more of the syndication services. In embodiments, without limitation, the syndication services may be implemented in an operating system, in a database management system, in a user-level process on a client, in a user-level process on a server, as a Web service, and so forth. In the case that the API is implemented in a user-level process on a client, the interface between the application and the user-level process may be a socket through which one or more S-messages may be passed. In this arrangement, an API stub in the application may translate into an S-message the application's method call or function call to the API. The S-message may then be forwarded to the user-level process for action. In the case that the API is implemented as a Web service, the interface between the application and the Web service may be an HTTP session over which one or more S-messages may be passed via SOAP. In the case that the API is implemented as a user-level process on a server, the interface between the application and the user-level process may be a TCP/IP socket over which remote procedure calls are passed. In the case that the API is implemented in a database management system, the interface between the application and the user-level process may include XQUERY messages. Alternatively, the database management system may include an integral implementation of the API, which may without limitation be accessed as a Web service.

Now referring to FIG. 25, for the purposes of illustration and without limitation, an instance of an S-message may include various combinations of nested, recursive, hierarchical, referential, or other elements according to the purpose and/or subject matter thereof. As has been discussed, an S-message may include one or more OPML elements, as indicated by the type attribute of the <BODY type= "OPML" . . . > element. This element may include any OPML-compliant content or metadata, such as associated <head>, <body>, or <outline> elements. Furthermore, as has been discussed, an S-message may include one or more RSS elements, as indicated in the figure by a <CHANNEL> element, along with any RSS-compliant content or metadata. It should be appreciated that the use of arbitrary elements within an <OUTINE> element, as illustrated, may allow for the arbitrary and unlimited nesting of various elements within an outline.

When an S-message includes more than one element, the elements may be nested and/or grouped. This nesting and/or grouping may or may not be associated with an outline. While a specific example of an S-message is depicted herein, it will be appreciated that other general forms are possible, including forms that contain only RSS, only OPML, or neither of these, as well as various combinations of any of the foregoing, including variations that use elements of RSS and/or OPML in ways that are not compliant with RSS and/or OPML standards. All such combinations are intended to fall within the scope of an S-message, and may be used in any of the syndication or other systems described herein.

Now referring to FIG. 26, for the purposes of illustration and without limitation, an instance of an S-message may include a version history. The <FILESET> element may contain one or more <FILE> elements, which may be representative of the names of one or more associated files. The <SYMBOLICREVISION> element may contain <FILE> elements with id attributes indicating the id or version of the corresponding files that may be associated with a particular symbolic revision. In this example, the symbolic revision indicates which versions of the files in the <FILESET> were "sent to the customer." In embodiments, any number of <SYMBOLICREVISION> elements may be present. There may exist one <REVISIONHISTORY> element associated with each <FILE> in the <FILESET>. The <REVISIONHISTORY> may contain any number of <REVISION> elements. Each <REVISION> element may be representative of a particular revision of the associated file. It should be noted that each <REVISION> may contain a <FILE> element specifying the name, identifier, and/or location of the file containing that revision of the associated file. In this example, it should be appreciated that revision 1.2 of the patent.doc file is stored in a file named "patent.doc.1.2" and that revision 1.1 of the patent.doc file is stored at "http://www.bigarchive.com/patent.doc.1.1". In the <VERSIONHISTORY> for the patent.xls file, it is shown that revision 1.2 of the file is the result of a merge between revisions 1.1.1 and 1.1 of the file. Revision 1.1.1 is itself the result of a branch from revision 1.1. Generally, the version history may support a representation of a manual revision, an automatic revision, a branch, a merge, a tag or symbolic revision, an attribute or element representative of a type of revision (for example, whether the revision is manual or automatic), a set of associated files across which a tag or symbolic revision may be applied, and so forth. For example, revision 1.2 of the patent.doc file is shown to be an automatic revision caused by a software crash event. It should be appreciated that this S-message may include an OPML list and the revision history elements may be OPML outlines.

In embodiments, aspects of the syndication facility 1802 may be presented to an application developer in the form of a syndication service API. This syndication service API may include software interfaces allowing the application developer to access one or more syndication services. A syndication service may without limitation create, publish, and/or subscribe to the message instance 1408, an entry, an outline, a list, the Internet feed 1502, a channel definition, an aggregate channel, and so forth. The application developer may use the syndication service API to develop an application that may utilize one or more of the syndication services. In embodiments, without limitation, the syndication services may be implemented in an operating system, in a database management system, in a user-level process on a client, in a user-level process on a server, as a Web service, and so forth. In the case that the API is implemented in a user-level process on a client, the interface between the application and the user-level process may be a socket through which one or more S-messages may be passed. In this arrangement, an API stub in the application may translate into an S-message the application's method call or function call to the API. The S-message may then be forwarded to the user-level process for action. In the case that the API is implemented as a Web service, the interface between the application and the Web service may be an HTTP session over which one or more S-messages may be passed via SOAP. In the case that the API is implemented as a user-level process on a server, the interface between the application and the user-level process may be a TCP/IP socket over which remote procedure calls are passed. In the case that the API is implemented in a database management system, the interface between the application and the user-level process may include XQUERY messages. Alternatively, the database management system may include an integral implementation of the API, which may without limitation be accessed as a Web service.

Having described various aspects of an enhanced syndication system, the description turns now to a number of useful applications for such a system.

Figure 27:
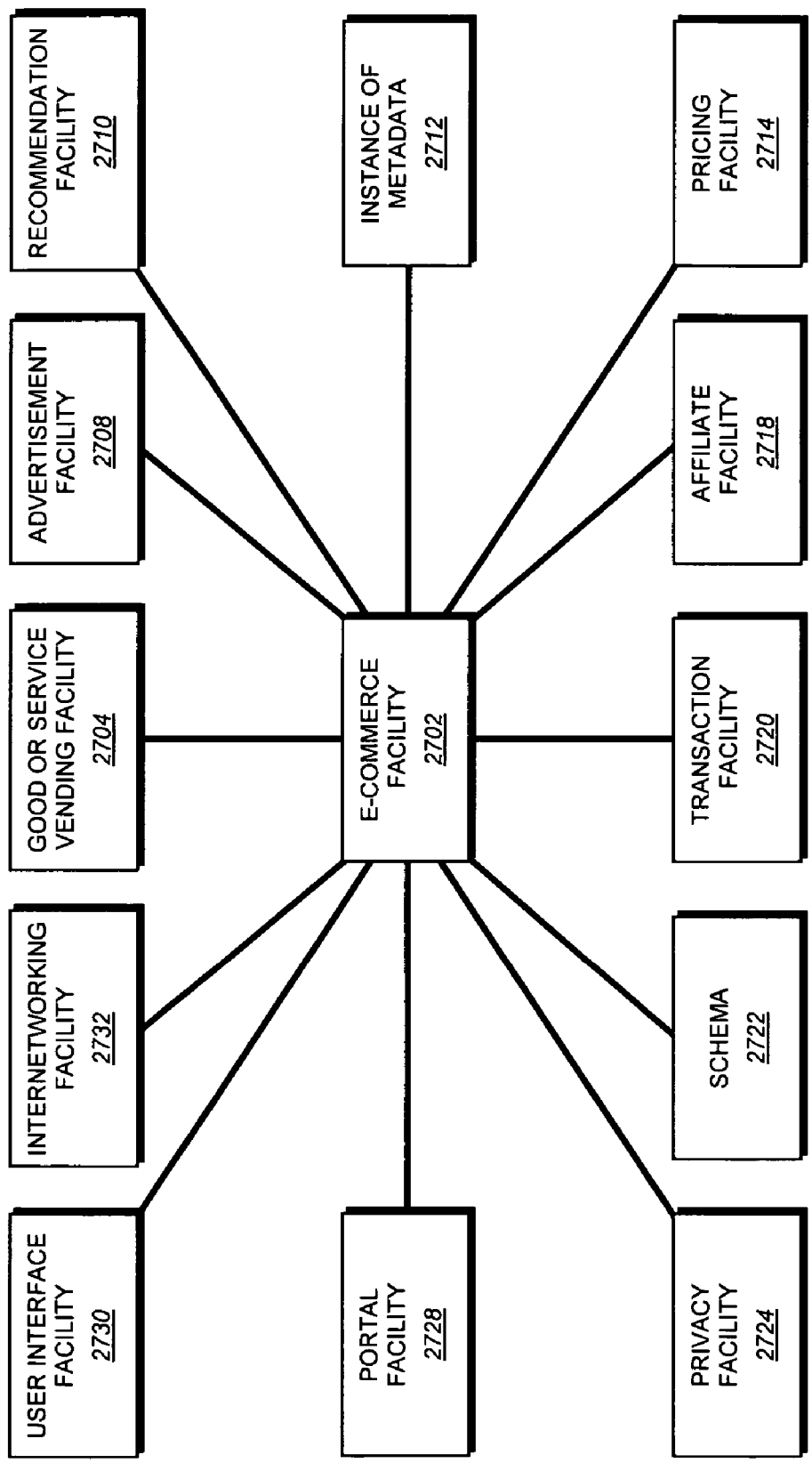
FIG. 27 shows an e-commerce system using syndication.

Referring to FIG. 27, syndication may be employed by an e-commerce facility 2702. The e-commerce facility 2702 may include a good or service vending facility 2704; an advertisement facility 2708; a recommendation facility 2710; an instance of metadata 2712; a pricing facility 2714; an affiliate facility 2718; a transaction facility 2720; a schema 2722; a privacy facility 2724; a portal facility 2728; a user interface facility 2730; and/or an internetworking facility 2732.

The good or service vending facility 2704 may employ syndication to facilitate the sale of a good or service. Without limitation, the goods or services may fall into categories such as: adult, apparel, audio and video, automotive, baby, baby registry, wedding registry, beauty, bed and bath, books, camera and photo, cell phones and service, computer and video games, computers, digital books, DVDs educational electronics, financial services, friends and favorites, furniture and décor, food, gourmet food, health and personal care, home and garden images, information, jewelry and watches, magazine subscriptions, maps, movie show times, music, musical instruments, office products, outdoor living, pet supplies, pharmaceuticals, real estate, shoes, software, sports and outdoors, tools and hardware, toys and games, travel, video, weather, wish list, and/or yellow pages.

The advertisement facility 2708 may employ syndication to facilitate advertising. This may include one or more of the following: aggregation of advertisements, providing a Web site containing only advertisements, attention brokering, bidding to advertise, communication with an end user, a coupon, dynamically inserting an advertisement, an association between an editor and an advertisement, permission-based advertising, a promotion, and/or commercial e-mail.

In one aspect, there is described herein an improved system for authoring RSS or other data feeds. The system may enable addition of any file or media type to an RSS feed, and may include tools for manual creation of individual posts, as well as automated, or semi-automated creation of RSS feeds that obtain source content from source repositories that may store, for example, headline items, advertising, multi-media interludes, segment bumpers, program introductions, channel or feed identifiers, and so on. The source repositories may be used sequentially, or may be accessed by a feed manager program that searches and selects from content of the available repositories according to user preferences, user contexts, or other explicit or implicit information from which relevance and/or appropriateness of selections might be determined. In one example, a source file may include a number of pre-authored items, such as news items, that are interleaved in a random or repeating sequence with other content such as advertisements, breaking news, daily headlines, other aggregator or source output, and so on. This may be combined, for example, with advertisements from the advertisement facility 2708, which may include Google Adsense or one or more other advertising technologies that provide contextualized advertisements for users. The advertisement facility 2708 may allocate revenue or otherwise move money among participants in an RSS system. Revenue for paid advertisements may be automatically transferred to appropriate entities, such as a publisher of content that had an advertisement associated therewith.

The advertising facility 2708 may include hardware and/or software for integrating advertisements into RSS feeds on the basis of, for example, user context, content of RSS posts, and so on. Advertisers may pay for placement of advertisements, and resulting advertisement revenue may be paid to an RSS feed source or author of an item that includes the advertisement, or revenue may be distributed among the RSS item/feed source, an aggregator that provides the item to an end user, or any other producers, providers, advertisers, or other participants in the RSS system, or some combination of these. Revenue allocation may be embedded into each RSS advertisement item, and in certain embodiments, the payment itself may be embedded into the advertisement and allocated to various parties through an automated advertisement revenue allocation system.

In another aspect, a data stream item, such as an RSS item, may contain an embedded payment, such as digital currency, that may be secured and authenticated using known cryptographic techniques, or the RSS item may include a secure and/or authenticated reference to a payment transaction system that completes payment transactions according to instructions embedded in the RSS item, or provided by the advertising facility 2708. In one embodiment, such a system may be used to support paid advertising in an RSS network. In another embodiment, such a system may be used to support personal financial transactions including interpersonal payments among private parties, or bill payment services. In another embodiment, such a system may be used to support subscriptions or pay-as-you-go access to RSS content of interest. These and other applications of an RSS-based financial transaction system are intended to fall within the scope of the systems described herein.

In one aspect, a person may register with a web site such as that described above to be a publisher or author of content, such as syndicated content. The registration may automatically, or at the option of the user, additionally register the user with the advertisement facility 2708, which may include any third-party advertisement service, such as Google AdSense, or an advertisement service offered directly by the host of the web site. The author's content may then be published with advertisements inserted from the advertisement facility 2708, with fees paid according to click-throughs or some other user action. The advertisement revenues may be allocated within the syndication network (or other content distribution system), such as by sharing revenues among an author, a host (such as the website above), aggregators or other intermediate distributors, and so on. An advertising revenue sharing system may automatically allocate revenues according to any suitable algorithm, or according to explicit, negotiated fee sharing agreements. The system may automatically distribute payment using, for example, the security and financial transaction systems described above. In one aspect, a user may automatically specify some or all of the advertising revenue from paid advertisements to be reallocated to purchasing advertisements for the user, which may be dispensed to acquire advertising for the author in other channels.

The recommendation facility 2710 may employ syndication to facilitate the generation and/or delivery of a recommendation. Without limitation, this facilitation may be associated with one or more of the following: buying-based behavior, click-based behavior, collaborative filtering, customer reviews, editorial reviews, machine learning, and/or reputation measures. It should be appreciated that the recommendation may be directed toward a consumer, a manufacturer, a vendor, a third party, or any other suitable recipient of the recommendation.

The pricing facility 2714 may employ syndication to facilitate the generation and/or modification of a price. Without limitation, this facilitation may include one or more of the following: an agent or bot, an auction, a catalog aggregator, a pricing comparison engine, a rating, and/or a reverse auction.

The affiliate facility 2718 may employ syndication to facilitate an e-commerce affiliate or affiliate network. Without limitation, this facilitation may include one or more of the following: an affiliate program.

The transaction facility 2720 may employ syndication to facilitate a transaction. Without limitation, this facilitation may include one or more of the following: one-click shopping, an anti-piracy measure, an auction, an authentication, a "buy now" facility, a shopping cart, a currency transaction or exchange, a digital rights management facility, a mart, an object-oriented transaction-model, a PayPal account or transaction, a permission, a micropayment, a cryptographic key distribution facility or key management facility, a security facility, an item of stored information, a profile, a transaction processing facility, and/or an authority verification facility.

The schema 2722 may include the S-definition. Without limitation, the schema 2722 and/or elements within the schema 2722 may be associated with one or more of the following: a firewall, a library, an object-oriented representation, a persistent item, security, a virus scan, a Web service, a service-oriented architecture, and/or XML.

The privacy facility 2724 may employ syndication to facilitate a privacy feature. Without limitation, the privacy feature may include one or more of the following: blocking an advertisement, providing permanent anonymity, providing temporary anonymity, and/or preventing or blocking spam.

The portal facility 2728 may employ syndication to facilitate a portal. Without limitation, the portal may include and/or be associated with one or more of the following: a syndication service provider, an RSS ISP, a subject matter, Yahoo!, an OPML or RSS database, and the like.

The user interface facility 2730 may employ syndication to facilitate a user interface. Without limitation, the user interface may include and/or be associated with one or more of the following: a media player, a Web facility, a mobile Web facility, a secure device, and/or a skin.

Figure 28:
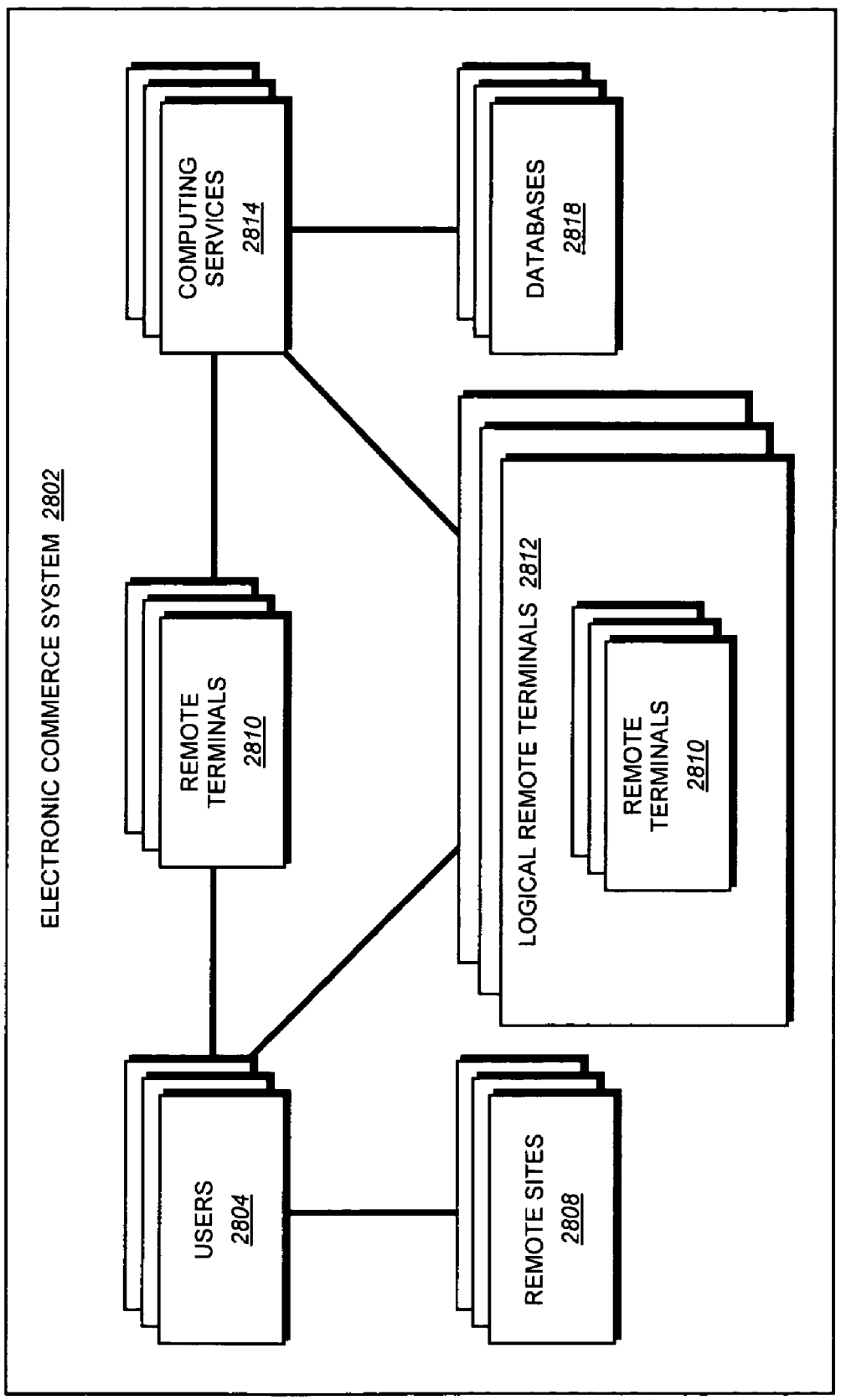
FIG. 28 shows aspects of an electronic commerce system.

FIG. 28 shows aspects of an electronic commerce system 2802, which may provide interactive communications and processing of business transactions between users 2804. The system 2802 may permit users 2804 such as buyers, sellers, etc. at remote sites 2808 to conduct business transactions and communicate with databases 2818 associated with other computing services 2814 from a variety of remote terminals 2810. The communication with the databases 2818 may without limitation involve an SQL query, an XQuery query, a tier in an n-tier architecture, and/or a Web service. Generally, the remote terminals 2810 may include a processor; a memory (such as RAM, Flash, EEPROM, or any other suitable computer memory); a bus that couples the processor and the memory; an optional mass storage device (such as and without limitation a fixed magnetic disc, a removable magnetic disk, a flash memory device, a EEPROM, a ROM, a RAM, a fixed optical device or disc, a removable optical device or disc, a holographic device or disc, removable quantum memory device, a fixed quantum memory device, a tape, a punch card, or any other suitable memory device or disc) coupled to the processor and the memory through an I/O controller; and a communications interface (as described below) coupled to the processor and the memory.

In some embodiments, the users 2804 may include and employ humans to interact with the electronic commerce system 2802. The humans may manually conduct the business transactions and communicate with the databases 2818 via the remote terminals 2810.

In other embodiments, the users 2804 may include and employ automatic computers to interact with the electronic commerce system 2802. In this case, the users 2804 may constitute the remote terminals 2810. The automatic computers may, as the remote terminals 2810, programmatically or automatically conduct the business transactions and communicate with the databases 2818.

In any case, the remote terminals 2810 may without limitation include a personal computer, a workstation, a server, a blade server, a mobile computer (such as and a laptop, a personal digital assistant, a portable media player, and so forth), a cellular phone, a television set-top box, a videogame console, an interactive kiosk, a thin client, a dumb terminal or ASCII terminal, a display device (such as an LED display, a plasma display, an LCD display, a digital projector, a CRT display, a holographic display, and so forth), a digital advertising display (which may include a display device or any other suitable electronic display employed to deliver an advertising message in a public or private space), and so forth.

In some embodiments, it may be advantageous to combine one or more of aforementioned remote terminals 2810 into logical remote terminals 2812, which may perform as remote terminals 2810 in the system. This may be particularly true in the case where the users 2804 are humans. For example and without limitation, a digital advertising display, which may provide output to a user, may be used in conjunction with a cellular phone, which may capture input from the user. Together, the digital advertising display and the cellular phone may behave as one of the logical remote terminals 2812, which may perform as one of the remote terminal 2810.

Since the logical remote terminals 2812 may function as remote terminals 2810, it should be appreciated that any reference to the remote terminals 2810 may be read as a reference to both the remote terminals 2810 and the logical remote terminals 2812, and vice versa.

In embodiments, some of the remote sites 2808 may include remote computer systems through which operators, who may be the users 2804 or may be associated with the users 2804, may communicate with the remote terminals 2810. Alternatively or additionally, some of the remote sites 2808 may include automatic computer systems, which may communicate with the remote terminals 2810. These automatic computer systems may include mass storage devices for storage of remote databases. Alternatively or additionally, some of the remote sites 2808 may simply include the remote terminals 2810 and the users 2804.

The users 2804 may include market participants in an interactive market that may be facilitated by the electronic commerce system 2802. Generally, the users 2804 may include a wide variety of market participants in an industry market as well as other service providers and interested parties. The users 2804 who gain full access to the services 2814 of the electronic commerce system 2802 may have all of the services 2814 of the electronic commerce system 2802 available to them. The users 2804 who gain full access to the services 2814 of the electronic commerce system 2802 may without limitation include market participants such as and without limitation sellers (such as distributors and suppliers), buyers, freight service providers, financial service providers, commercial service providers, information service providers, and proprietary service providers.

The users 2804 who have only gained partial access to the services 2814 of the electronic commerce system 2802 may only gain access to the services 2814 to which they are authorized to have access. The users 2804 who gain partial access to the services 2814 of the electronic commerce system 2802 may without limitation include affiliates, market analysts, shopping comparison services, consumer reporting agencies, governmental regulators, and so forth.

Some or all of the users 2804 may provide some or all of the computing services 2814 and/or some or all of the databases 2818. To these computing services 2814 and/or databases 2818, these users 2804 may authorize some or all of the users 2804 to have access.

Referring to FIG. 29, the remote sites 2808 may communicate with a central processing facility 2904, which may provide the computing services 2814 and/or the databases 2818, both of which are described hereinbefore with reference to FIG. 28.

The central processing facility 2904 may include a central processing unit coupled to a communications interface and a mass storage system. The central processing unit may provide a local processing capability. The mass storage system may include a local mass storage device and or a remote mass storage device. In any case, the mass storage system may store a central database, which may include at least one of the databases 2818. The central database may include a relational database management system, a stream database management system, a row-optimized database management system, a column-optimized database management system, a distributed database management system, a remote database management system, an XML database management system, a flat file system, an object relational database management system, or any other suitable database management system.

Communications interfaces may, without limitation, include network interfaces and may provide operative coupling to an electronic network facility 2902 through which the remote terminals 2810, perhaps on behalf of the users 2804, may access the central processing facility 2904 and/or its mass storage system. This access may avail the user 2804 of the computing services 2814 and/or the databases 2818. Likewise, through an electronic network facility 2902, the central processing facility 2904 may be operatively coupled to another central processing facility 2904, which may be included in the electronic commerce system 2802 or may be included in another electronic commerce system 2802, as shown. This operative coupling may allow the user 2804 of one central processing facility 2904 in one electronic commerce system 2802 to access another central processing facility 2904 and/or another electronic commerce system 2802. In other words, the electronic commerce system 2802 may be linked to other electronic commerce systems 2802.

The operative coupling provided by the communications interfaces may without limitation include a wired physical network connection, a wireless physical network connection, a network socket, a logical network port, a dial-up modem, or any other suitable physical or logical network or communications connection. The operative coupling between the electronic network facility 2902 and the other facilities may facilitate a communication of information such as syndication content, as described here and in the documents incorporated herein by reference.

The electronic network facility 2902, without limitation, may be an internet, an extranet, a local area network, a virtual local area network, a metropolitan area network, a wide area network, a public network, a private network, a virtual network, a virtual private network, a secure network, an insecure network, an packet network, an asynchronous packet network, a synchronous packet network, a circuit switched network, an analog network, an electronic network, a wired electronic network, a wireless network, a wireless radiofrequency network, a wireless microwave network, a wireless or free space optic network, an optical network, a fiber optic network, an encrypted network, a quantum encrypted network, a point-to-point network, a peer-to-peer network, an ad-hoc network, an infrastructure network, a contactless communication link, a contact communication link, and so forth.

Referring to FIG. 30, the electronic commerce system 2802 may provide the computing services 2814 in a syndication context, which may include an electronic commerce procedure and which may without limitation pertain to one or more of the following: a sale of a good or service, an advertisement, a recommendation, an instance of metadata, a price, an affiliate, a transaction, a schema, a privacy policy, a portal, a user interface, and/or a communication of information. It should be appreciated that a plurality of computing services 2814 may be provided simultaneously, such as according to multiprocessing, multithreading, and/or distributed computing techniques.

Computing services 2814 as they pertain to a sale of a good or service may, without limitation, relate to a good or service that may be generally recognized as belonging to one or more of the following categories: adult, apparel, audio and video, automotive, baby, baby registry, wedding registry, beauty, bed and bath, books, camera and photo, cell phones and service, computer and video games, computers, digital books, DVDs educational electronics, financial services, friends and favorites, furniture and décor, food, gourmet food, health and personal care, home and garden images, information, jewelry and watches, magazine subscriptions, maps, movie show times, music, musical instruments, office products, outdoor living, pet supplies, pharmaceuticals, real estate, shoes, software, sports and outdoors, tools and hardware, toys and games, travel, video, weather, wish list, and/or yellow pages.

Computing services 2814 as they pertain to an advertisement may, without limitation, include one or more of the following: aggregating advertisements; providing a Web site containing only advertisements; attention brokering; bidding to advertise; communicating with at least one of the users 2804; accepting, rejecting, issuing, processing, modifying, aggregating, redeeming, revoking, validating, distributing, or otherwise affecting or handling a coupon; accepting, rejecting, printing, processing, modifying, aggregating, canceling, validating, distributing, or otherwise affecting or handling a classified advertisement; dynamically inserting an advertisement, such as and without limitation into an item of electronic content; an association between an editor and an advertisement; permission-based advertising; a promotion; and/or commercial e-mail.

Computing services 2814 as they pertain to a recommendation may, without limitation, include generating and/or delivering a recommendation associated with one or more of the following: a buying-based behavior, a click-based behavior, collaborative filtering, customer reviews, editorial reviews, machine learning, and/or reputation measures.

Computing services 2814 as they pertain to an instance of metadata, which may include RSS metadata, OPML metadata, or S-definition metadata, may without limitation include one or more of the following: dynamic modification of user state, navigation, and/or navigation based upon based behavior.

Computing services 2814 as they pertain to a price may, without limitation, include generating, retrieving, storing, deducing, guessing, anticipating, and/or modifying the price in association with one or more of the following: an agent or bot, an auction, a catalog aggregator, a pricing comparison engine, a rating, and/or a reverse auction. In one aspect, the system described herein may be used to create an RSS-based (or other syndication-technology-based) auction platform. In such a system, a user may post an item for auction to a feed, including, for example, textual descriptions, photographs, drawings, technical specifications, product reviews, certificates of authenticity, or any other description materials, along with auction parameters such as minimum opening bid, bidding increments, an immediate purchase price, and the like. Participants may post bids, share messages, make inquiries to the seller, and otherwise communicate in the auction environment. The system may further support financial exchanges associated with an auction. In addition to managing the auction feed, the computer services 2814 may provide business logic associated with the auction, such as pre-qualifying bidders, ensuring that bid requirements are met by new bids, and so on.

Computing services 2814 as they pertain to an affiliate may, without limitation, be associated with one or more of the following: an e-commerce affiliate, an affiliate network, and/or an affiliate program.

Computing services 2814 as they pertain to a transaction may, without limitation, include one or more of the following: one-click shopping, an anti-piracy measure, an auction, an authentication, a "buy now" facility, a shopping cart, a currency transaction or exchange, an instance of digital rights management facility, a mart, an object-oriented transaction model, a PayPal account or transaction, a permission, a micropayment, a cryptographic key distribution facility or key management facility, a security facility, an item of stored information, a profile, a transaction processing facility, and/or an authority verification facility.

Computing services 2814 as they pertain to a schema may, without limitation, be associated with one or more of the following: a firewall, a library, an object-oriented representation, a persistent item, a security policy, a virus scan, a Web service, a service-oriented architecture, the S-definition provided above, and/or XML.

Computing services 2814 as they pertain to a privacy policy may, without limitation, include one or more of the following: blocking an advertisement, providing permanent anonymity, providing temporary anonymity, and/or preventing or blocking spam.

Computing services 2814 as they pertain to a portal, without limitation, include and/or be associated with one or more of the following: a syndication service provider, a syndication content provider, a syndication content reader, an item of syndicated subject matter, and so forth.

Computing services 2814 as they pertain to a user interface may, without limitation, include and/or be associated with one or more of the following: a media player, a Web facility, a mobile Web facility, a secure device, and/or a skin.

In the following descriptions of figures that show generalized flow diagrams, the direction of normal processing flow may be shown with arrows, with the flow proceeding from a logical block at an arrow tail to a logical block at the arrow's head. In the special cases where a logical block labeled END: RETURN appears, however, the direction of normal processing flow may be momentarily reversed: This logical block may indicate the return of processing flow to a preceding logical block. The textual description of each END: RETURN logical block, as disclosed hereinafter, will clearly indicate the logical block to which processing flow may return. From this return point, processing flow may proceed in the normal direction.

Also, in the following descriptions of figures that show generalized flow diagrams of procedures, it should be understood that the diagrams might illustrate methodologies and structural flows for specific embodiments of the procedures. Thus, it should be appreciated that numerous other embodiments of the procedures may be possible, including various orders of the depicted steps, as well as procedures that omit steps or add additional steps, or perform one or more steps in parallel, or various combinations of these.

Figure 31:
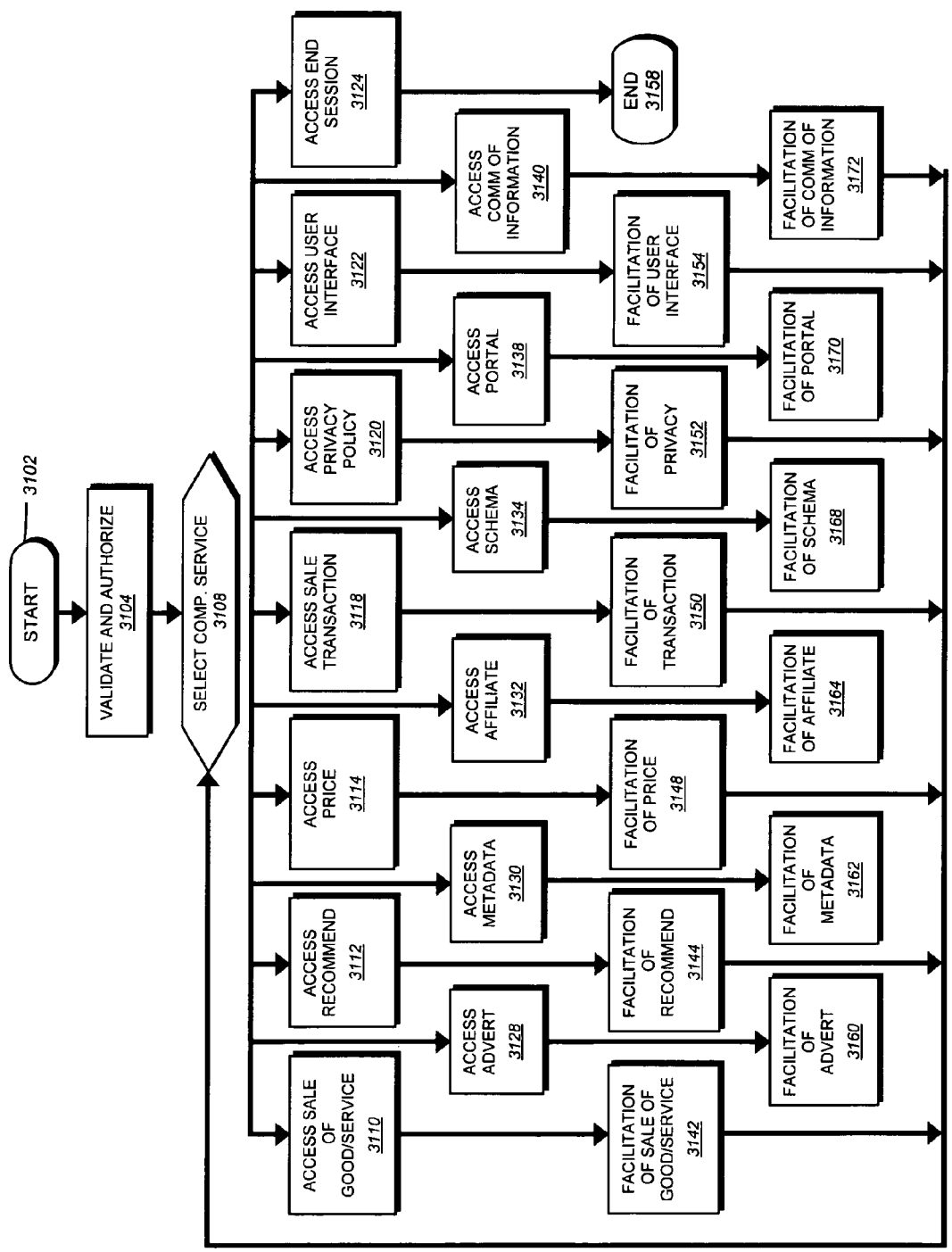
FIG. 31 shows a process for conducting electronic commerce.

Referring now to FIG. 31, there is shown an electronic commerce procedure of a specific embodiment of the electronic commerce system 2802. Starting at the top of the figure, one of the users 2804 ("the user") may enter a start of electronic commerce procedure (shown as the START logical block 3102), which is described hereinafter with reference to FIG. 32. Subsequently, processing flow may continue to a validation and authorization procedure (shown as the VALIDATE AND AUTHORIZE logical block 3104), which is described hereinafter with reference to FIG. 33. This procedure 3104 may provide the user with full access, partial access, or no access to the services 2814.

Processing flow may proceed to logical block 3108 (labeled SELECT COMP. SERVICE), as shown, wherein a test may be made to select which one of the computing services 2814 ("the service") may be provided by the electronic commerce system 2802 to facilitate electronic commerce for the user. This test is described hereinafter with reference to FIG. 34. As depicted, the logical blocks 3142, 3160, 3144, 3162, 3148, 3164, 3150, 3168, 3152, 3170, 3154, 3172, and 3158 may be representative of the services 2814 by which the electronic commerce system 2802 may facilitate electronic commerce for the user.

Processing flow may then proceed to a logical block that may be associated with the service and that may represent an access procedure. This logical block may be one of: an access procedure 3110 associated with a facilitation of a sale of a good and/or service 3142; an access procedure 3128 associated with a facilitation of an advertisement 3160; an access procedure 3112 associated with a facilitation of a recommendation 3144; an access procedure 3130 associated with a facilitation of metadata 3162; an access procedure 3114 associated with a facilitation of a price 3148; an access procedure 3132 associated with a facilitation of an affiliate 3164; an access procedure 3118 associated with a facilitation of a transaction 3150; an access procedure 3134 associated with a facilitation of a schema 3168; an access procedure 3120 associated with a facilitation of a privacy policy 3152; an access procedure 3138 associated with a facilitation of a portal 3170; an access procedure 3122 associated with a facilitation of a user interface 3154; an access facility 3140 associated with a facilitation of a communication of information 3172; or an access procedure 3124 associated with an end of the electronic commerce procedure 3158.

Each of the aforementioned access procedures (3110, 3128, 3112, 3130, 3114, 3132, 3118, 3134, 3120, 3138, 3122, 3140, and 3124) may provide an additional level of validation and authorization of the user. Thus, generally, after the test of logical block 3108 indicates the service, the user may be validated and authorized for access to the service. Subsequently, if validated and authorized, the processing flow may proceed to the service's facilitation logical block (3142, 3160, 3144, 3162, 3148, 3164, 3150, 3168, 3152, 3170, 3154, 3172, and 3158), as shown.

Figure 51:
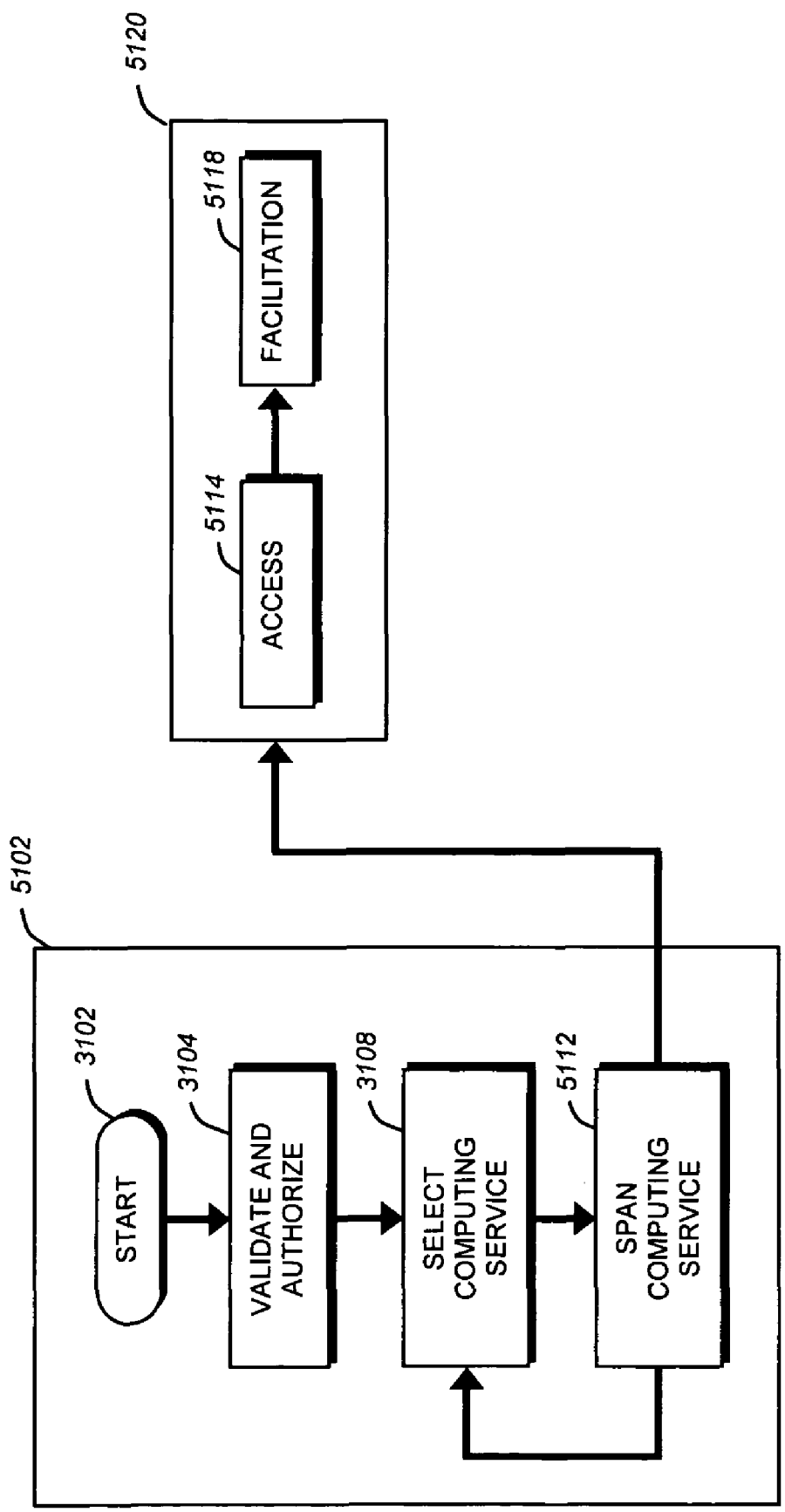
FIG. 51 shows a process for spawning a computer service.

Referring now to FIG. 51, there is shown a generalized flow diagram illustrating the methodology and structural flow for the electronic commerce procedure of a specific alternate embodiment of the electronic commerce system 2802 according to the invention. Starting at the top of the figure, the user may enter the start of electronic commerce procedure 3102, which may be within a computing process or thread 5102. Subsequently, the validation and authorization procedure 3104 may be followed. Processing flow may then proceed to logical block 3108 and then to the SPAWN COMPUTING SERVICE logical block 5112. This logical block may indicate the spawning of a computing process or thread 5120. As shown, the processing flow may proceed, perhaps in parallel, both into the process or thread 5120 and to the logical block 3108. Within the process or thread 5120, the processing flow may continue with the ACCESS logical block 5114, which may represent a particular access procedure, which may be one of the aforementioned access procedures (3110, 3128, 3112, 3130, 3114, 3132, 3118, 3134, 3120, 3138, 3122, 3140, 3124). Then, as shown, the processing flow within the spawned process or thread 5120 may conclude with the FACILITATION logical block 5118, which may one of the aforementioned facilitation logical blocks (3142, 3160, 3144, 3162, 3148, 3164, 3150, 3168, 3152, 3170, 3154, 3172, 3158) that is associated with the particular access procedure, wherein this association is as described hereinbefore with reference to FIG. 31. At the conclusion of the processing flow within the spawned process or thread 5120, the process or thread 5120 may terminate, suspend, and/or exit, with or without a status code.

Figure 32:
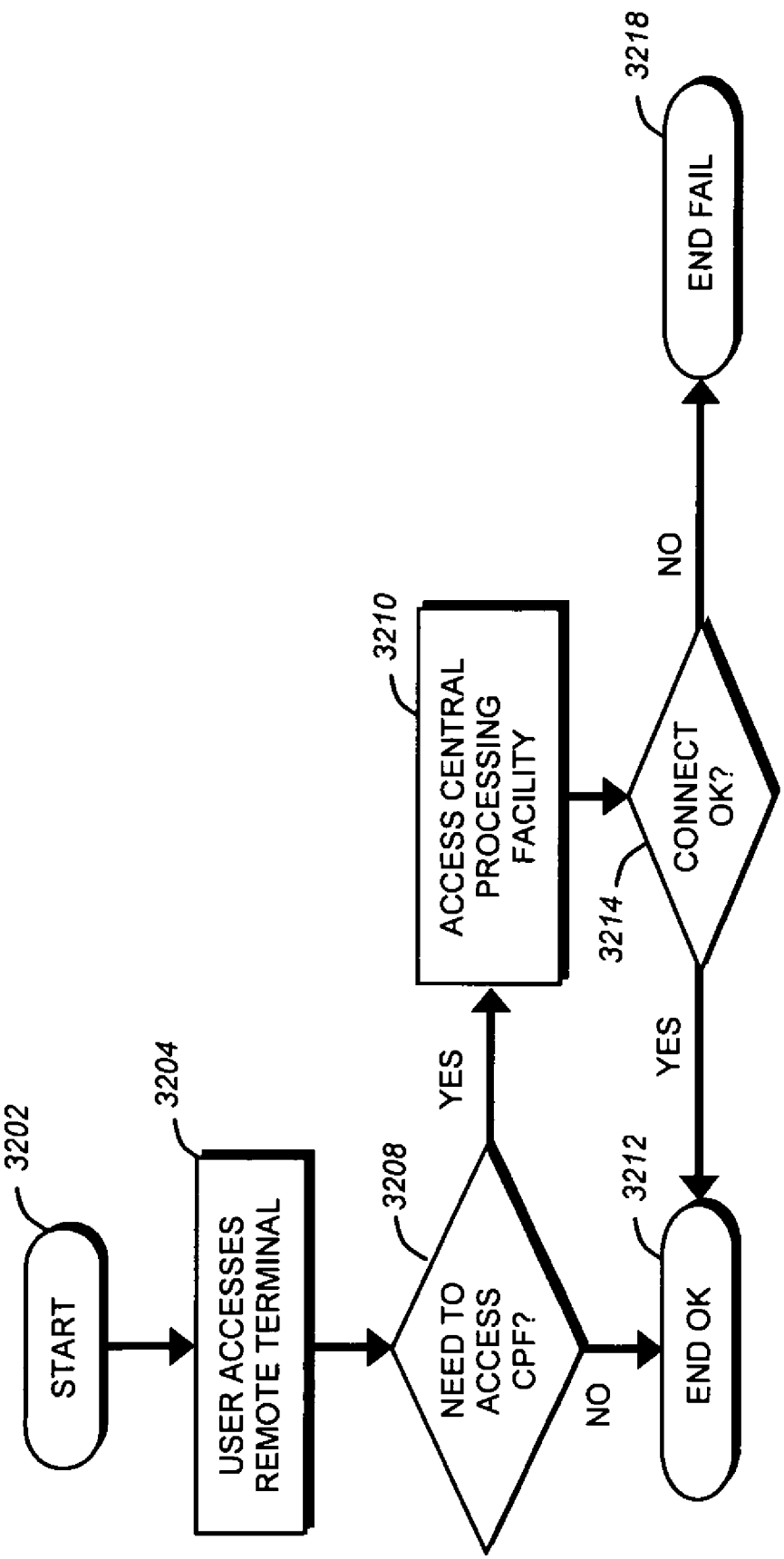
FIG. 32 shows a process for conducting electronic commerce.

Referring to FIG. 32, the start of electronic commerce procedure 3102 may begin with the logical block START 3202. Processing flow may proceed as shown, with the user perhaps accessing one of the remote terminal 2810 ("the remote terminal") in logical block 3204. In the case that the user is an automatic computer, this access may without limitation include either an automatic login to the remote terminal or the execution or interpretation of functionality at the automatic computer that may provide the remote terminal within the automatic computer. This execution or interpretation may without limitation be a function or method invocation, a launch of an executable, an interpretation of a script or set of byte-codes, and so forth. However, in the case that the user is a human, this access may include physical access, such as and without limitation by walking up to and physically interacting with a point-of-sale terminal that may be the remote terminal. Alternatively, this access may include virtual access such as and without limitation access to the remote terminal via a Web browser that may be operatively coupled to a Web server (such as by HTTP) that may be operatively coupled the remote terminal (such as by TCP/IP). In any case, processing flow may proceed to logical block 3208 where the remote terminal may conduct a test to see if it needs to access a central processing facility 2904. If the test results in a negative result, the remote terminal may already be accessing the central processing facility 2904 and processing flow may proceed to logical block END: OK 3212, where this may procedure end, perhaps producing a success code or other success indication. However, if the test results in an affirmative result, the remote terminal may attempt to access a central processing facility 2904, such as and without limitation by connecting to the central processing facility 2904. In some cases this attempt may fail, such as due to a busy signal, an excessive network lag, an unavailable network device or server, a software or hardware failure, a erroneously configured network device or server, and so forth. In these cases, processing flow may proceed to END: FAIL 3218, where the procedure may end, perhaps producing a failure code or other failure indication. Otherwise, the procedure may end at the aforementioned END: OK functional block 3212.

Figure 33:
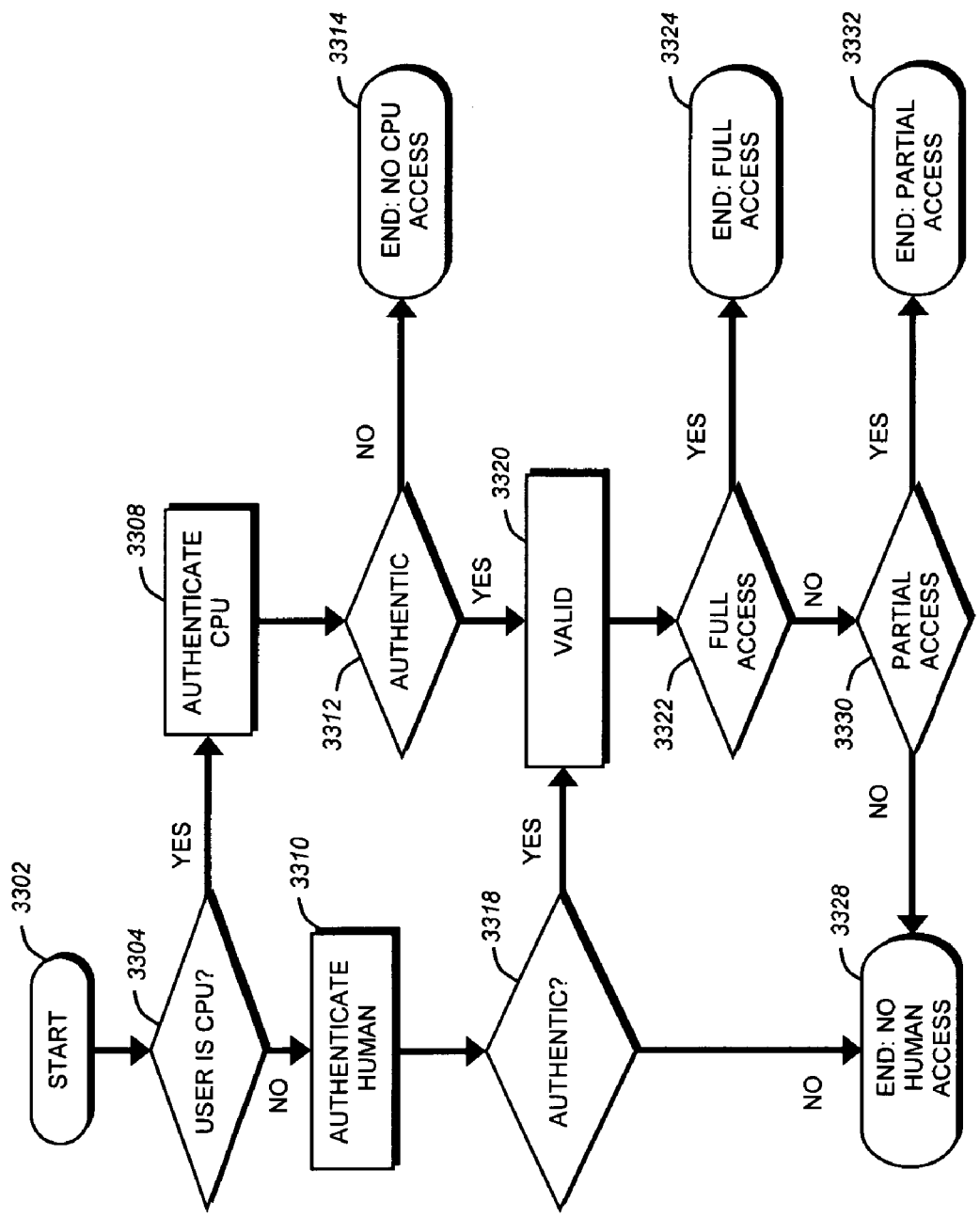
FIG. 33 shows a validation and authorization procedure.

Referring to FIG. 33, the validation and authorization procedure 3104 may begin with the logical block START 3302. Processing flow may continue to a test, as shown by logical block 3304 (labeled USER IS CPU?), which may determine if the user is an automatic computer (that is, not a human). If the result at 3304 is affirmative, processing flow may continue to logical block 3308 where the central processing facility 2904 may utilize a method to authenticate the user. This method may without limitation be a cryptographic authentication method, such as the Challenge-Handshake Authentication Protocol. The logical flow may then proceed to logical block 3312 (labeled AUTHENTIC?), which may represent a test of the result of the authentication method. Depending upon the result of this test, processing flow may continue either to the END: CPU NO ACCESS 3314 logical block or to the VALIDATE logical block 3320, as shown. The logical block 3314 may represent the procedure exiting with or without a status code and with no access granted to the automatic computer. If, on the other hand, the test at 3304 is negative, processing flow may continue to logical block 3310 where the central processing facility 2904 may gather authentication information, such as and without limitation a globally unique identifier (GUID) and password, from the user. The authentication information may then be selected from contents of one of the databases 2818 in logical block 3318 (labeled AUTHENTIC?). If the authentication information is associated with a table entry in one of the databases 2818, the user may be deemed authentic, the result of the test at 3312 may be affirmative, and processing flow may continue to logical block 3320, as shown. Otherwise, the result at 3318 may be negative and the procedure may conclude at logical block 3328, END: NO HUMAN ACCESS, which may represent the procedure exiting with or without a status code and with no access granted to the user. At logical block 3320, a GUID associated with the user, which may or may not be the username and which may be representative of a primary key in a table in one of the databases 2818, may be selected from the table. The selection may be tested at logical block 3322 (labeled FULL ACCESS?) to see if it indicates that the user should be granted full access to the system 2802. If the result of this test is affirmative, processing flow may continue to logical block 3324, END: FULL ACCESS, which may represent the procedure ending with full access granted to the user, perhaps generating a status code representative of both the authentication of the user and the validation of user's full access to the system 2802. Otherwise, the selection may be tested again, this time at logical block 3330 (labeled PARTIAL ACCESS?), as shown, to see if it indicates that the user should be granted partial access to the system 2802. If the result at logic block 3330 is affirmative, processing flow may continue to logical block 3332, END: PARTIAL ACCESS, which may represent the procedure ending with partial access granted to the user, perhaps generating a status code representative of both the authentication of the user and the validation of the user's partial access to the system 2802. Finally, as shown, if the result at logic block 3330 is negative, processing may continue to the aforementioned END: NO HUMAN ACCESS logical block 3328.

Figure 34:
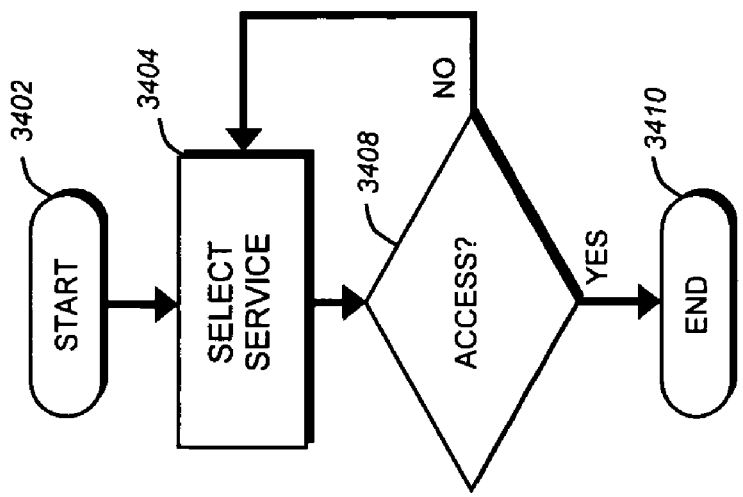
FIG. 34 shows a selection process by a validated/authorized user.

Referring to FIG. 34, the validated and authorized user may select a computing service to be provided by the system 2802. The procedure for this selection, which may represent the SELECT COMP. SERVICE procedure at the aforementioned logical block 3108, may begin at the top of the figure, where the user may enter the procedure at the START logical block 3402. Proceeding to the SELECT SERVICE logical block 3404, a service selection may be received by the system 2802 from the user. Then, as shown by logical block 3408, the selection may be compared to the access already granted to the user and the result of this comparison may be tested to see if it is a match. If the test result is negative, the procedure flow may return to logical block 3404. Otherwise, the service may have been successfully selected and the procedure may end, perhaps generating a code or indication representative of the selection, as shown by the END logical block 3410.

Figure 35:
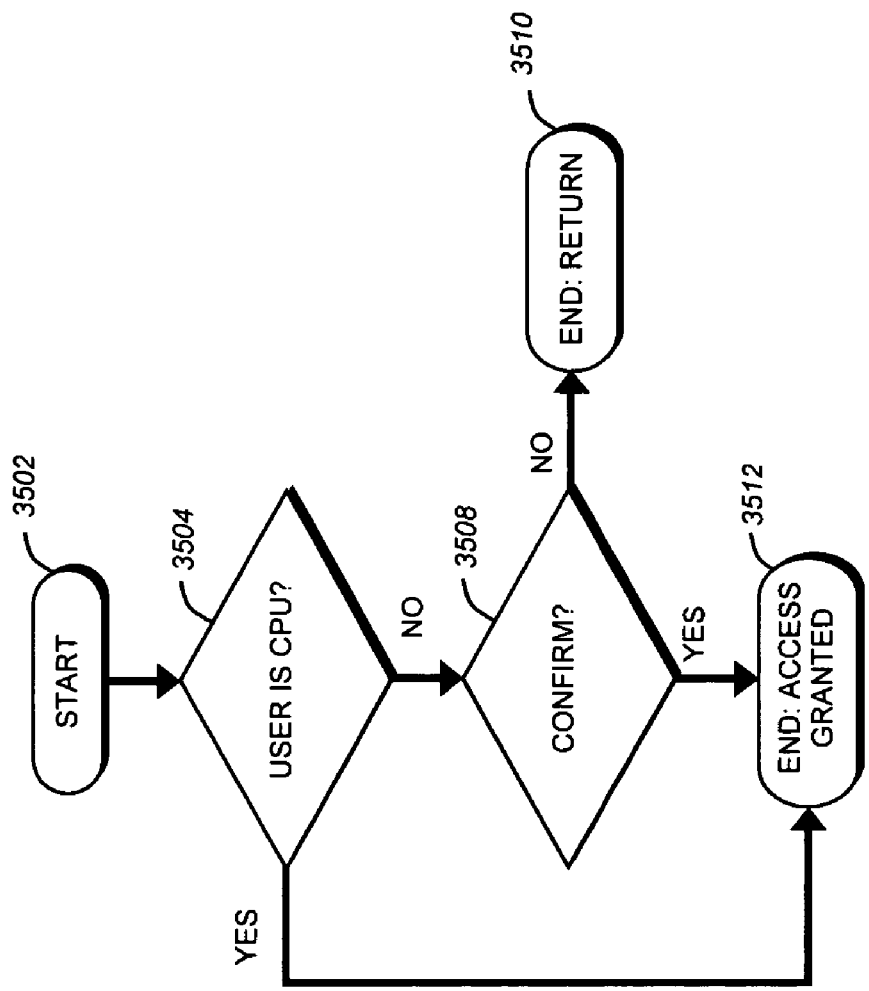
FIG. 35 shows a process for ending access to an electronic commerce service.

Referring to FIG. 35, a procedure for providing an end of electronic commerce access service, which may be represented by the aforementioned ACCESS: END SESSION logical block 3124, may begin with the START logical block 3502. Next, a test may be performed to determine if the user is a CPU, as shown by logical block 3504. An affirmative outcome in 3504 may direct the processing flow to the END: ACCESS GRANTED logical block 3512, which may represent the procedure ending with access to the service represented by the END logical block 3158 granted to the user, perhaps as signaled by a code or indication representative of the user's granted access. A negative outcome in 3504 may direct the procedure flow to END: RETURN 3510, from which procedure flow may return to the START logical block 3402 of FIG. 34.

Figure 36:
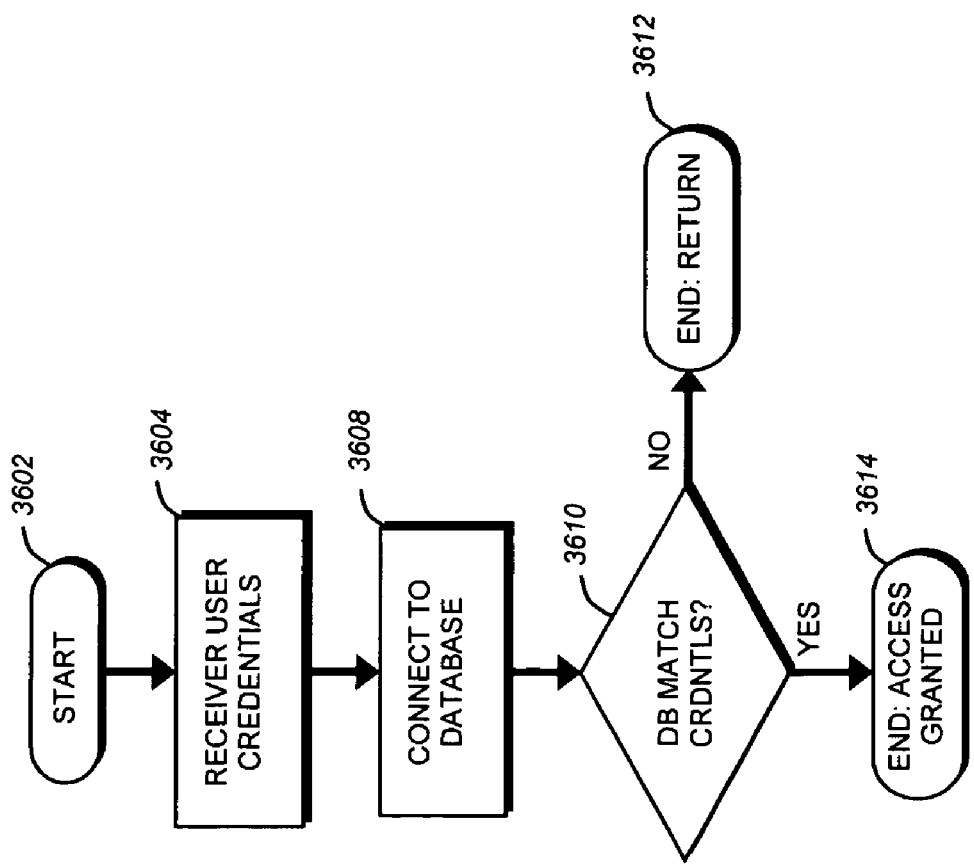
FIG. 36 shows user access to an electronic commerce service.

Referring to FIG. 36, the user may be granted or denied access to one of the computing services 2814. Proceeding from the START logical block 3602 at top of the figure, the system 2802 may receive the user's credentials, as shown by logical block 3604. The user's credentials may, without limitation, include a GUID, password, MAC address, public key, digital certificate, access token, biometric measurement, and so forth. Then, in logical block 3608, the system 2802 may connect to one of the databases 2818. Next, a test may compare the user's credentials to the contents of the database, as shown by logical block 3610. If there isn't a match, the user may be denied access to the computing service 2814 and processing flow may continue to logical block 3612, END: RETURN, from which the processing flow may return to logical block 3402 of FIG. 34. Otherwise, the user may be granted access to one of the computing services 2814 and processing flow may continue to logical block 3614, where this procedure ends, perhaps producing a success code or other success indication.

Figure 37:
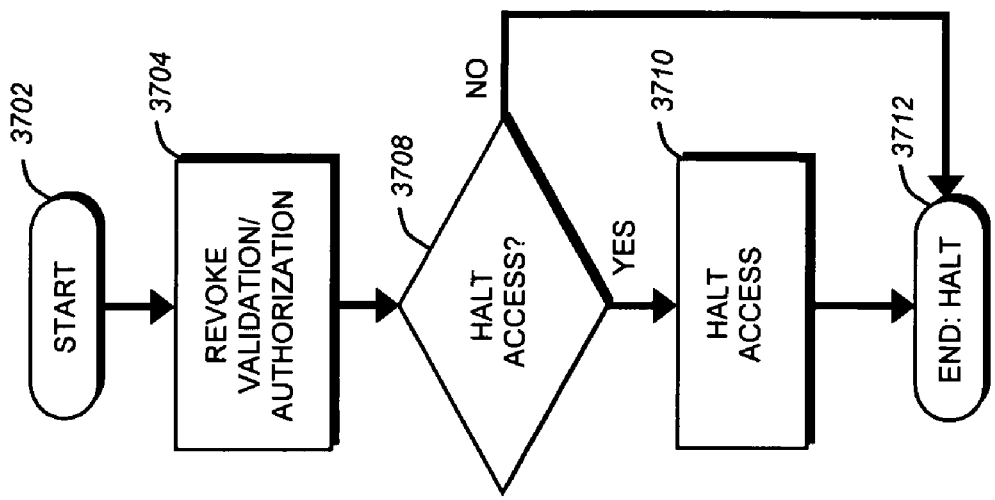
FIG. 37 shows a process for ending access to an electronic commerce service.

Referring to FIG. 37, an end of electronic commerce service, which may be represented by the END logical block 3158, may be provided according to the depicted procedure. Beginning with the START 3702 logical block, processing flow may continue to logical block 3704, REVOKE VALIDATION/AUTHORIZATION, where the validation and authorization of the user, as described hereinbefore with reference to FIG. 33, may be revoked. This revocation may, without limitation, include updating an entry in one of the databases 2818; adding a serial number associated with the validation and/or authorization to a certificate revocation list; and/or terminating the user's access to the system 2802 at the remote terminal, such as and without limitation by logging out the user. Processing flow may continue as shown to logical block 3708 (labeled HALT ACCESS?) where a test may be conducted to determine if the remote terminal should halt access to central processing facility 2904, such as and without limitation by disconnecting from the central processing facility 2904. If the result of this test is affirmative, processing flow may continue to logical block 3710, HALT ACCESS, where the access may be halted. Then, processing flow may continue to logical block 3712, END: HALT, where the entire electronic commerce procedure may either halt or restart from logical block START 3102, which is described hereinabove with reference to FIG. 31. If the test in logical block 3708 results in a negative result, processing flow may continue to logical block 3712, as described above.

The system 2802 may provide the user with a service that may facilitate the sale of a good and/or service. This service may be represented by the FACILITATION OF SALE OF GOOD/SERVICE logical block 3142 of FIG. 31 and may be described in detail hereinafter with reference to FIG. 38. Prior to accessing this service, the user may be required to gain access to this service by following the access procedure that may be represented by the ACCESS: SALE OF GOOD/SERVICE logical block 3110 of FIG. 31, which may be described hereinbefore with reference to FIG. 36.

Figure 38:
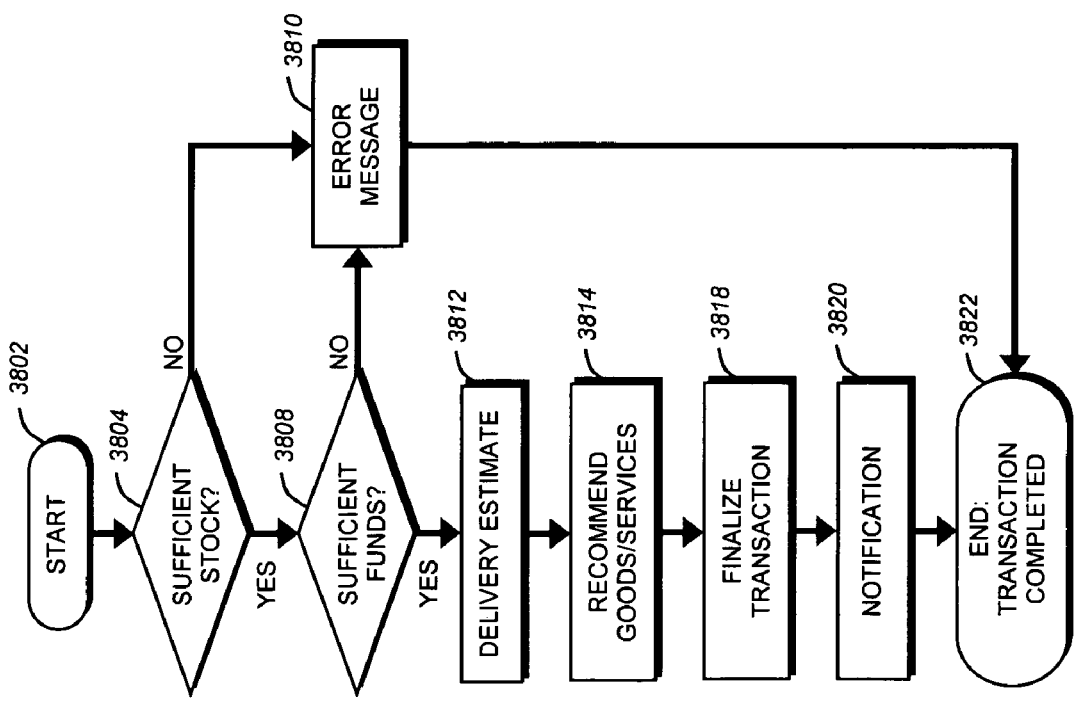
FIG. 38 shows a transaction process.

Referring to FIG. 38, a transaction service 3142 may be provided according to the depicted procedure. The good or service may be any of the goods and services described herein. Beginning with the START logical block 3802, processing flow may continue to a test, represented as logical block 3804 (labeled SUFFICIENT STOCK?), which may determine whether there exists sufficient stock of goods and/or resources for delivery of goods and/or performance of services to fulfill the proposed order. If the test result is negative, processing flow may proceed to the ERROR MESSAGE logical block 3810, which may result in the delivery of an error code or message, which may communicate the insufficient levels of stock and/or resources. This code or message may be delivered to an administrator, which may be one of the operators or may be an administrative automatic computer system. This administrator may manage inventory and resource levels and/or track sales that were not completed due to the lack of inventory and/or resources. When checking sufficient stock of goods and/or resources for performance of services the system may check sources other than in-house inventory and resources. It may be possible to purchase goods or commission resources from elsewhere and execute a profitable transaction. However, if the result of the test at logical block 3804 is affirmative, processing flow may proceed to the logical block 3808 (labeled SUFFICIENT FUNDS?).

Logical block 3808 may represent another test, which may determine if the potential purchaser, which may be the user, has sufficient funds to complete the transaction. The system may check the potential purchaser's credit card for authorization, may check the potential purchaser's bank balance, credit rating or balance with any online transaction brokering services, such as PayPal. If the test result is negative, processing flow may proceed to the ERROR MESSAGE logical block 3810, which may result in the display of an error message communicating the lack of funds or insufficient credit rating. The error message may also recommend or present ways in which the potential purchaser can remedy the error, such as by requesting a credit increase or reviewing his or her credit history for errors. The error message may also refer the potential purchaser to other retailers willing to sell to potential purchasers with lesser credit ratings. The first retailer may receive a fee or commission from the second retailer for this type of referral. The system may facilitate tracking and processing of these referrals. However, if the result of the test at logical block 3808 is affirmative, processing flow may proceed to the DELIVERY ESTIMATE logical block 3812.

Logical block 3812 may represent the process by which the system estimates delivery of the good or performance of the service. For a service the estimate may include a starting date and/or time and an ending date and/or time. The delivery estimate may involve the selection of a delivery method for a good or a priority level for a service. The different delivery methods and priority levels may be associated with different prices. The delivery estimate may also take into account pre-orders for items and services that have not yet been released to the public. The delivery estimate may include a transfer time for an electronic delivery. The delivery estimate may also include a return date or due date for an item that must be returned, such as a movie or game rental. The processing flow may then proceed to the RECOMMEND GOODS/SERVICES logical block 3814. This logical block 3814 may represent the process by which the system recommends related goods and/or services, such as accessories, updates, update subscriptions, warranties, complementary goods, or training services. The recommendation may be based on the good and/or service purchased in the current transaction and/or may be based on goods and/or services purchased by the potential purchaser in the past. The potential purchaser may select additional goods and/or services for purchase. Subsequently, the process of recommending related goods and/or services might repeat. The system may also allow the potential purchaser to place goods and/or services on a "wish list" for purchase in the future. The process flow may then continue to the FINALIZE TRANSACTION logical block 3818. The potential purchaser and the system may commit to the transaction at this stage, which may involve writing data to one of the databases 2818. The process flow may then proceed to the NOTIFICATIONS logical block 3820. This logical block 3820 may represent the notification of other related systems of the transaction. For example, the administrator or an inventory control system may be notified that the stock of a certain good has decreased. If the good requires special shipping, a notification may be sent to a shipping department allowing advance preparation for shipment of the good. A confirmation of the transaction may be transmitted to a purchaser, who may have been the potential purchaser. The processing flow may then continue to logical block 3822, END: TRANSACTION COMPLETED, where the procedure may end, perhaps producing a code or other indication of completion of the transaction.

The system 2802 may provide the user with a facilitation of advertising service. This service may be represented by the FACILITATION OF ADVERT. logical block 3160 of FIG. 31 and may be described in detail hereinafter with references to FIGS. 39, 40, 41, 42, 43, and 44. Prior to accessing this service, the user may be required to gain access to this service by following the access procedure that may be represented by the ACCESS: ADVERT. logical block 3128 of FIG. 31, which may be described hereinbefore with reference to FIG. 36.

Figure 39:
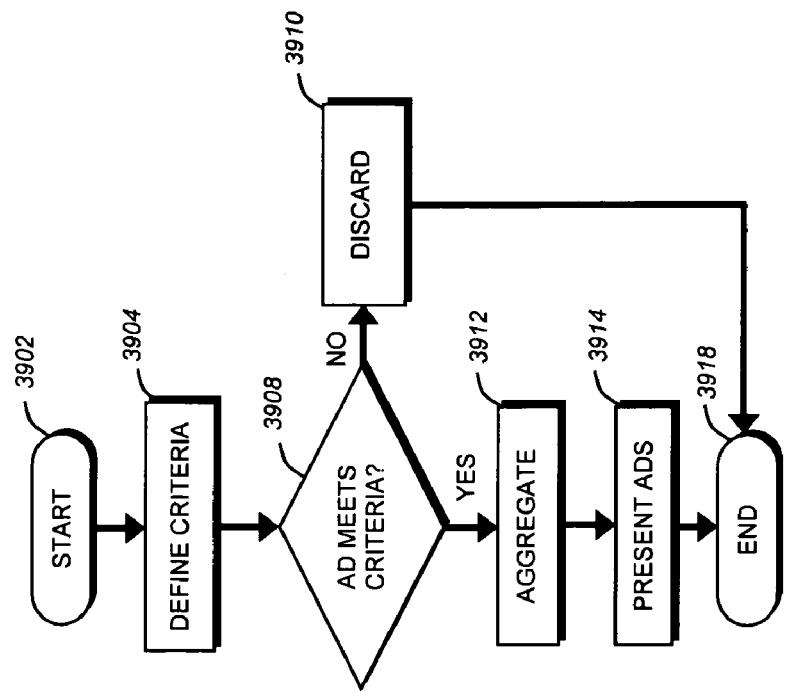
FIG. 39 shows an advertising process.

Referring to FIG. 39, the advertising service may include a procedure for aggregating advertisements. Beginning with the START logical block 3902, where an advertisement may be provided to the procedure, processing flow may proceed to the DEFINE CRITERIA logical block 3904. At this stage a criterion that may generally be associated with advertisements may be specified or defined. The criterion may pertain to content of the desired advertisements; delivery media of the desired advertisements; target demographics of the desired advertisements; cost of delivery of the desired advertisements; effectiveness of the desired advertisements; and so forth. In one embodiment, the system 2802 could include and/or the user may provide an advertising search engine, in which case a search string provided to the search engine may define the criterion. In another embodiment, the criterion may relate to a past behavior associated with and one or more of the users 2804, such as and without limitation purchasing behavior, Web surfing behavior, and so forth.

Once the criterion is defined, the processing flow may then continue to a test, represented as logical block 3908 (labeled AD MEETS CRITERIA?), which may determine whether or not the advertisement meets the specified criterion. This test may include a comparison of the criterion to information that may be stored in one of the databases 2818 and/or associated with the advertisement. This information may, without limitation, include a description of the content of the advertisement, an MPAA rating, an ESRB rating, a geographic location, a price, a display size, a display format, a rendering capability, an activation time or date, a deactivation time or date, and so forth. If the advertisement does not meet the criterion it may be discarded as depicted by logical block 3910. However, if the advertisement does meet the defined criteria the process flow may proceed to the AGGREGATE logical block 3912. The AGGREGATE logical block 3912 may represent the aggregation of the advertisement with other advertisements that may or may not meet the criterion. Moreover, the advertisements contained in the aggregate may be prioritized, filtered, and/or sorted at this stage. The process flow may then proceed to the PRESENT ADS logical block 3914. This may represent the presentation of the advertisements to the user, to a subset of the users 2804 (such as and without limitation the users 2804 associated with a particular demographic), to all of the users 2804, and/or to the general public. The advertisements may be displayed in a way consistent with the prioritization, filtering, and/or sorting of the advertisements. This display of advertisements may be embodied as a Web site, which may contain only advertisements and which may be created via a manual and/or automatic process. In any case, the processing flow may then continue to logical block 3918, END, where the procedure may end, perhaps producing a code or other indication of completion of the procedure.

Figure 40:
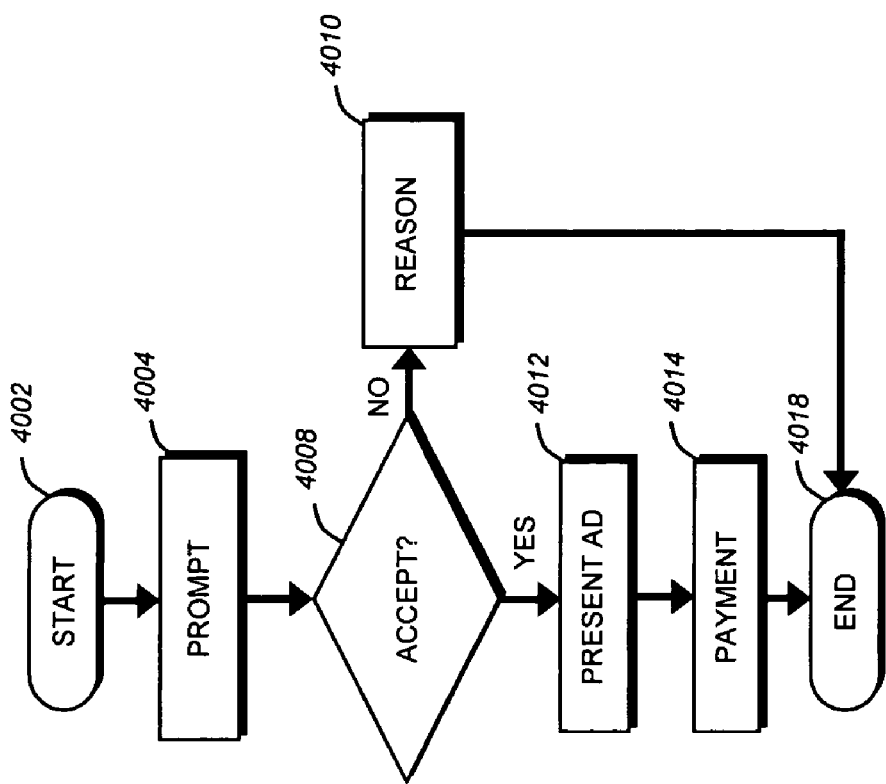
FIG. 40 shows an attention brokering process.

Referring to FIG. 40, the advertising service being may include attention brokering, which may be the business of buying and selling the attention of consumers. Beginning with the START logical block 4002, processing flow may proceed to the PROMPT logical block 4004. At this stage one of the consumers which may be the user, may be prompted to view an advertisement. Certain information about the advertisement may also be presented. The process flow may then proceed to a test, represented by logical block 4008 (labeled ACCEPT?), which may determine whether the consumer accepts presentation of the advertisement. If the result of this test is negative, the process flow may proceed to the REASON logical block 4010. At this step the consumer may provide a reason for declining presentation of the advertisement. The consumer may select from among several answer choices or enter his or her own choice. These reasons may then be presented to an administrator or the advertisers and used to alter the process or advertisement content so that the consumer is more likely to accept presentation of a future advertisement. However, if the result of the test at 4008 is affirmative, the processing flow may proceed to logical block 4012, which may represent the presentation of the advertisement to the consumer. The process flow may then proceed to the PAYMENT logical block 4014. This logical block 4014 may represent one or more payments to the consumer viewing the advertisement. There may also be one or more payments to other parties involved in the attention brokering process, such as an advertising agency, system administrator, or Web site operator. Whether proceeding from 4010 or 4014, the processing flow may continue to logical block 4018, END, where the procedure may end, perhaps producing a code, payment record, and/or other indication of completion of the procedure.

Figure 41:
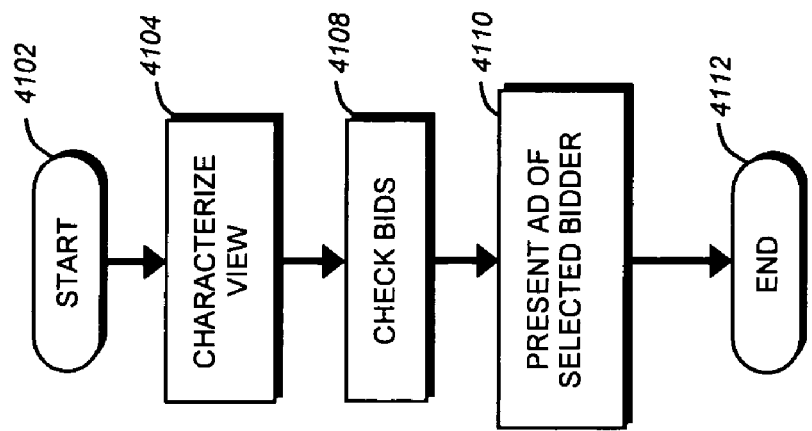
FIG. 41 shows an advertisement bidding process.

Referring to FIG. 41, the advertising service may include bidding to advertise, which may involve consumers being presented with advertisements from the highest bidding advertiser. Beginning with the START logical block 4102, processing flow may proceed to the CHARACTERIZE VIEW logical block 4104. The system 2802 may characterize the type of consumer or consumers who will view the advertisement. The process flow may then proceed to the CHECK BIDS logical block 4108 where bids associated with advertisements and placed by advertisers may be compared to determine a winning bid. The bids may be based upon target demographics; marketing objectives such as reach, recall, and number of impressions; pricing; and so forth. Once a winning bid is determined, the process flow may then proceed to the PRESENT AD OF SELECTED BIDDER 4110 logical block. Here, the system may present the advertisement associated with the winning bid to the user and/or one or more consumers, which may also be users 2804. In this way the system may fill orders for presentation of advertisements in connection with bids. The processing flow may then continue to logical block 4112, END, where the procedure may end, perhaps producing a code, presentation record to be used for billing purposes or other indication of completion of the procedure.

Figure 42:
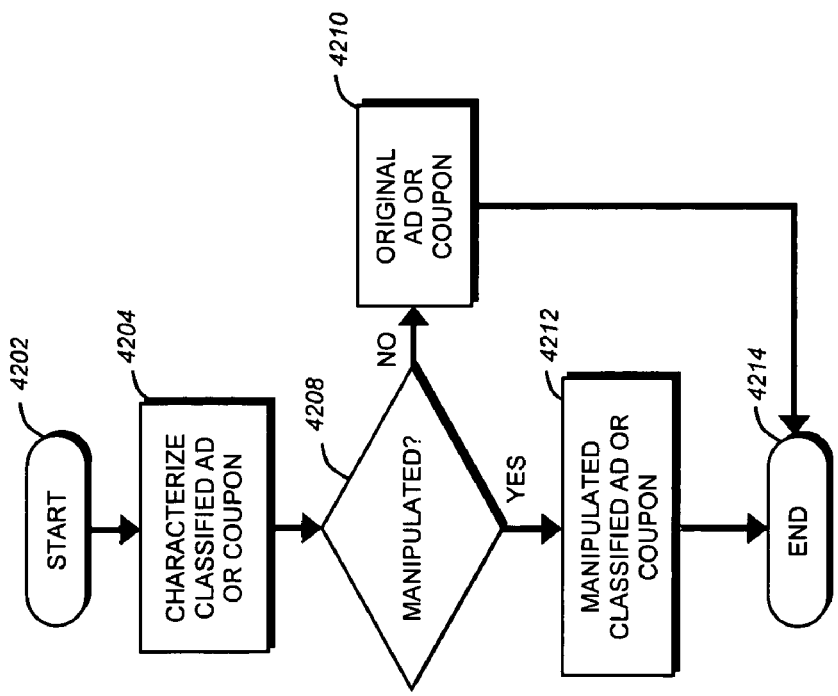
FIG. 42 shows a coupon process.

Referring to FIG. 42, the advertising service may include the manipulation of a classified advertisement or coupon. Beginning with the START logical block 4202, processing flow may proceed to the CHARACTERIZE CLASSIFIED AD OR COUPON logical block 4204. The logical block 4204 may represent an action of characterizing the classified advertisement or coupon. Relevant characteristics may include source, expiration, price and type of good and/or service, and so forth. The process flow may then continue to a test, represented as logical block 4208 (labeled MANIPULATE?), which may determine whether the classified advertisement or coupon should be manipulated. If the test result is negative, the process flow may proceed to the logical block ORIGINAL AD OR COUPON 4210 and the classified advertisement or coupon may not be manipulated. If the test result is affirmative, however, then the system may manipulate the classified advertisement or coupon, as may be represented by the MANIPULATED CLASSIFIED AD OR COUPON logical block 4212. In the case that a coupon may be manipulated, the manipulation may involve the issuing, processing, modifying, aggregating, redeeming, revoking, validating, distributing, or otherwise affecting or handling of the coupon. In the case that a classified advertisement may be manipulated, the manipulation may involve the printing, processing, modifying, aggregating, canceling, validating, distributing, or otherwise affecting or handling of the classified advertisement. The processing flow may then continue to logical block 4214, END, where the procedure may end, perhaps producing a code, record or other indication of completion of the procedure.

Figure 43:
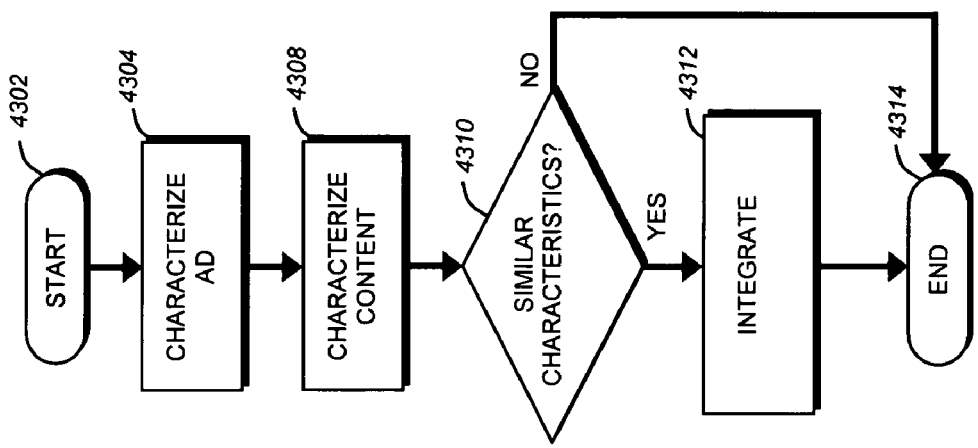
FIG. 43 shows a dynamic ad placement process.

Referring to FIG. 43, the advertising service may include the dynamic insertion of an advertisement into other content. Beginning with the START logical block 4302, processing flow may proceed to the CHARACTERIZE AD logical block 4304, which may represent an action of characterizing the advertisement. Characteristics of the advertisement may include the type of good and/or service offered for sale, the pricing structure, a target geographic region, a target demographic, and so forth. The process flow may then proceed to the CHARACTERIZE CONTENT logical block 4308, which may involve the characterization of the other content. The other content may be electronic content, perhaps including audio, video, text, and so forth. Characteristics of the content may include target age, running time, target geographic region, target demographic, and so forth. The process flow may then continue to a test, which may be represented as logical block 4310 (labeled SIMILAR CHARACTERISTICS?). The test may determine the degree of similarity or compatibility between the advertisement and the other content. If the degree of similarity or compatibility is below a certain threshold the test result may be negative. If the degree of similarity or compatibility is above or equal to a certain threshold the test result may be affirmative. For example, the electronic content and advertisement may be targeted to consumers of a similar age in a similar geographic region. In another example, the editor or publisher of the advertisement and the content may be the same, leading to an affirmative test result. Given the affirmative test result, the process flow may proceed to the INTEGRATE logical block 4312. This logical block 4312 may represent the integration of the advertisement into the other content. The system may optimize the location and manner of integration of the advertisement based on the characterization of the advertisement, the characterization of the other content, or based on other factors. Whether due to a negative result at 4310 or due to normal processing flow from 4312, the processing flow may continue to logical block 4314, END, where the procedure may end, perhaps producing a code, record or other indication of completion of the procedure.

Figure 44:
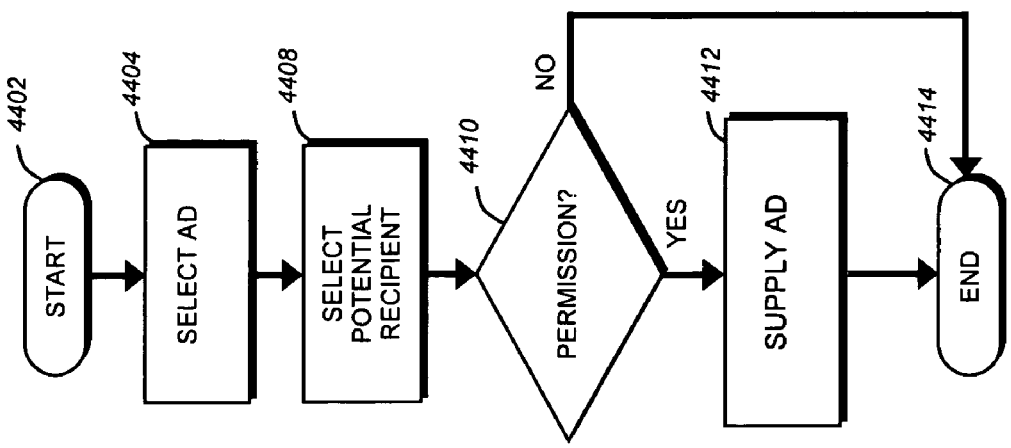
FIG. 44 shows a permission-based advertising process.

Referring to FIG. 44, the advertising service may include permission-based advertising. Beginning with the START logical block 4402, processing flow may proceed to the SELECT AD logical block 4404, which may represent a selection of an advertisement to be transmitted or presented to a recipient, which may be the user or some other consumer. The process flow may then proceed to the SELECT POTENTIAL RECIPIENT 4408 logical block, which may involve selection of the recipient. The process flow may then continue to a test, which may be represented as logical block 4410 (labeled PERMISSION?). This test may determine whether an advertiser associated with the advertisement has permission to transmit the advertisement to the recipient. The permission may depend upon the advertisement's type and/or a transmission method's type, where the transmission method may be used to transmit the advertisement. For example, the advertiser may have permission to transmit the advertisement to the recipient only when the advertisement relates to electronics and the advertisement is transmitted via e-mail. It follows that, if the result of the test at 4410 is negative, the advertisement may not be sent and processing flow may proceed to the END logical block 4414. However, if the test result is affirmative, the process flow may proceed to the SUPPLY AD logical block 4412, which may represent transmitting the advertisement to the recipient. The advertisement may be transmitted over the Internet, via email, via fax, via instant messenger, via VoIP, via telephone, as video, as audio, as text, or by any other delivery or presentation method. The processing flow may then continue to logical block 4414, END, where the procedure may ends, perhaps producing a code, record, or other indication of completion of the procedure.

The system 2802 may facilitate many other advertising services. Prior to accessing these other advertising services 3160, the user may be required to gain access to the services by following the ACCESS: ADVERT. procedure 3128, which may be described hereinbefore with reference to FIG. 36. The advertising service may be direct communication between an advertiser and one of the users or direct communication between one or more users. The advertising service may also be a promotion. Any of the abovementioned advertising procedures may apply to the promotion. The advertising service may also be a commercial e-mail service. Any of the above-mentioned advertising procedures may apply to the commercial e-mail service.

The system 2802 may provide the user with a facilitation of recommendation service. This service may be represented by the FACILITATION OF RECOMMEND. logical block 3144 of FIG. 31 and may be described in detail hereinafter with reference to FIG. 45. Prior to accessing this service, the user may be required to gain access to the service by following the access procedure that may be represented by the ACCESS: RECOMMEND. logical block 3112 of FIG. 31, which may be described hereinbefore with reference to FIG. 36.

Figure 45:
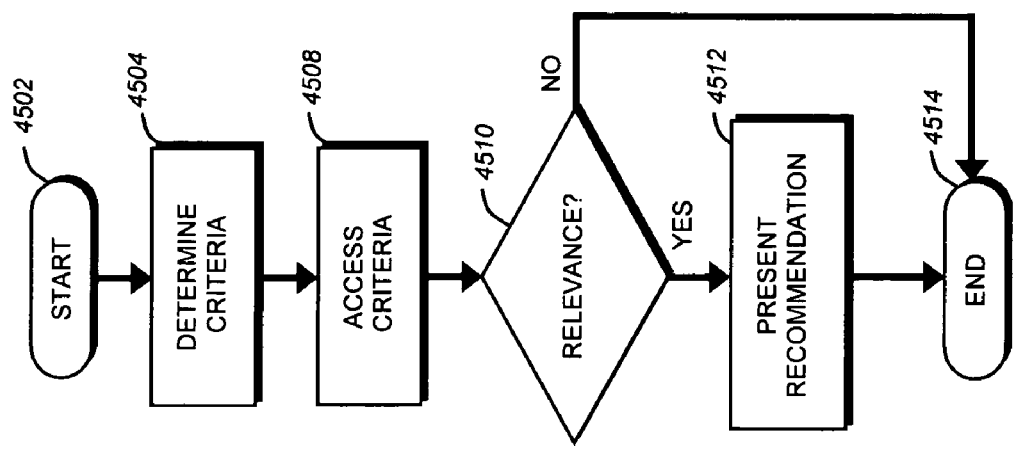
FIG. 45 shows a recommendation process.

Referring to FIG. 45, the facilitation of recommendation service may be provided according to the depicted procedure. The service may involve the provision, generation and/or delivery of a recommendation based on or associated with one or more of a buying-based behavior, a click-based behavior, collaborative filtering, customer reviews, editorial reviews, machine learning, reputation measures, and so forth. Beginning with the START logical block 4502, the process flow may proceed to the DETERMINE CRITERIA logical block 4504, which may represent determining a criterion relevant to the provision, generation and/or delivery of the recommendation. The criterion may relate to the recommendation and/or to a potential recipient of the recommendation. The process flow may then proceed to the ASSESS CRITERIA logical block 4508, which may represent an assessment of the criterion determined in the DETERMINE CRITERIA logical block 4504. As an example, the relevant criterion may be a buying-based behavior, a click-based behavior, a customer review, a reputation rating, and so forth. The assessment of a buying-based behavior criterion may be that the potential recipient of the recommendation has purchased three items of a certain type in the last four months. The assessment of a customer review may be expressed as a number of stars on a five-star scale that an item may have received in a customer review. The processing flow may continue to a test, represented as logical block 4510 (labeled RELEVANCE?), which may determine whether the recommendation is relevant to the potential recipient of the recommendation. If the test result is affirmative, processing flow may continue to the PRESENT RECOMMENDATION logical block 4512, where the recommendation may be generated, provided, and/or delivered to the potential recipient. For example, the recommendation may be a favorable recommendation related to an accessory for a product purchased by the recipient of the recommendation in the last three months. Then, the processing flow may continue to the END logical block 4514. However, if the test result is negative, the recommendation may not be presented and processing flow may continue to logical block 4514, END, where the procedure may end, perhaps producing a code, record or other indication of completion of the procedure.

The system 2802 may provide the user with a facilitation of metadata service. This service may be represented by the FACILITATION OF METADATA logical block 3162, which may be described in detail hereinafter with reference to FIG. 46. Prior to accessing this service, the user may be required to gain access to this service by following the access procedure that may be represented by the ACCESS: METADATA logical block 3130, which may be described hereinbefore with reference to FIG. 36.

Figure 46:
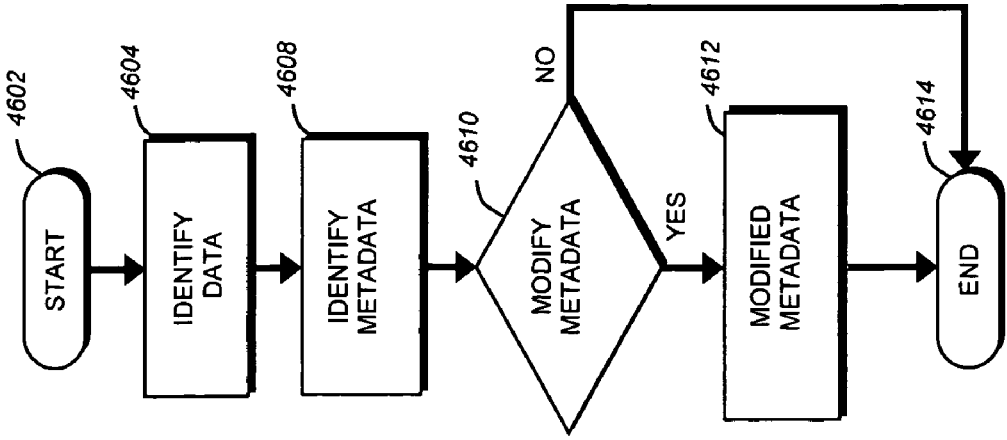
FIG. 46 shows a metadata manipulation process.

Referring to FIG. 46, the FACILITATION OF METADATA service 3162 may be provided according to the depicted procedure. The service may involve the dynamic modification of user state, navigation, and/or navigation based upon behavior. Beginning with the START logical block 4602, the process flow may proceed to the IDENTIFY DATA logical block 4604, which may represent the identification a certain datum of interest. The datum may relate to a user, an item, a company, or other data. The process flow may then proceed to the IDENTIFY METADATA logical block 4608, which may represent identifying the metadata of interest associated with the data. For example, the metadata associated with a user may include the passwords, ratings, favorite Web site, account information, shipping and billing addresses of the user, and so forth.

The processing flow may continue to a test, which may be represented as logical block 4610 (labeled MODIFY METADATA?), which may determine whether the metadata associated with the data should be modified. If the test result is affirmative, the metadata may be modified. For example, a user may have a new shipping address. The shipping address may be stored as metadata and may be updated as new information. The processing flow may then proceed to the MODIFIED METADATA logical block 4612, which may represent the modified metadata. If the test result is negative the metadata mat not be modified. This may be the case if the user does not have the security or access level required for modification of the relevant metadata. The processing flow may then continue to logical block 4614, END, where the procedure may end, perhaps producing a code, record, and/or other indication of completion of the procedure.

The system 2802 may provide the user with a facilitation of price service. This service may be represented by the FACILITATION OF PRICE logical block 3148, which may be described in detail hereinafter with reference to FIG. 47. Prior to accessing this service, the user may be required to gain access to this service by following the access procedure that may be represented by the ACCESS: PRICE logical block 3114, which may be described hereinbefore with reference to FIG. 36.

Figure 47:
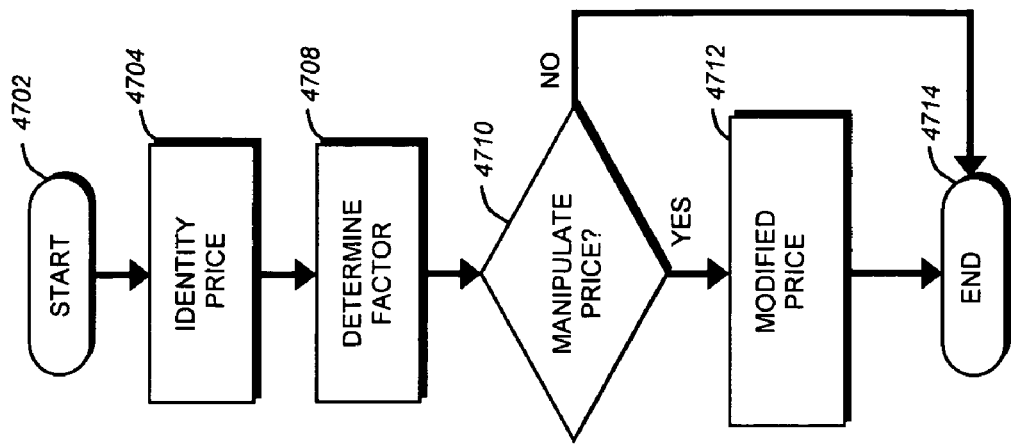
FIG. 47 shows a pricing process.

Referring to FIG. 47, the facilitation of price service may be provided according to the depicted procedure. Beginning with the START logical block 4702, the process flow may proceed to the IDENTIFY PRICE logical block 4704, which may represent identifying a certain price of interest. The price may relate to a good and/or service of interest. The processing flow may then proceed to the DETERMINE FACTOR logical block 4708, which may represent determining a factor. The factor may be an agent or bot, an auction, a catalog aggregator, a pricing comparison engine, a rating, and/or a reverse auction. The processing flow may continue to a test, which may be represented as logical block 4710 (labeled MODIFY PRICE?), which may determine whether the price should be modified based on the factor. The manipulation may include generating, retrieving, storing, deducing, guessing, anticipating, and/or modifying the price. If the test result is affirmative, processing flow may continue first to the MODIFIED PRICE logical block 4712, where the price may be modified, and then to the END logical block 4714, as shown. However, if the test result is negative, processing flow may continue to the END logical block 4714, where the procedure may end, perhaps producing a code, a record, and/or other indication of completion of the procedure. For example, the price may be the price of a certain computer monitor offered for sale by the user and the factor may be a price comparison engine. The comparison engine may locate the prices at which competitors of the user are offering the same monitor. An aspect of the system 2802, such as the central processing facility 2904 and/or an automatic computer that may be one of the users 2804, may be programmed to maintain the lowest price on the market for the monitor. If any of the competitors' prices are lower than the user's price, the test result may be affirmative and, therefore, the processing flow may proceed to the MODIFIED PRICE logical block 4712, which may represent this aspect of the system reducing the price.

The system 2802 may provide the user with a FACILITATION OF COMMUNICATION OF INFORMATION service 3172, which is described hereinafter with reference to FIG. 48. Prior to accessing this service 3172, the user may be required to gain access to the service by following the ACCESS: COMMUNICATION OF INFORMATION procedure 3140, which may be described hereinbefore with reference to FIG. 36.

Figure 48:
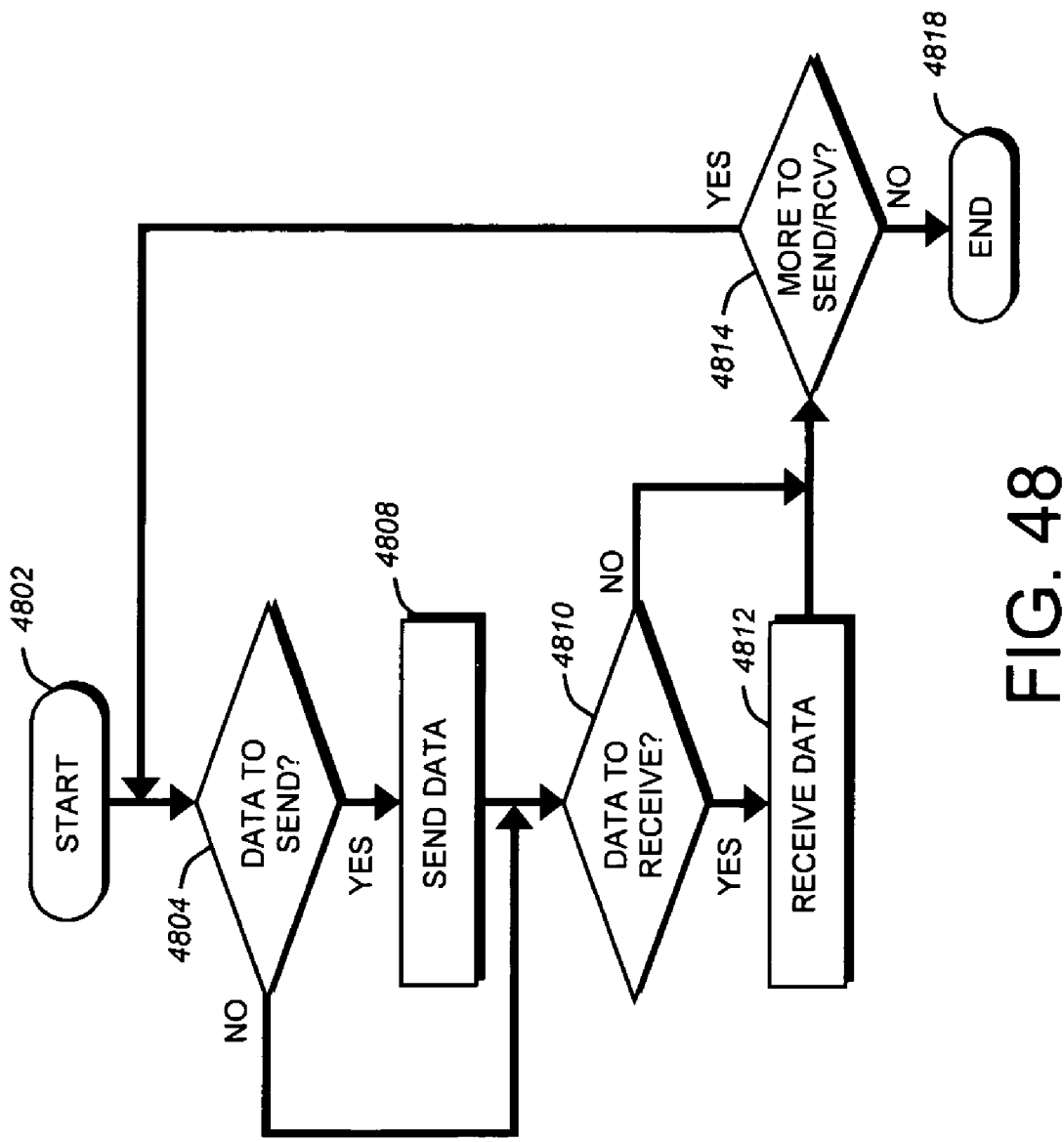
FIG. 48 shows an information process.

Referring to FIG. 48, the FACILITATION OF COMMUNICATION OF INFORMATION service may be provided according to the depicted procedure. Beginning with the START logical block 4802, processing flow may continue to a test, represented as logical block 4804 (labeled DATA TO SEND?), which may determine whether there exists data ("the existing data") to send from the remote terminal 2810 to the central processing facility 2904. If the test result is affirmative, processing flow may proceed to the SEND DATA logical block 4808, where the existing data may be transmitted from the remote terminal 2810 to the central processing facility 2904. Next, processing flow may continue to another test, which may be represented as logical block 4810 (labeled DATA TO RECEIVE?), which may determine whether there exists data to receive from the central processing facility 2904 at the remote terminal 2810. Similarly, if the test result at 4804 is negative, processing flow may proceed to 4810. In any case, if the test result at 4810 is affirmative, processing flow may continue to the RECEIVE DATA logical block 4812. Otherwise, processing flow may continue to a test at logical block 4814 (labeled MORE TO SEND/RECEIVE?). The RECEIVE DATA logical block 4812 may represent the transmission of data from the central processing facility 2904 and the subsequent reception of the data at the remote terminal 2810. The test at logical block 4814 may determine whether there is more data to be sent and/or received by the central processing facility 2904 and/or the remote terminal 2810. If the result of this test is affirmative, processing flow may proceed as shown, reentering the logical block 4804. Otherwise, the processing flow may continue to logical block 4818, END, where the procedure may end, perhaps producing a code or other indication associated with the transmission and/or reception of data.

The system 2802 may provide the user with a facilitation of user interface service. This service may be represented as the FACILITATION OF USER INTERFACE logical block 3154 of FIG. 31, which may be described in detail hereinafter with reference to FIG. 49. Prior to accessing this service, the user may be required to gain access to the service by following the access procedure that may be represented by the ACCESS: USER INTERFACE logical block 3122 of FIG. 31, which may be described hereinbefore with reference to FIG. 36.

Figure 49:
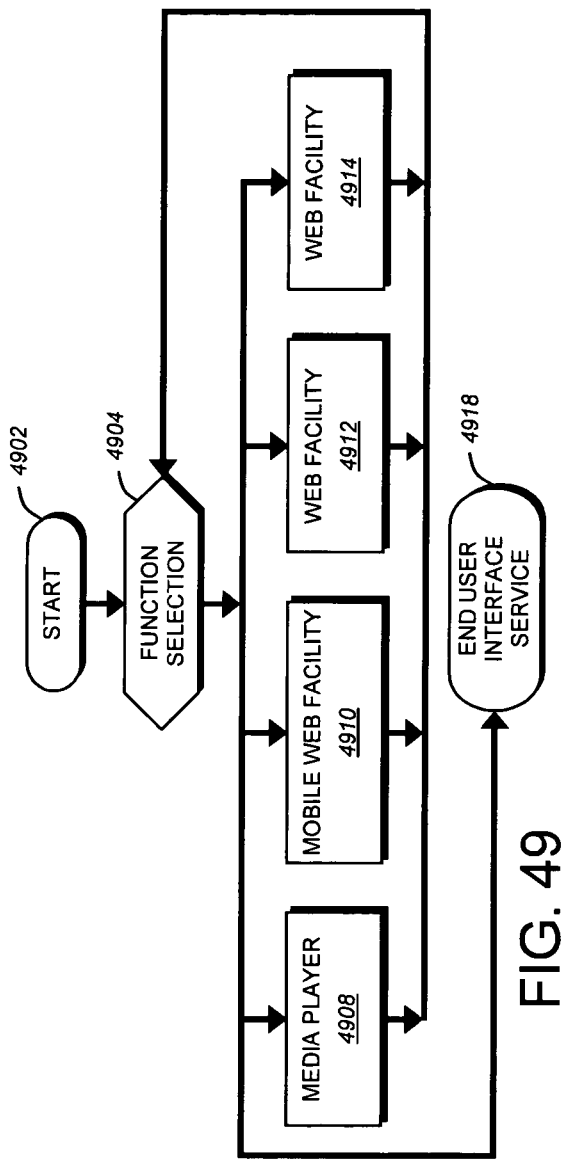
FIG. 49 depicts a user interface service.

Referring to FIG. 49, the FACILITATION OF USER INTERFACE service 3154 may be provided according to the depicted procedure. Starting at the top of the figure at the START logical block 4902, processing flow may proceed to a FUNCTION SELECTION logical block 4904, where an appropriate user interface function may be selected. This function selection may be determined based upon a preference, which may be specified by the user, may be implied by a type of the remote terminal 2810 (such as and without limitation: media player, mobile Web facility, Web facility, or secure device), and/or may be stored in one of the databases 2818. In any case, once a user interface function is selected, processing flow may proceed to the selected function, which may be represented as one of the logical blocks 4908, 4910,

4912, 4914, and 4918. Generally, these functions may provide a user interface, which may be displayed on the remote terminal and with which the user may interact with other computing services 2814. In particular, a MEDIA PLAYER 4908 may represent a function that enables an audio, video, or other rich media interface. This enablement may without limitation include the provision of data in one or more of the following formats: Macromedia Flash, Windows WMV, Apple QuickTime, MPEG-3, MPEG-4, WAV, Java JAR file, Windows native executable, Macintosh native executable, and so forth. The MOBILE WEB FACILITY 4910 may represent a function that enables a mobile Web interface, such as may be embodied by a cell phone, a PDA, and so forth. This enablement may without limitation include the provision of data in one or more of the following formats: SMS, XML, HTML, XHTML, and so forth. The WEB FACILITY 4912 may represent a function that enables a Web interface, such as may be embodied by a Web browser. This enablement may without limitation include the provision of data in one or more of the following formats: XML, XHTML, HTML, and so forth. The SECURE DEVICE 4914 may represent a function that enables an interface on a secure device, such as may be embodied by a remote terminal 2810 connected to the central processing facility 2904 via a secure protocol such as SSH, SSL, IPSec, and so forth. This enablement may without limitation include the provision of data encrypted according to one or more of the following algorithms: 3-Way, Blowfish, CAST, CMEA, DES, Triple-DES, DEAL, FEAL, GOST, IDEA, LOKI, Lucifer, MacGuffin, MARS, MISTY, MMB, NewDES, RC2, RC4, RC5, RC6, REDOC, Rijndael, Safer, Serpent, SQUARE, Skipjack, TEA, Twofish, ORYX, SEAL. As shown, unless the END USER INTERFACE SERVICE function (represented by logical block 4918) is selected, processing flow may return to the FUNCTION SELECTION logical block 4904. Logical block 4918 may represent the end of this procedure and, perhaps, may represent the production of a success code, an exit code, or some other indication of process termination.

The system may provide the user with a facilitation of a portal service. This service may be represented by the FACILITATION OF A PORTAL logical block 3170 of FIG. 31 and may be described in detail hereinafter with reference to FIG. 50. Prior to accessing this service, the user may be required to gain access to the service by following the access procedure that may be represented by the ACCESS: PORTAL logical block 3138 of FIG. 31, which may be described hereinbefore with reference FIG. 36.

Figure 50:
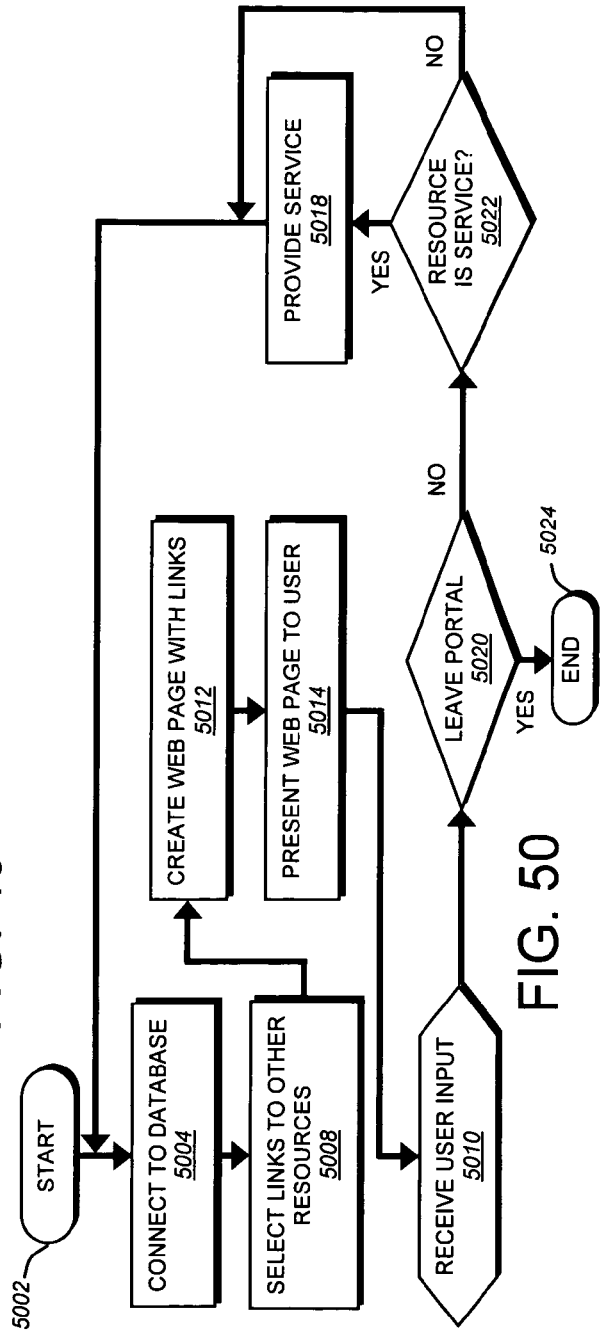
FIG. 50 depicts a portal service.

Referring to FIG. 50, the FACILITATION OF A PORTAL service 3170 may be provided according to the depicted procedure. The procedure may begin at the START logical block 5002 and may proceed to the CONNECT TO DATABASE logical block 5004, which may represent the central processing facility 2904 connecting to one of the databases 2818 (which may be referred to in this paragraph as "the database"). Processing flow may continue to logical block 5008 where links to other resources, which may without limitation be embodied as URLs or URIs, may be selected from the database. The other resources may relate to subject matter associated with an object of electronic commerce. For example and without limitation, the object of electronic commerce may be common stock and the related subject matter may without limitation include news with potential impact on the value of the common stock, real-time quotes, historical data, stock market averages, and so forth. The other resources may also be the services 2814. After selecting the links, a Web page comprising the links may be created at logical block 5012. This Web page may then be presented to the user, as may be shown by the PRESENT WEB PAGE TO USER logical block 5014. The user may select a link within the Web page, which may be received by the system 2802 as user input, as may be shown by the RECEIVE USER INPUT logical block 5010. Processing flow may then continue to a test in logical block 5020, which may determine whether the user input is indicative of the user's desire to leave the portal. If so, processing flow may proceed to the END logical block 5024, where the procedure may end. Otherwise, processing flow may continue to logical block 5022 (labeled RESOURCE IS SERVICE?), where a test may determine whether the user input is indicative of the user requesting a service 2814. If this test results in an affirmative result, processing flow may proceed to logical block 5018 where the service 2814 may be provided, such as by spawning a process and/or thread as described hereinbefore with reference to FIG. 51. Finally, processing flow may proceed as shown back to 5004. It should be appreciated that, in embodiments, the connection to the database 2818 that may be established during the first pass of the processing flow through 5004 may be a persistent connection and that subsequent passes through 5004 may simply check to see if the persistent connection is still valid. If it is, processing flow may proceed immediately to 5008. If it isn't, the connection may be reestablished.

The system 2802 may provide the user with a facilitation of privacy policy service. This service may be represented by the FACILITATION OF PRIVACY POLICY logical block 3152 of FIG. 31 and may be described in detail hereinafter with reference to FIG. 52. Prior to accessing this service, the user may be required to gain access to this service by following the access procedure that may be represented by the ACCESS: PRIVACY POLICY, logical block 3120 of FIG. 31, which may be described hereinbefore with reference to FIG. 36.

Figure 52:
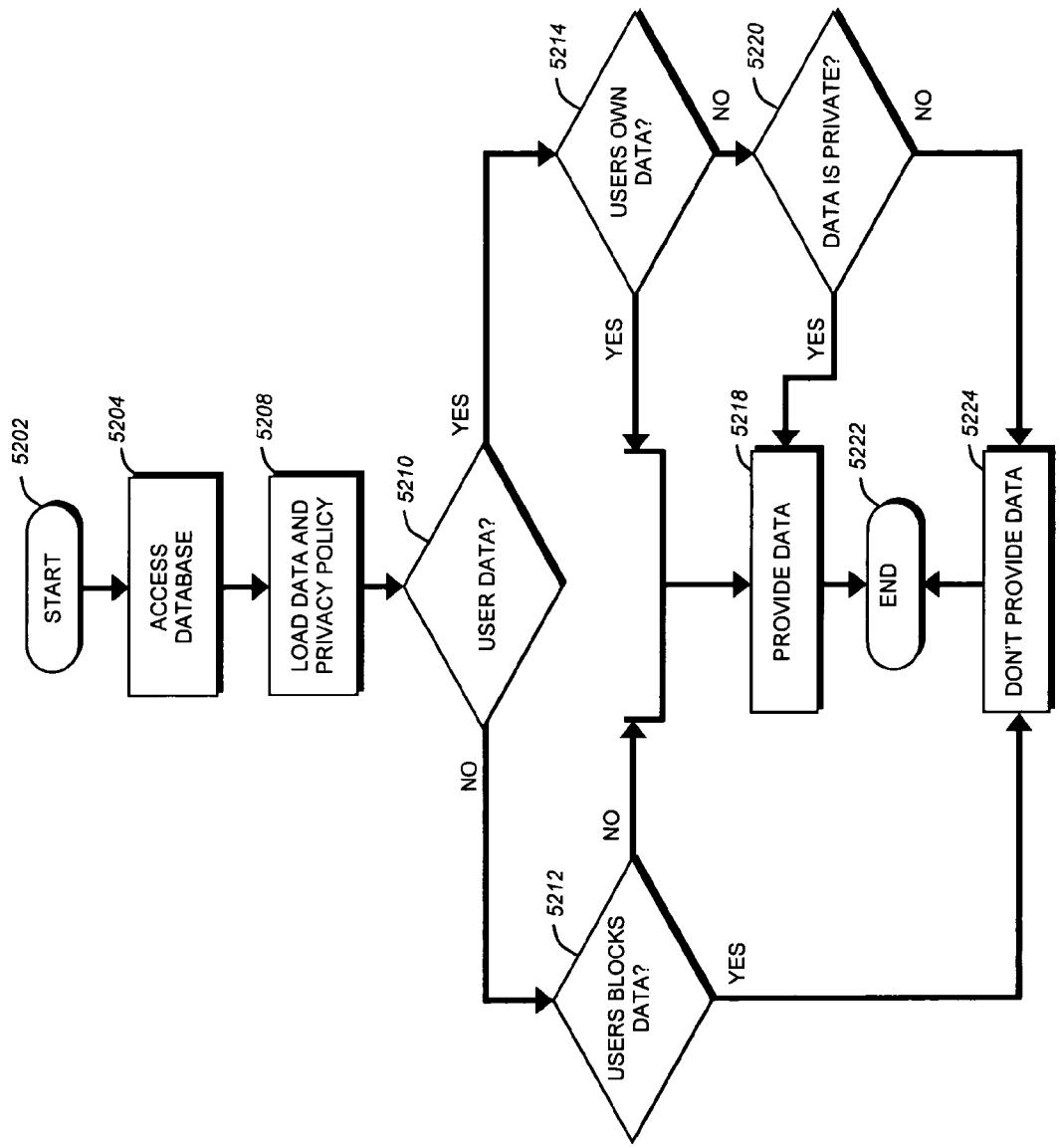
FIG. 52 shows a process for implementing a privacy service.

Referring to FIG. 52, the facilitation of privacy policy service may be provided according to the depicted procedure. The procedure may begin at the START logical block 5202 and proceed to the ACCESS DATABASE logical block 5204, which may represent the central processing facility 2904 accessing one of the databases 2818 (which may be referred to in this paragraph as "the database"). Processing flow may continue to LOAD DATA AND PRIVACY POLICY logical block 5208 where data and a privacy policy may be selected from the database. Next, a test to determine whether the data is associated with one of the users 2804 is conducted, as may be shown by the logical block 5210 (labeled USER DATA?). If the result of the test is affirmative, processing flow may continue to logical block 5214 (labeled USER'S OWN DATA?), where a test may be conducted to determine if the data belongs to the user. If the result of the test at 5214 is affirmative, processing flow may continue, as shown, to the PROVIDE DATA logical block 5218, where the data may be provided to the user. From there, processing flow may continue to the END logical block 5222, where this procedure may end, perhaps producing a code, record, or other indication of completion of the procedure. However, if the result of the test at 5214 is negative, then processing flow may continue to a test that may determine if the privacy policy indicates that the data is private, as shown by logical block 5220 (labeled DATA IS PRIVATE?). If the result of this test is negative, then processing flow may continue to logical block 5218, as shown. Otherwise, processing flow may continue to the DON'T PROVIDE DATA logical block 5224, where the data may not be provided to the user and from which processing flow may then proceed to the END logical block 5222. However, if the result of the test at 5210 is negative, then processing flow may proceed to logical block 5212 (labeled USER BLOCKS DATA?), where a test may be conducted to determine if the privacy policy contains an indication that one of the users 2804 desires to block the data. If this test results in an affirmative result, then processing flow may proceed as shown to logical block 5224. Otherwise, processing flow may proceed, also as shown, to logical block 5218.

The system 2802 may facilitate a facilitation of schema service. This service may be represented by the FACILITATION OF SCHEMA logical block 3168 of FIG. 31, which may be described in detail hereinafter with reference to FIG. 53. Prior to accessing this service, the user may be required to, gain access to this service by following the access procedure that may be represented by the ACCESS: SCHEMA logical block 3134, which may be described hereinbefore with reference to FIG. 36.

Figure 53:
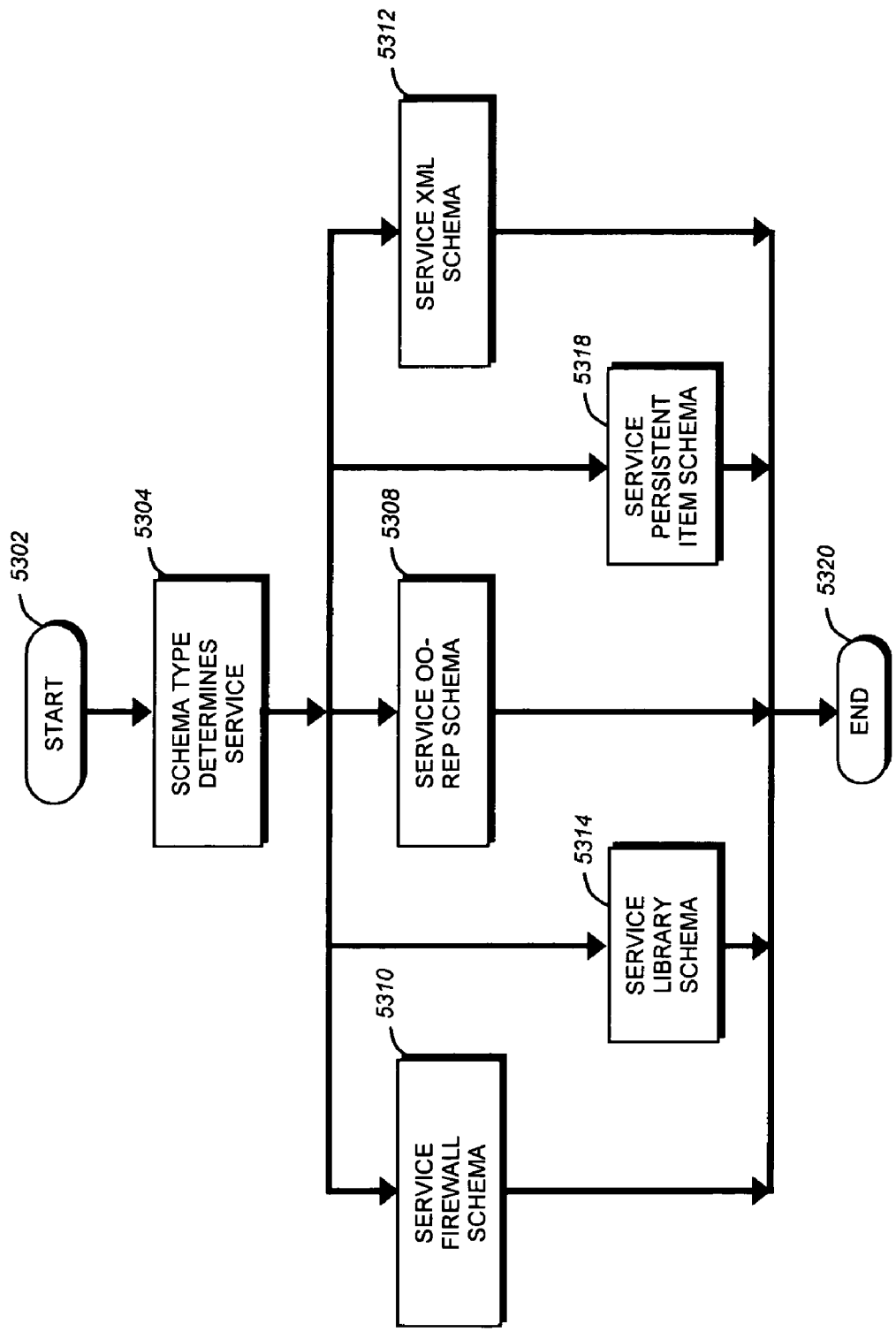
FIG. 53 depicts a schema service.

Referring to FIG. 53, the FACILITATION OF SCHEMA service 3168 may be provided according to the depicted procedure. The procedure may begin at the START logical block 5302, with a schema being provided as input to the procedure. Processing flow may proceed to the SCHEMA TYPE DETERMINES SERVICE logical block 5304. Here, a type associated with the schema may be determined and this type may be used to direct the processing flow, as depicted. In the case that the type is deemed to be a schema associated with a firewall, processing flow may proceed to logical block SERVICE FIREWALL SCHEMA 5310; if the type is deemed associated with an object-oriented representation, processing flow may proceed to logical block SERVICE OO-REP. SCEMA 5308; if the type is deemed associated with XML, processing flow may proceed to logical block SERVICE XML SCHEMA 5312; if the type is deemed associated with a library, processing flow may proceed to logical block SERVICE LIBRARY SCHEMA 5314; if the type is deemed associated with a persistent item, processing flow may proceed to logical block SERVICE PERSISTENT ITEM SCHEMA 5318. Logical block 5310 may represent the provision of a function related to a firewall, which may be described in the schema. For example and without limitation, the schema may describe a virtual private network configuration as it relates to the firewall. In this case, the function related to the firewall may be the establishment of a VPN connection to the firewall according to the configuration. This may provide a secure communication channel, which may persist beyond the execution of this service 3168 and which may secure communications between components of the system 2802. Logical block 5308 may represent the provision of a function related to an object-oriented representation, which may be embodied by the schema. For example and without limitation, this function may provide a rendition of the object-oriented representation according the Unified Modeling Language. This rendition may be graphical, such as may be embodied by an image data file, and/or it may be textual, such as may be embodied in an XML Metadata Interchange (XMI) file. Logical block 5312 may represent the provision of a function related to XML, which may be described and/or embodied by the schema. For example and without limitation, this function may include a parsing, interpreting, writing, rewriting, storing, retrieving, protecting, encrypting, decrypting, or otherwise processing XML. Logical block 5314 may represent the provision of a function related to a library, such as a library with books and/or a software library, either of which may be described and/or embodied by the schema. In the case where the library is of books, this function may without limitation enable looking up in, checking out from, checking in to, purchasing from, subscribing to, and/or donating to the library. In the case where the library is a software library, this function may without limitation provide dynamic linking or other operative coupling to the library, documentation associated with the library, a functional description of the library, a generalized flow diagram related to the library, and so forth. Logical block 5318 may represent the provision of a function related to a persistent item, which may be embodied by the schema. For example and without limitation, this function may include providing persistent storage for a schema and/or a lookup mechanism by which a permanent or unchanging reference to the schema may be dereferenced.

The system 2802 may provide the user with a facilitation of transaction service. This service may be represented by the FACILITATION OF TRANSACTION logical block 3150 of FIG. 31 and may be described in detail hereinafter with reference to FIG. 54. Prior to accessing this service, the user may be required to gain access to the service by following the access procedure that may be represented by the ACCESS: TRANSACTION logical block 3118 of FIG. 31, which may be described hereinbefore with reference to FIG. 54.

Figure 54:
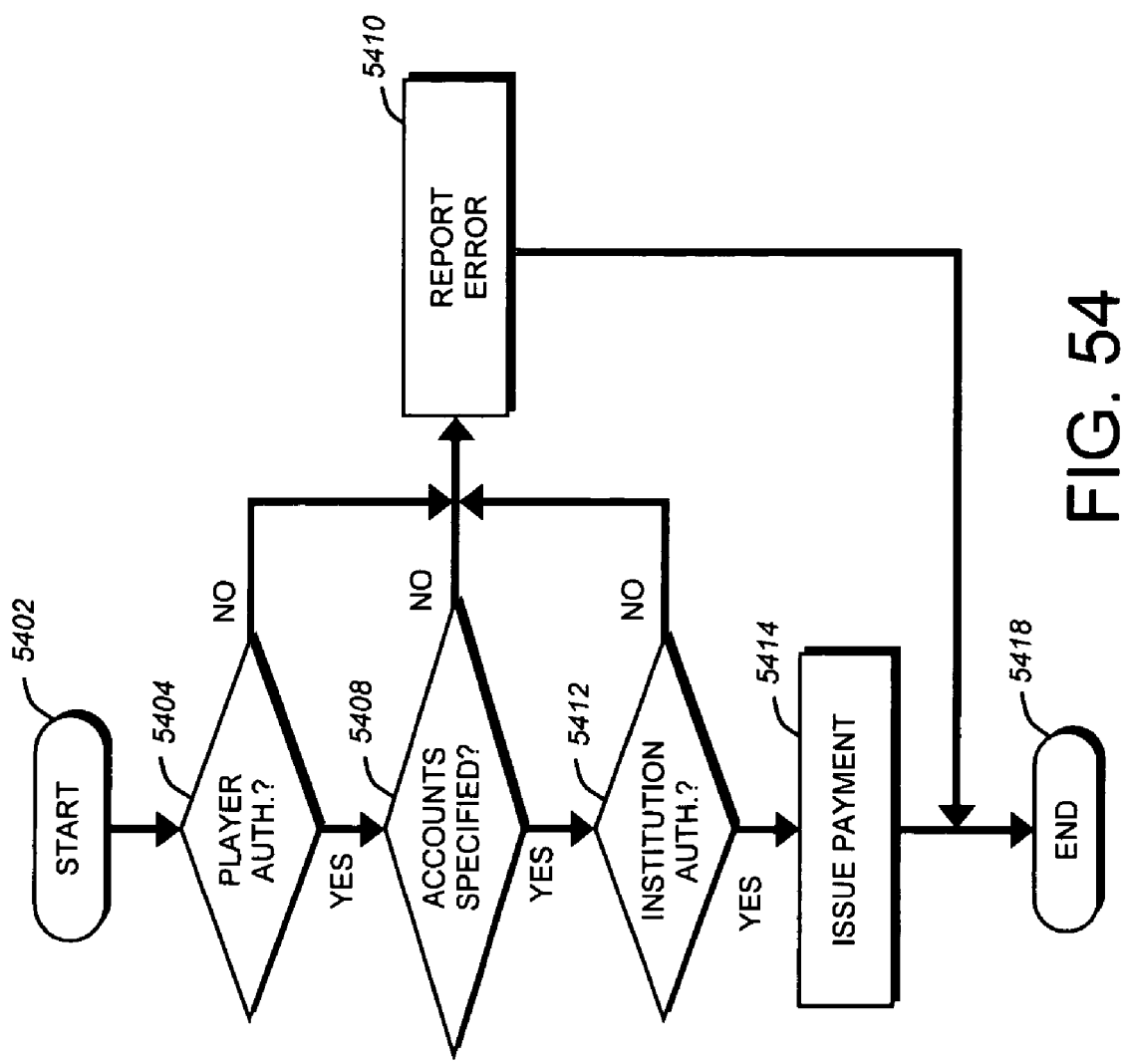
FIG. 54 depicts a transaction service.

Referring to FIG. 54, the facilitation of transaction service may be provided according to the depicted procedure. The procedure may begin at the START logical block 5402, with processing flow continuing as shown to the logical block 5404 (labeled PAYER AUTH.?). This logical block may represent a test to see if the payer has authorized a transaction. If the result of the test is negative, processing flow may proceed to the REPORT ERROR logical block 5410, where an error code or indication of error may be provided. Otherwise, processing flow may proceed to the logical block 5408 (labeled ACCOUNTS SPECIFIED?) where a test may determine whether a source account was specified for the transaction. If the result of the test is negative, processing flow may proceed as shown to logical block 5410. Otherwise, processing flow may continue to logical block 5412 where a test may determine whether a financial institution that may be associated with the account authorizes the transaction. If the result of this test is negative, processing flow may proceed as shown to logical block 5410. Otherwise, processing flow may continue to the ISSUE PAYMENT logical block 5414, which the payment may be drawn from the source account and deposited into a destination account. Whether from logical block 5414 or logical block 5410, processing flow may proceed to the END logical block 5418, where this procedure may end, perhaps producing a code, record, or other indication of completion of the procedure.

The system 2802 may provide a facilitation of affiliate service. This service may be represented as the FACILITATION OF AFFILIATE logical block 3164 of FIG. 31, which may be described in detail hereinafter with reference to FIG. 55. Prior to accessing this service, the user may be required to gain access to the service by following the access procedure that may be represented by the ACCESS: AFFILIATE logical block 3132 of FIG. 31, which may be described hereinbefore with reference to FIG. 36.

Figure 55:
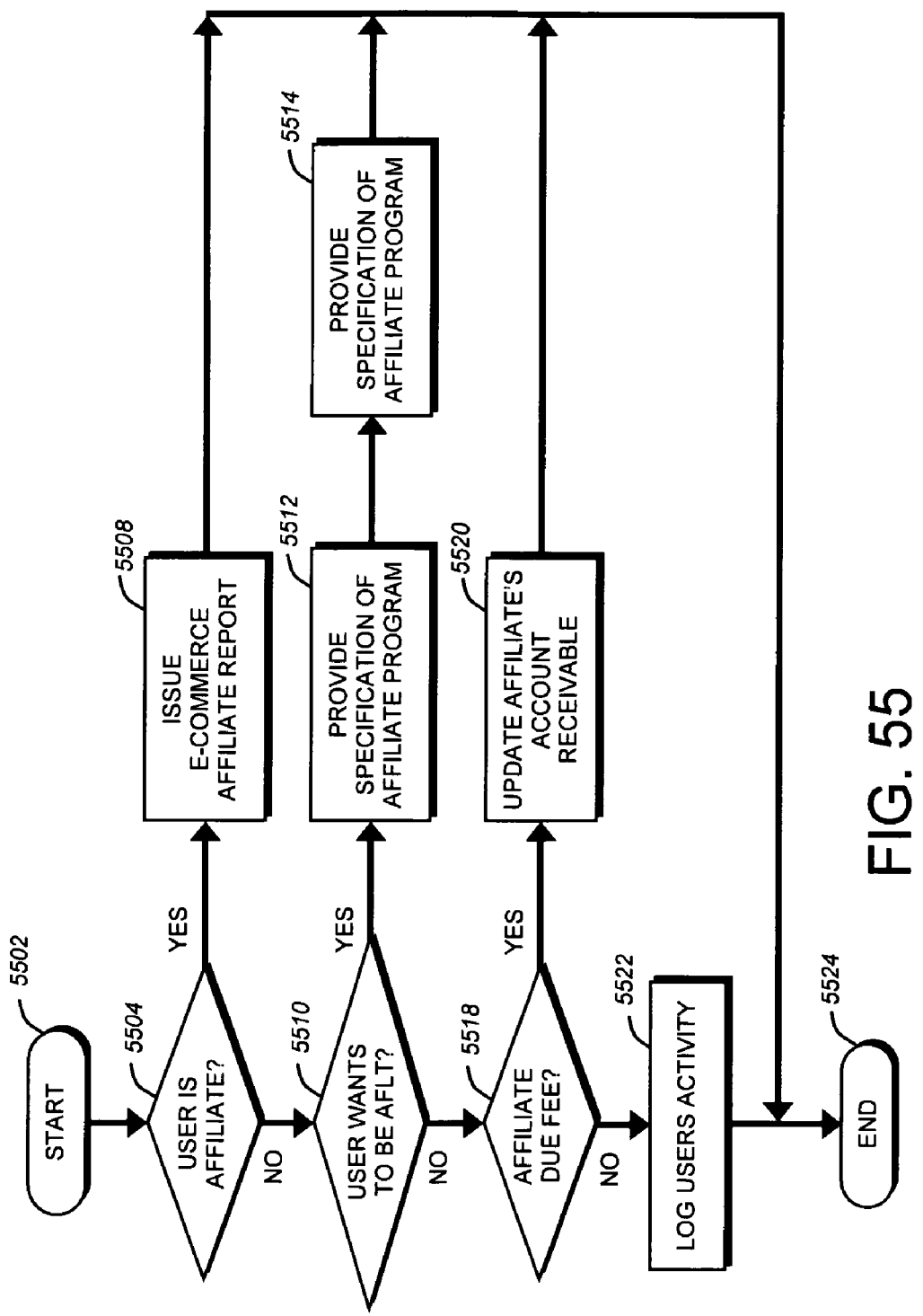
FIG. 55 shows an affiliate process.

Referring to FIG. 55, the FACILITATION OF AFFILIATE service 3164 may be provided according to the depicted procedure. The procedure may begin at the START logical block 5502. Then, processing flow may continue to the test that may be represented by logical block 5504, which may determine whether the user is an affiliate. An affiliate may be identified as such by its membership in an affiliate program and/or affiliate network, an indication of which may, without limitation, both be stored in one of the databases 2818 and be selected/referenced during the test in logical block 5504. If the result of this test is affirmative, processing flow may continue to the ISSUE E-COMMERCE AFFILIATE REPORT logical block 5508 where an e-commerce affiliate report may be issued to the user. This report may contain an aggregated or disaggregated view of referrals provided by the affiliate and/or an account receivable associated with the referrals. However, if the result of the test in logical block 5504 is negative, processing flow may continue to a test that may be represented by logical block 5510 (labeled USER WANTS TO BE AFLT.?), where a test may determine whether the user is interested in becoming an affiliate. If the result of this test is affirmative, processing flow may continue to the PROVIDE SPECIFICATION OF AFFILIATE PROGRAM logical block 5512, where the user may be provided with a legal and/or contractual specification of the affiliate program, which may be provided in a human-readable format (such as and without limitation a PDF document) and/or a computer-readable format (such as and without limitation an XML file). From this point, the processing flow may continue to the ADD USER TO AFFILIATE NETWORK logical block 5514, where the user may be added to an affiliate network, such as by writing an indication of the user's inclusion in an affiliate network into one of the databases 2818. However, if the result of the test in logical block 5518 is negative then processing flow may continue to the test represented by the logical block 5522 (labeled LOG USER'S ACTIVITY). Here, an indication of an activity by the user that may have caused the activation of this procedure may be written into one of the databases 2818. For example and without limitation, the user may have selected a promotional Web link from an affiliate Web site for which no fee is associated, but for which a log of user activity may be desired. This activity may be logged. However, if the test at logical block 5518 results in an affirmative result, processing flow may continue to logical block 5520, where an update to an affiliate's account receivable may be recorded, wherein the affiliate may be one of the users 2804 of the system 2802 and wherein the user may have taken an action associated with the affiliate (such as and without limitation selecting a particular Web link), which may cause a fee to be due to the affiliate. Whether from logical block 5508, 5514, 5520, or 5522, processing flow, as shown, may continue to the END logical block 5524, where this procedure may end, perhaps producing a code or other indication of completion of the transaction.

Other electronic commerce systems may similarly be employed in an enhanced syndication system. Thus various combinations of the above techniques may be employed for Internet-based purchasing, advertising, auctions, reverse auctions, product reviews, discussion groups, group purchasing, shopping cart transactions, and the like.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A system for managing a plurality of data feeds, the system comprising a computer having a non-transitory computer readable medium having stored thereon instructions which, when executed by a processor of the computer, causes the processor to perform the steps of:
    using a syndication platform to manage publication of a plurality of data feeds including a plurality of items;
    using a processing service that includes a plurality of services including at least one of a security service, an identification service, an authentication service, a format service, and a financial transaction service, wherein the processing service includes using tag-level encryption to provide a security setting for at least one element of a message that is included within the plurality of items;
    using a semantic service associated with the syndication platform, to provide an automated semantic analysis of one or more of the plurality of items, wherein at least one output of the semantic analysis is an aggregation of a new data feed based at least in part on the plurality of items, wherein items included within the new data feed are selected and organized within the new data feed based in part on the tag-level encryption security setting, and wherein the semantic service categorizes items according to popularity; and
    associating the new data feed with a security infrastructure service that includes multi-level security, wherein the multi-level security comprises at least one of a device-level security, a feed-level security, an item-level security, a field-level security, a tag-level security and a service level security.

2. The system of claim 1, wherein the semantic service associates one of the items with one or more other ones of the plurality of items.

3. The system of claim 2, wherein at least one of the plurality of items is an outline.

4. The system of claim 1, wherein the semantic service includes an outlining service.

5. The system of claim 4, wherein the outlining service uses the Outline Processing Markup Language.

6. The system of claim 4, wherein the outlining service interrelates the plurality of items in a hierarchical tree structure.

7. The system of claim 6, further comprising a plurality of outlines, each outline describing relationships between a plurality of items.

8. The system of claim 1, wherein at least one of the items includes data from a relational database.

9. The system of claim 1, wherein at least one of the items includes a file.

10. The system of claim 9, wherein the file includes one or more of an audio file, an image file, a movie file, a word processing file, a spreadsheet file, a presentation file, a document, an HTML file, a text file, an executable file, and a script.

11. The system of claim 1, wherein the semantic service additionally categorizes items according to file type.

12. The system of claim 1, wherein the semantic service additionally categorizes items according to relationships with other items.

13. The system of claim 1, wherein the semantic service additionally categorizes items according to user annotations.

14. The system of claim 1, wherein the semantic service enriches metadata associated with one or more of the items.

15. A method for use in a computer having a non-transitory computer readable medium having stored thereon instructions, the instructions when executed by a processor of a computer causes the processor to perform the steps comprising:
    publishing a plurality of items in one or more data feeds for subscription;
    automatically semantically analyzing the plurality of items;
    wherein the one or more of the plurality of items is categorized according to popularity;
    providing a processing service including at least one or more of a security service, an identification service, an authentication service, a format service, and a financial transaction service, wherein the processing service includes using tag-level encryption to provide a security setting for at least one element of a message that is included within the plurality of items;

providing a multi-level security using a security infrastructure service, wherein the multi-level security comprises at least one of a device-level security, a feed-level security, an item-level security, a field-level security, a tag-level security and a service-level security; and transmitting a data feed, from among the one or more data feeds, to fulfill a user's subscription request, wherein the transmitted data feed is selected based at least in part on the security setting.

16. The method of claim 15, further comprising semantically associating one of the items with one or more other ones of the plurality of items.

17. The method of claim 16, wherein at least one of the plurality of items is an outline.

18. The method of claim 15, further comprising providing an outlining service for describing relationships among two or more of the plurality of items.

19. The method of claim 18, wherein the outlining service uses the Outline Processing Markup Language.

20. The method of claim 18, wherein the outlining service interrelates the plurality of items in a hierarchical tree structure.

21. The method of claim 20, further comprising interrelating two or more of the items through a plurality of outlines.

22. The method of claim 15, wherein at least one of the items includes data from a relational database.

23. The method of claim 15, wherein at least one of the items includes a file.

24. The method of claim 23, wherein the file includes one or more of an audio file, an image file, a movie file, a word processing file, a spreadsheet file, a presentation file, a document, an HTML file, a text file, an executable file, and a script.

25. The method of claim 15, wherein the one or more of the plurality of items is additionally categorized according to file type.

26. The method of claim 15, wherein the one or more of the plurality of items is additionally categorized according to relationships with other items.

27. The method of claim 15, wherein the one or more of the plurality of items is additionally categorized according to user annotations.

28. The method of claim 15, wherein automatically semantically analyzing the plurality of items includes enriching metadata associated with one or more of the items.

29. The method of claim 28, wherein automatically semantically analyzing the plurality of items includes enriching metadata using a dictionary.

30. The method of claim 28, wherein automatically semantically analyzing the plurality of items includes enriching metadata using a thesaurus.

31. The method of claim 28, wherein automatically semantically analyzing the plurality of items includes enriching metadata by analyzing a relationship of one of the items to one or more other ones of the items.

32. The method of claim 28, wherein automatically semantically analyzing the plurality of items includes enriching metadata by analyzing one or more of a time of publication of an item, an author of an item, a source of an item, or metadata of an item.

33. The method of claim 28, wherein automatically semantically analyzing the plurality of items includes enriching metadata by analyzing a body of an item.

34. The method of claim 33, wherein automatically semantically analyzing the plurality of items includes performing a language analysis of content of the body.

35. The method of claim 15, wherein automatically semantically analyzing the plurality of items includes enriching content of one of the plurality of items.

36. The method of claim 15, wherein at least one of the one or more data feeds includes an aggregated data feed from a plurality of sources.

37. The method of claim 36, wherein the aggregated data feed is filtered before publication.

38. The method of claim 36, wherein the aggregated data feed includes aggregated news content relating to an entity.

39. The method of claim 38, wherein the plurality of items includes stored data relating to the entity.

40. The method of claim 39, wherein the entity includes a corporate entity and the stored data includes stored data relating to one or more financial instruments of the corporate entity.

41. The method of claim 40, wherein the financial instrument includes one or more of a publicly traded security, a bond, a privately held security, an option, and a futures contract.

42. The method of claim 15, wherein automatically semantically analyzing the plurality of items includes structuring content of the plurality of items by associating items according to a semantic relationship of the items.

43. The method of claim 15, wherein automatically semantically analyzing the plurality of items includes formatting one of the plurality of items for display according to a semantic evaluation.

44. The method of claim 15, wherein automatically semantically analyzing the plurality of items includes modifying metadata for one of the plurality of items.

45. The method of claim 15, wherein automatically semantically analyzing the plurality of items includes interpreting language of at least one item.

46. The method of claim 15, further comprising storing semantic data in a searchable archive.

47. The method of claim 15, further comprising providing a user interface adapted to display one of the items according to semantic content of the item.

* * * * *

UNITED STATES PATENT AND TRADEMARK OFFICE
CERTIFICATE OF CORRECTION

| | |
|---|---|
| PATENT NO. | : 8,200,775 B2 |
| APPLICATION NO. | : 11/223826 |
| DATED | : June 12, 2012 |
| INVENTOR(S) | : James F. Moore |

It is certified that error appears in the above-identified patent and that said Letters Patent is hereby corrected as shown below:

In column 76, line 18-19, in claim 1, delete "service level" and insert -- service-level --, therefor.

Signed and Sealed this
Twenty-fifth Day of September, 2012

David J. Kappos
*Director of the United States Patent and Trademark Office*